(12) United States Patent
Butlin et al.

(10) Patent No.: US 10,434,186 B2
(45) Date of Patent: Oct. 8, 2019

(54) FUNCTIONALIZED LINEAR LIGANDS AND COMPLEXES THEREOF

(71) Applicant: LUMIPHORE, INC., Berkeley, CA (US)

(72) Inventors: Nathaniel G. Butlin, Pacifica, CA (US); Darren Magda, San Leandro, CA (US); Jide Xu, Richmond, CA (US)

(73) Assignee: LUMIPHORE, INC., Berkeley, CA (US)

( * ) Notice: Subject to any disclaimer, the term of this patent is extended or adjusted under 35 U.S.C. 154(b) by 0 days.

(21) Appl. No.: 15/538,610

(22) PCT Filed: Dec. 21, 2015

(86) PCT No.: PCT/US2015/067170
§ 371 (c)(1),
(2) Date: Jun. 21, 2017

(87) PCT Pub. No.: WO2016/106241
PCT Pub. Date: Jun. 30, 2016

(65) Prior Publication Data
US 2017/0360956 A1 Dec. 21, 2017

Related U.S. Application Data

(60) Provisional application No. 62/095,617, filed on Dec. 22, 2014.

(51) Int. Cl.
| | | |
|---|---|---|
| *C07C 233/64* | (2006.01) | |
| *A61K 47/68* | (2017.01) | |
| *C07F 5/00* | (2006.01) | |
| *A61K 51/08* | (2006.01) | |
| *A61K 49/00* | (2006.01) | |
| *A61K 51/04* | (2006.01) | |
| *A61K 51/10* | (2006.01) | |
| *C07D 213/81* | (2006.01) | |
| *C07D 213/89* | (2006.01) | |

(52) U.S. Cl.
CPC ...... *A61K 47/6887* (2017.08); *A61K 49/0002* (2013.01); *A61K 49/0013* (2013.01); *A61K 51/0406* (2013.01); *A61K 51/0497* (2013.01); *A61K 51/08* (2013.01); *A61K 51/1093* (2013.01); *A61K 51/1096* (2013.01); *C07C 233/64* (2013.01); *C07D 213/81* (2013.01); *C07D 213/89* (2013.01); *C07F 5/003* (2013.01); *A61K 2121/00* (2013.01)

(58) Field of Classification Search
CPC ............ A61K 47/6887; A61K 49/0002; A61K 49/0013; A61K 51/0406; A61K 51/0497; A61K 51/08; A61K 51/1093; A61K 51/1096; A61K 2121/00; C07C 233/64; C07D 211/00; C07F 5/003
See application file for complete search history.

(56) References Cited

U.S. PATENT DOCUMENTS

| | | | |
|---|---|---|---|
| 4,698,431 A | 10/1987 | Raymond et al. | |
| 5,049,280 A | 9/1991 | Raymond et al. | |
| 5,624,901 A | 4/1997 | Raymond et al. | |
| 6,406,297 B1 | 6/2002 | Raymond et al. | |
| 6,515,113 B2 | 2/2003 | Raymond et al. | |
| 6,846,915 B2 | 1/2005 | Raymond et al. | |
| 7,018,850 B2 | 3/2006 | Raymond et al. | |
| 8,557,601 B2 * | 10/2013 | Raymond ............ | C07D 213/89 436/172 |
| 2008/0213780 A1 | 9/2008 | Butlin et al. | |
| 2008/0213917 A1 | 9/2008 | Raymond et al. | |
| 2009/0023928 A1 | 1/2009 | Raymond et al. | |
| 2010/0015725 A1 | 1/2010 | Raymond et al. | |
| 2013/0183235 A1* | 7/2013 | Ramdahl ............ | A61K 51/0478 424/1.53 |
| 2014/0039169 A1 | 2/2014 | Raymond et al. | |

FOREIGN PATENT DOCUMENTS

| | | |
|---|---|---|
| WO | WO 2008/008797 A1 | 1/2008 |
| WO | WO 2011/025790 A1 | 3/2011 |
| WO | WO 2011/079291 | 6/2011 |
| WO | WO 2014/078690 A1 | 5/2014 |
| WO | WO 2015/157057 A1 | 10/2015 |

OTHER PUBLICATIONS

Berge et al., "Pharmaceutical Salts." Journal of Pharmaceutical Sciences, vol. 66, No. 1 (1977).
Doble et al., "Toward Optimized High-Relaxivity MRI Agents: The Effect of Ligand Basicity on the Thermodynamic Stability of Hexadentate Hydroxypyridonate/Catecholate Gadolinium(III) Complexes." Inorganic Chemistry, vol. 42, No. 16 (2003).
Keana and Cai, "New reagents for photoaffinity labeling: Synthsis and photolysis of functionalized perfluorophenyl azides." The Journal of Organic Chemistry, vol. 55, pp. 3640-3647 (1990).
Moore et al., "Eu(III) Complexes of Functionalized Octadentate 1-Hydroxypyridin-2-ones: Stability, Bioconjugation, and Luminescence Resonance Energy Transfer Studies." Inorganic Chemistry, vol. 49, pp. 9928-9939 (2010).
Petoud et al., "Stable Lanthanide Luminescence Agents Highly Emissive in Aqueous Solution: Multidentate 2-Hydroxyisophthalamide Complexes of $Sm^{3+}$, $Eu^{3+}$, $Tb^{3+}$, $Dy^{3+}$." J. Am. Chem. Soc., vol. 125, pp. 13324-13325 (2003).
Samuel et al., "Water-Soluble 2-Hydroxyisophthalamides for Sensitization of Lanthanide Luminescence." Inorganic Chemistry, vol. 47, No. 17, pp. 7535-7544 (2008).

(Continued)

*Primary Examiner* — Timothy R Rozof

(74) *Attorney, Agent, or Firm* — Morgan, Lewis & Bockius LLP; Jeffry S. Mann

(57) ABSTRACT

The invention relates to chemical compounds and complexes that can be used in therapeutic and diagnostic applications.

32 Claims, 6 Drawing Sheets

(56) References Cited

OTHER PUBLICATIONS

Xu et al., "Gadolinium(III) 1,2-Hydroxypyridonate-Based Complexes: Toward MRI Contrast Agents of High Relaxivity." Inorganic Chemistry. vol. 43, pp. 5492-5494 (2004).
Yamada et al., Biochemistry, 20: 4836-4842 (1981).
Hajela et al., Tris-hydroxymethyl-Substituted Derivative of Gd-TREN-Me-3, 2-HOPO: An MRI Relaxation Agent with Improved Efficiency. Journal of the American Chem. Soc., vol. 122, No. 45, pp. 11228-11229 (2000).

* cited by examiner

FUNCTIONALIZED LINEAR LIGANDS AND COMPLEXES THEREOF

CROSS-REFERENCES TO RELATED APPLICATIONS

This application is a 371 U.S. National Phase application of PCT/US2015/067170 filed Dec. 21, 2015, which claims the benefit under 35 U.S.C. § 119(e) of U.S. Provisional Application No. 62/095,617, filed on Dec. 22, 2014, which is incorporated herein by reference in its entirety for all purposes.

FIELD OF THE INVENTION

The invention relates to chemical compounds and complexes that can be used in therapeutic and diagnostic applications.

DESCRIPTION OF EMBODIMENTS

1. Definitions

Figure 1:
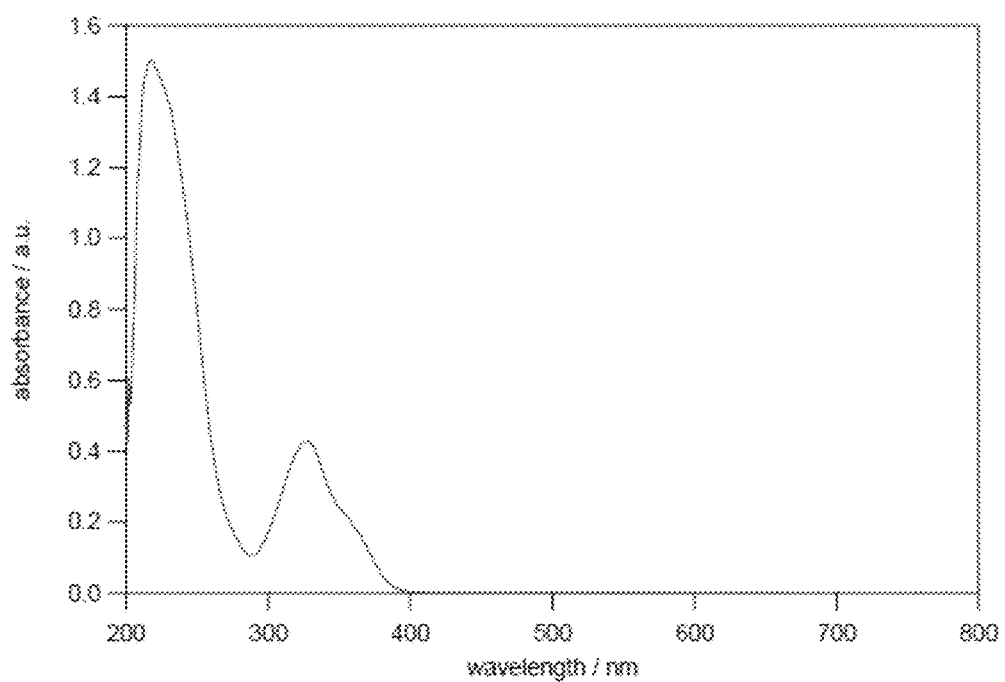
FIG. 1 shows 5LIO-Spermine-1,2-HOPO—NH2(Eu) Luminescent Bifunctional Chelate Molar Extinction Coefficient of 5LIO-spermine-1,2-HOPO—NH2 (2-8) as outlined in Example 12.

Where substituent groups are specified by their conventional chemical formulae, written from left to right, they optionally equally encompass the chemically identical substituents, which would result from writing the structure from right to left, e.g., —CH$_2$O— is intended to also recite —OCH$_2$—.

The term "alkyl", by itself or as part of another substituent, means a straight or branched chain hydrocarbon, which may be fully saturated, mono- or polyunsaturated and includes mono-, di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl" can refer to "alkylene", which by itself or as part of another substituent means a divalent radical derived from an alkane, as exemplified, but not limited, by —CH$_2$CH$_2$CH$_2$CH$_2$—. Typically, an alkyl (or alkylene) group will have from 1 to 30 carbon atoms. A "lower alkyl" or "lower alkylene" is a shorter chain alkyl or alkylene group, generally having eight or fewer carbon atoms. In some embodiments, alkyl refers to an alkyl or combination of alkyls selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The term "heteroalkyl," by itself or in combination with another term, means an alkyl in which one or more carbons are replaced with one or more heteroatoms selected from the group consisting of O, N, Si and S, (preferably O, N and S), wherein the nitrogen and sulfur atoms may optionally be oxidized and the nitrogen heteroatom may optionally be quaternized. The heteroatoms O, N, Si and S may be placed at any interior position of the heteroalkyl group or at the position at which the alkyl group is attached to the remainder of the molecule. In some embodiments, depending on whether a heteroatom terminates a chain or is in an interior position, the heteroatom may be bonded to one or more H or substituents such as ($C_1$, $C_2$, $C_3$, $C_4$, $C_5$ or $C_6$) alkyl according to the valence of the heteroatom. Examples of heteroalkyl groups include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. No more than two heteroatoms may be consecutive, as in, for example, —CH$_2$—NH—OCH$_3$ and —CH$_2$—O—Si(CH$_3$)$_3$, and in some instances, this may place a limit on the number of heteroatom substitutions. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. The designated number of carbons in heteroforms of alkyl, alkenyl and alkynyl includes the heteroatom count. For example, a ($C_1$, $C_2$, $C_3$, $C_4$, $C_5$ or $C_6$) heteroalkyl will contain, respectively, 1, 2, 3, 4, 5 or 6 atoms selected from C, N, O, Si and S such that the heteroalkyl contains at least one C atom and at least one heteroatom, for example 1-5 C and 1 N or 1-4 C and 2 N. Further, a heteroalkyl may also contain one or more carbonyl groups. In some embodiments, a heteroalkyl is any $C_2$-$C_{30}$ alkyl, $C_2$-$C_{25}$ alkyl, $C_2$-$C_{20}$ alkyl, $C_2$-$C_{15}$ alkyl, $C_2$-$C_{10}$ alkyl or $C_2$-$C_6$ alkyl in any of which one or more carbons are replaced by one or more heteroatoms selected from O, N, Si and S (or from O, N and S). In some embodiments, each of 1, 2, 3, 4 or 5 carbons is replaced with a heteroatom. The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

The terms "cycloalkyl" and "heterocycloalkyl", by themselves or in combination with other terms, refer to cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means a polyunsaturated, aromatic substituent that can be a single ring or optionally multiple rings (preferably 1, 2 or 3 rings) that are fused together or linked covalently. In some embodiments, aryl is a 3, 4, 5, 6, 7 or 8 membered ring, which is optionally fused to one or two other 3, 4, 5, 6, 7 or 8 membered rings. The term "heteroaryl" refers to aryl groups (or rings) that contain 1, 2, 3 or 4 heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

In some embodiments, any of alkyl, heteroalkyl, cycloalkyl, heterocycloalkyl, aryl and heteroaryl is optionally substituted. That is, in some embodiments, any of these groups is substituted or unsubstituted. In some embodiments, substituents for each type of radical are selected from those provided below.

Substituents for the alkyl, heteroalkyl, cycloalkyl and heterocycloalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents". In some embodiments, an alkyl group substituent is selected from -halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. In one embodiment, R', R", R'" and R"" are each independently selected from hydrogen, alkyl (e.g., $C_1$, $C_2$, $C_3$, $C_4$, $C_5$ and $C_6$ alkyl). In one embodiment, R', R", R'" and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. In one embodiment, R', R", R'" and R"" are each independently selected from hydrogen, alkyl, heteroalkyl, cycloalkyl, heterocycloalkyl, aryl, heteroaryl, alkoxy, thioalkoxy groups, and arylalkyl. When R' and R" are attached to the same nitrogen atom, they can be combined with the nitrogen atom to form a 5-, 6-, or 7-membered ring. For example, —NR'R" can include 1-pyrrolidinyl and 4-morpholinyl. In some embodiments, an alkyl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Similar to the substituents described for the alkyl radical, substituents for the aryl and heteroaryl groups are generically referred to as "aryl group substituents". In some embodiments, an aryl group substituent is selected from -halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system. In some embodiments, R', R", R'" and R"" are independently selected from hydrogen and alkyl (e.g., $C_1$, $C_2$, $C_3$, $C_4$, $C_5$ and $C_6$ alkyl). In some embodiments, R', R", R'" and R"" are independently selected from hydrogen, substituted or unsubstituted alkyl, substituted or unsubstituted heteroalkyl, substituted or unsubstituted aryl and substituted or unsubstituted heteroaryl. In some embodiments, R', R", R'" and R"" are independently selected from hydrogen, alkyl, heteroalkyl, aryl and heteroaryl. In some embodiments, an aryl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen and substituted or unsubstituted ($C_1$-$C_6$)alkyl.

The term "acyl" refers to a species that includes the moiety —C(O)R, where R has the meaning defined herein. Exemplary species for R include H, halogen, substituted or unsubstituted alkyl, substituted or unsubstituted aryl, substituted or unsubstituted heteroaryl, and substituted or unsubstituted heterocycloalkyl. In some embodiments, R is selected from H and ($C_1$-$C_6$)alkyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. In some embodiments, halogen refers to an atom selected from F, Cl and Br.

The term "heteroatom" includes oxygen (O), nitrogen (N), sulfur (S) and silicon (Si). In some embodiments, a heteroatom is selected from N and S. In some embodiments, the heteroatom is O.

Unless otherwise specified, the symbol "R" is a general abbreviation that represents a substituent group that is selected from acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound includes more than one R, R', R", R'" and R"" group, they are each independently selected.

For groups with solvent exchangeable protons, the ionized form is equally contemplated. For example, —COOH also refers to —COO⁻ and —OH also refers to —O⁻.

Any of the compounds disclosed herein can be made into a pharmaceutically acceptable salt. The term "pharmaceutically acceptable salts" includes salts of compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides any of the compounds disclosed herein in a prodrug form. Prodrugs of the compounds described herein are those compounds that readily undergo chemical changes under physiological conditions to provide the compounds of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. For example, the compounds may be labeled with deuterium (²H) or radiolabeled with radioactive isotopes, such as for example tritium (³H), iodine-125 (¹²⁵I) or carbon-14 (¹⁴C). All isotopic variations of the compounds of the present invention, whether radioactive or not, are intended to be encompassed within the scope of the present invention.

The symbol , displayed perpendicular to a bond, indicates the point at which the displayed moiety is attached to the remainder of the molecule.

In some embodiments, the definition of terms used herein is according to IUPAC.

2. Compositions

The invention provides numerous compounds (ligands) and metal ion complexes thereof. Generally, a ligand comprises a plurality of chelating moieties that are linked together by way of a scaffold moiety.

There are several factors to be considered in the design for an alpha chelating agent for anticancer therapy. Some of the key issues apart from the kinetics will be the high affinity for the target metal (such as Th) which at the same time needs to have a low exchange rate for other biologically significant metal ions. So, in our ligand design, the electronic properties of the target metal and ligand are considered and matched. The chelate should also be able to assume the appropriate coordination cavity size and geometry for the desired metal. In this case, Th, an actinide ion, is a "hard" cation and has a large charge-to-radius ratio. Hence, Th prefers "hard" electron donors and negatively charged oxygen donors. A coordination number of 8 or greater is generally preferred by actinide ions as they have a tendency to form stable complexes with ligands of high denticity; however, the selectivity towards the binding of the thorium will be determined by our design of the chelating unit. The effective but nonselective amino-carboxylic acid ligands such as DTPA can deplete essential biological metal ions from patients, thus causing serious health problems. Selecting the correct type of chelating unit, therefore, is an important factor in achieving high selectivity toward the specific metal ion.

A ligand can comprise numerous chelating moieties. Particularly useful ligands contain a number of chelating moieties sufficient to provide, for example, 6, 8 or 10 heteroatoms such as oxygen that coordinate with a metal ion to form a complex. The heteroatoms such as oxygen provide electron density for forming coordinate bonds with a positively charged ion, and such heteroatoms can thus be considered "donors". In some embodiments, the plurality of chelating moieties of a ligand comprises a plurality of oxygen donors and a metal ion (such as a radionuclide) is chelated to the ligand via at least one of the oxygen donors. In some embodiments, a ligand comprises a plurality of oxygen donors and a metal ion (such as a radionuclide) is chelated to the ligand via a plurality or all of the oxygen donors.

2.1. Ligands

In one aspect, the invention provides a compound (ligand) having the structure:

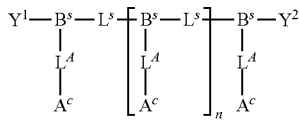

wherein n is an integer selected from 1, 2, 3, and 4; $Y^1$ and $Y^2$ are independently selected from H, substituted or unsubstituted alkyl, and substituted or unsubstituted heteroalkyl; each $B^s$ is independently selected from N, $CR^s$, B, $SiR^s$, and P; wherein $R^s$ is selected from H and unsubstituted $C_1$-$C_3$ alkyl; each $L^A$ is independently selected from a bond, —C(O)—, substituted or unsubstituted alkyl, and substituted or unsubstituted heteroalkyl; each $L^s$ is independently selected from substituted or unsubstituted alkyl and substituted or unsubstituted heteroalkyl; and each $A^c$ is an independently selected chelating moiety. Chelating moieties are as defined herein.

Any of the combinations of n, $Y^1$, $Y^2$, $B^s$, $L^A$, $L^s$, and $A^c$ are encompassed by this disclosure and specifically provided by the invention.

In some embodiments, each $L^A$ is independently selected from a bond, —C(O)—, —$(CH_2)_aC(O)$—, and —$O(CH_2)_aC(O)$—, wherein a is an integer selected from 1, 2, 3, 4, 5, and 6. In some embodiments, each $L^A$ is the same. In some embodiments, $L^A$ is —C(O)—.

In some embodiments, the ligand comprises a linker. In some embodiments, at least one $L^s$ is substituted with a linker. Linkers are as defined herein. In some embodiments, the linker is attached to a targeting moiety. In some embodiments, the ligand comprises a targeting moiety.

In some embodiments, the ligand comprises one or more modifying moieties. The modifying moieties can be the same or different.

In some embodiments, the compound (ligand) has a structure selected from:

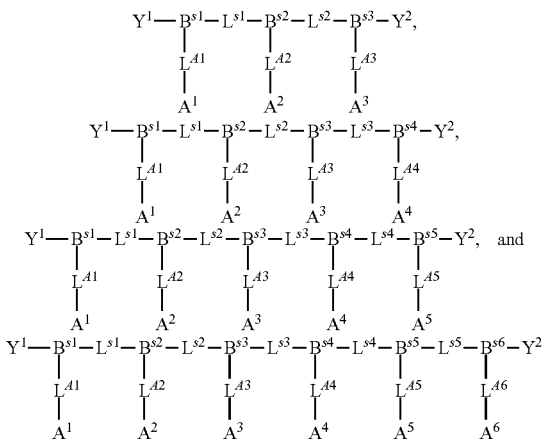

wherein $Y^1$ and $Y^2$ are independently selected from H, substituted or unsubstituted alkyl, and substituted or unsubstituted heteroalkyl; $B^{s1}$, $B^{s2}$, $B^{s3}$, $B^{s4}$, $B^{s5}$, and $B^{s6}$ are independently selected from N, $CR^s$, B, $SiR^s$, and P; wherein $R^s$ is selected from H and unsubstituted $C_1$-$C_3$ alkyl; $L^{A1}$, $L^{A2}$, $L^{A3}$, $L^{A4}$, $L^{A5}$, and $L^{A6}$ are independently selected from a bond, —C(O)—, substituted or unsubstituted alkyl, and substituted or unsubstituted heteroalkyl; $L^{s1}$, $L^{s2}$, $L^{s3}$, $L^{s4}$, and $L^{s5}$ are independently selected from substituted or unsubstituted alkyl and substituted or unsubstituted heteroalkyl, and $A^1$, $A^2$, $A^3$, $A^4$, $A^5$, and $A^6$ are independently selected chelating moieties.

Any of the combinations of $Y^1$, $Y^2$, $B^{s1}$, $B^{s2}$, $B^{s3}$, $B^{s4}$, $B^{s5}$, $B^{s6}$, $L^{A1}$, $L^{A2}$, $L^{A3}$, $L^{A4}$, $L^{A5}$, $L^{A6}$, $L^{s1}$, $L^{s2}$, $L^{s3}$, $L^{s4}$, $L^{s5}$, $A^1$, $A^2$, $A^3$, $A^4$, $A^5$, and $A^6$ are encompassed by this disclosure and specifically provided by the invention.

In some embodiments, at least one of $L^{s1}$, $L^{s2}$, $L^{s3}$, $L^{s4}$, and $L^{s5}$ is substituted with a linker. In some embodiments, one, two, three, four, or five of $L^{s1}$, $L^{s2}$, $L^{s3}$, $L^{s4}$, and $L^{s5}$ is/are substituted with a linker. In some embodiments, one of $L^{s1}$, $L^{s2}$, $L^{s3}$, $L^{s4}$, and $L^{s5}$ is substituted with a linker. In some embodiments, two of $L^{s1}$, $L^{s2}$, $L^{s3}$, $L^{s4}$, and $L^{s5}$ are substituted with a linker. In some embodiments, $L^{s1}$ is substituted with a linker. In some embodiments, $L^{s2}$ is substituted with a linker. In some embodiments, $L^{s3}$ is substituted with a linker. In some embodiments, $L^{s4}$ is substituted with a linker. In some embodiments, $L^{s5}$ is substituted with a linker. Linkers are as defined herein.

In some embodiments, $L^{s1}$, $L^{s2}$, $L^{s3}$, $L^{s4}$, and $L^{s5}$ are each independently selected from substituted or unsubstituted $C_1$-$C_8$ (i.e., $C_1$, $C_2$, $C_3$, $C_4$, $C_5$, $C_6$, $C_7$, $C_8$) alkyl and substituted or unsubstituted $C_1$-$C_8$ (i.e., $C_1$, $C_2$, $C_3$, $C_4$, $C_5$, $C_6$, $C_7$, $C_8$) heteroalkyl. In some embodiments, $L^{s1}$, $L^{s2}$, $L^{s3}$, $L^{s4}$, and $L^{s5}$ are each independently selected from substituted or unsubstituted $C_1$, $C_2$, $C_3$, $C_4$, $C_5$, $C_6$, $C_7$ and $C_8$ alkyl. In some embodiments, $L^{s1}$, $L^{s2}$, $L^{s3}$, $L^{s4}$, and $L^{s5}$ are each independently selected from substituted or unsubstituted $C_1$, $C_2$, $C_3$, $C_4$, $C_5$, $C_6$, $C_7$ and $C_8$ alkyl, wherein at least one of $L^{s1}$, $L^{s2}$, $L^{s3}$, $L^{s4}$, and $L^{s5}$ is substituted with a linker. In some embodiments, $L^{s1}$, $L^{s2}$, $L^{s3}$, $L^{s4}$, and $L^{s5}$ are each independently selected from substituted or unsubstituted $C_2$-$C_5$ alkyl. In some embodiments, $L^{s1}$, $L^{s2}$, $L^{s3}$, $L^{s4}$, and $L^{s5}$ are each independently selected from substituted or unsubstituted $C_2$-$C_5$ alkyl, wherein at least one of $L^{s1}$, $L^{s2}$, $L^{s3}$, $L^{s4}$, and $L^{s5}$ is substituted with a linker. In some embodiments, $L^{s1}$, $L^{s2}$, $L^{s3}$, $L^{s4}$, and $L^{s5}$ are each independently selected from substituted or unsubstituted $C_3$-$C_4$ alkyl. In some embodiments, $L^{s1}$, $L^{s2}$, $L^{s3}$, $L^{s4}$, and $L^{s5}$ are each independently selected from substituted or unsubstituted $C_3$-$C_4$ alkyl, wherein at least one of $L^{s1}$, $L^{s2}$, $L^{s3}$, $L^{s4}$, and $L^{s5}$ is substituted with a linker.

In some embodiments, $B^{s1}$, $B^{s2}$, $B^{s3}$, $B^{s4}$, $B^{s5}$, and $B^{s6}$ are N.

In some embodiments, $L^{A1}$, $L^{A2}$, $L^{A3}$, $L^{A4}$, $L^{A5}$, and $L^{A6}$ are independently selected from a bond, —C(O)—, —$(CH_2)_a$ C(O)—, and —$O(CH_2)_aC(O)$—, wherein a is an integer selected from 1, 2, 3, 4, 5, and 6. In some embodiments, $L^{A1}$, $L^{A2}$, $L^{A3}$, $L^{A4}$, $L^{A5}$, and $L^{A6}$ are the same. In some embodiments, $L^{A1}$, $L^{A2}$, $L^{A3}$, $L^{A4}$, $L^{A5}$, and $L^{A6}$ are —C(O)—.

In some embodiments, $Y^1$ and $Y^2$ are H.

2.1.1. Chelating Moieties $A^c$, $A^1$, $A^2$, $A^3$, $A^4$, $A^5$, and $A^6$ are chelating moieties having a structure independently selected from:

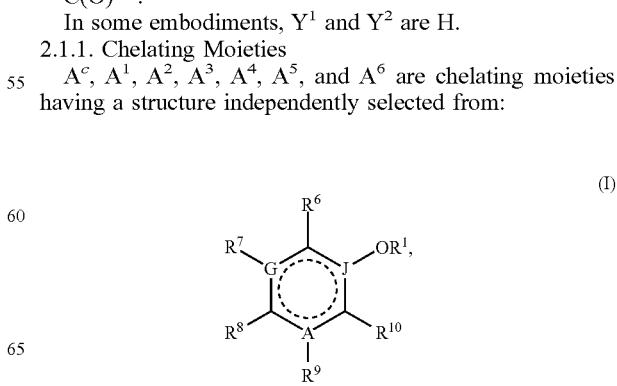

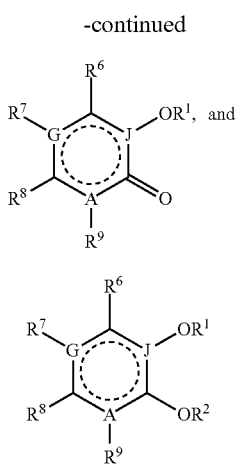

wherein A and G are independently selected from carbon, nitrogen and oxygen; J is selected from carbon and nitrogen; each $R^1$ and $R^2$ are independently selected from H, an enzymatically labile group, a hydrolytically labile group, a metabolically labile group, a photolytically labile group and a single negative charge; each $R^6$, $R^7$, $R^8$, $R^9$, and $R^{10}$ are independently selected from a bond to $L^A$, $L^{A1}$, $L^{A2}$, $L^{A3}$, $L^{A4}$, LAS, or $L^{A6}$, alkanediyl attached to $L^A$, $L^{A1}$, $L^{A2}$, $L^{A3}$, $L^{A4}$, $L^{A5}$, or $L^{A6}$, H, substituted or unsubstituted alkyl, substituted or unsubstituted heteroalkyl, halogen, CN, —$CF_3$, —$C(O)R^{17}$, —$SO_2NR^{17}R^{18}$, —$NR^{17}R^{18}$, —$OR^{17}$, —$S(O)_2R^{17}$, —$COOR^{17}$, —$S(O)_2OR^{17}$, —$OC(O)R^{17}$, —$C(O)NR^{17}R^{18}$, —$(CH_2)_mC(O)NR^{17}R^{18}$, —$O(CH_2)_mC(O)NR^{17}R^{18}$, —$NR^{17}C(O)R^{18}$, —$NR^{17}SO_2R^{18}$, and —$NO_2$, wherein at least two of $R^6$, $R^7$, $R^8$, $R^9$, and $R^{10}$ are optionally joined to form a ring system selected from substituted or unsubstituted cycloalkyl, substituted or unsubstituted heterocycloalkyl, substituted or unsubstituted aryl and substituted or unsubstituted heteroaryl; m is an integer selected from 1, 2, 3, 4, 5, and 6; $R^{17}$ and $R^{18}$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and $R^{17}$ and $R^{18}$, together with the atoms to which they are attached, are optionally joined to form a 5-, 6- or 7-membered ring; when A is oxygen, $R^9$ is not present; and when G is oxygen, $R^7$ is not present; wherein $A^c$ is attached to $L^A$ through a member selected from $R^6$, $R^7$, $R^8$, $R^9$ and $R^{10}$; $A^1$ is attached to $L^{A1}$ through a member selected from $R^6$, $R^7$, $R^8$, $R^9$ and $R^{10}$; $A^2$ is attached to $L^{A2}$ through a member selected from $R^6$, $R^7$, $R^8$, $R^9$ and $R^{10}$; $A^3$ is attached to $L^{A3}$ through a member selected from $R^6$, $R^7$, $R^8$, $R^9$ and $R^{10}$; $A^4$ is attached to $L^{A4}$ through a member selected from $R^6$, $R^7$, $R^8$, $R^9$ and $R^{10}$; $A^5$ is attached to $L^{A5}$ through a member selected from $R^6$, $R^7$, $R^8$, $R^9$ and $R^{10}$; and $A^6$ is attached to $L^{A6}$ through a member selected from $R^6$, $R^7$, $R^8$, $R^9$ and $R^{10}$.

In some embodiments, when $A^c$ has a structure according to formula (I), $A^c$ is attached to $L^A$ through $R^6$ or $R^{10}$. In some embodiments, when $A^c$ has a structure according to formula (II) or (III), $A^c$ is attached to $L^A$ through $R^6$ or $R^9$. In some embodiments, when $A^1$ has a structure according to formula (I), $A^1$ is attached to $L^{A1}$ through $R^6$ or $R^{10}$. In some embodiments, when $A^1$ has a structure according to formula (II) or (III), $A^1$ is attached to $L^{A1}$ through $R^6$ or $R^9$. In some embodiments, when $A^2$ has a structure according to formula (I), $A^2$ is attached to $L^{A2}$ through $R^6$ or $R^{10}$. In some embodiments, when $A^2$ has a structure according to formula (II) or (III), $A^2$ is attached to $L^{A2}$ through $R^6$ or $R^9$. In some embodiments, when $A^3$ has a structure according to formula (I), $A^3$ is attached to $L^{A3}$ through $R^6$ or $R^{10}$. In some embodiments, when $A^3$ has a structure according to formula (II) or (III), $A^3$ is attached to $L^{A3}$ through $R^6$ or $R^9$. In some embodiments, when $A^4$ has a structure according to formula (I), $A^4$ is attached to $L^{A4}$ through $R^6$ or $R^{10}$. In some embodiments, when $A^4$ has a structure according to formula (II) or (III), $A^4$ is attached to $L^{A4}$ through $R^6$ or $R^9$. In some embodiments, when $A^5$ has a structure according to formula (I), $A^5$ is attached to $L^{A5}$ through $R^6$ or $R^{10}$. In some embodiments, when $A^5$ has a structure according to formula (II) or (III), $A^5$ is attached to $L^{A5}$ through $R^6$ or $R^9$. In some embodiments, when $A^6$ has a structure according to formula (I), $A^6$ is attached to $L^{A6}$ through $R^6$ or $R^{10}$. In some embodiments, when $A^6$ has a structure according to formula (II) or (III), $A^6$ is attached to $L^{A6}$ through $R^6$ or $R^9$.

In some embodiments, $A^c$, $A^1$, $A^2$, $A^3$, $A^4$, $A^5$, and $A^6$ are chelating moieties having a structure independently selected from:

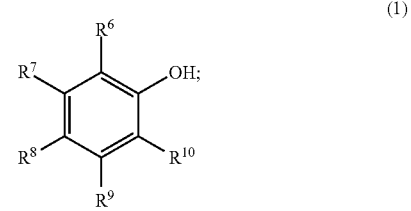

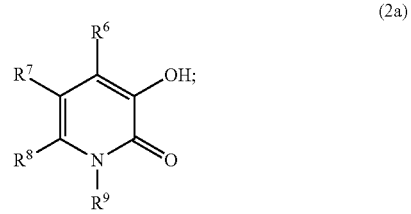

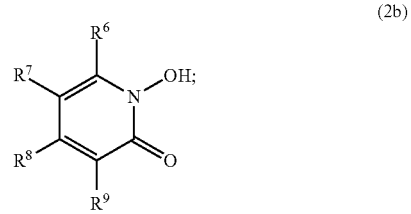

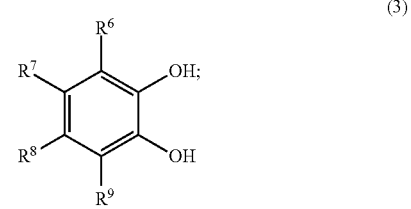

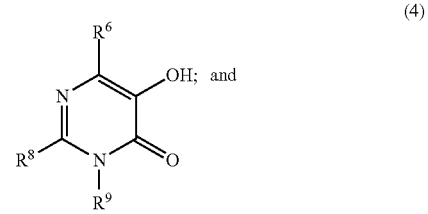

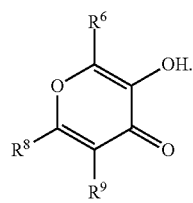

$R^6$, $R^7$, $R^8$, $R^9$, and $R^{10}$ are as defined herein.

In some embodiments, when $A^c$ has a structure according to formula (1), $A^c$ is attached to $L^A$ through $R^6$ or $R^{10}$. In some embodiments, when $A^c$ has a structure according to formula (2a), (2b), (3), (4) or (5), $A^c$ is attached to $L^A$ through $R^6$ or $R^9$. In some embodiments, when $A^1$ has a structure according to formula (1), $A^1$ is attached to $L^{A1}$ through $R^6$ or $R^{10}$. In some embodiments, when $A^1$ has a structure according to formula (2a), (2b), (3), (4) or (5), $A^1$ is attached to $L^{A1}$ through $R^6$ or $R^9$. In some embodiments, when $A^2$ has a structure according to formula (1), $A^2$ is attached to $L^{A2}$ through $R^6$ or $R^{10}$. In some embodiments, when $A^2$ has a structure according to formula (2a), (2b), (3), (4) or (5), $A^2$ is attached to $L^{A2}$ through $R^6$ or $R^9$. In some embodiments, when $A^3$ has a structure according to formula (1), $A^3$ is attached to $L^{A3}$ through $R^6$ or $R^{10}$. In some embodiments, when $A^3$ has a structure according to formula (2a), (2b), (3), (4) or (5), $A^3$ is attached to $L^{A3}$ through $R^6$ or $R^9$. In some embodiments, when $A^4$ has a structure according to formula (1), $A^4$ is attached to $L^{A4}$ through $R^6$ or $R^{10}$. In some embodiments, when $A^4$ has a structure according to formula (2a), (2b), (3), (4) or (5), $A^4$ is attached to $L^{A4}$ through $R^6$ or $R^9$. In some embodiments, when $A^5$ has a structure according to formula (1), $A^5$ is attached to $L^{A5}$ through $R^6$ or $R^{10}$. In some embodiments, when $A^5$ has a structure according to formula (2a), (2b), (3), (4) or (5), $A^5$ is attached to $L^{A5}$ through $R^6$ or $R^9$. In some embodiments, when $A^6$ has a structure according to formula (1), $A^6$ is attached to $L^{A6}$ through $R^6$ or $R^{10}$. In some embodiments, when $A^6$ has a structure according to formula (2a), (2b), (3), (4) or (5), $A^6$ is attached to $L^{A6}$ through $R^6$ or $R^9$.

In some embodiments, $A^c$, $A^1$, $A^2$, $A^3$, $A^4$, $A^5$, and $A^6$ are chelating moieties having a structure independently selected from:

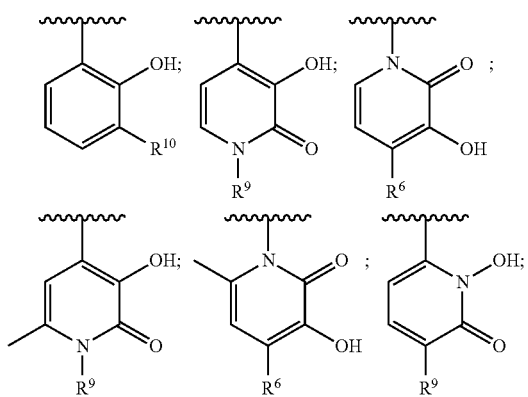

$R^6$, $R^9$, and $R^{10}$ are as defined herein.

In some embodiments, each $A^c$ is the same. In some embodiments, $A^1$, $A^2$, and $A^3$ are the same. In some embodiments, $A^1$, $A^2$, $A^3$, and $A^4$ are the same. In some embodiments, $A^1$, $A^2$, $A^3$, $A^4$, and $A^5$ are the same. In some embodiments, $A^1$, $A^2$, $A^3$, $A^4$, $A^5$, and $A^6$ are the same.

In some embodiments, $A^c$, $A^1$, $A^2$, $A^3$, $A^4$, $A^5$, and $A^6$ are chelating moieties having the structure:

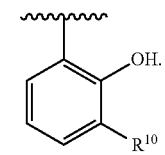

$R^{10}$ is as defined herein.

In some embodiments, $A^c$, $A^1$, $A^2$, $A^3$, $A^4$, $A^5$, and $A^6$ are chelating moieties having a structure independently selected from:

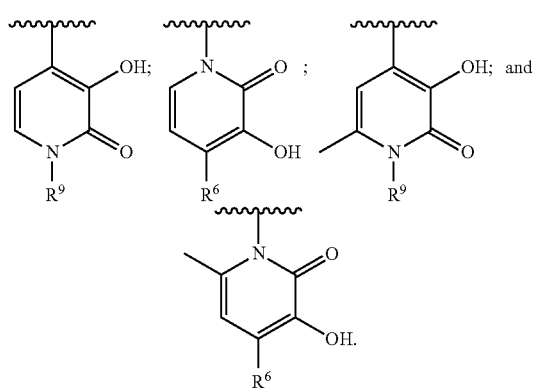

$R^6$ and $R^9$ are as defined herein.

In some embodiments, $A^c$, $A^1$, $A^2$, $A^3$, $A^4$, $A^5$, and $A^6$ are chelating moieties having a structure independently selected from:

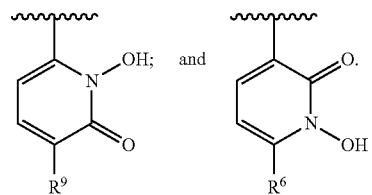

$R^6$ and $R^9$ are as defined herein.

In some embodiments, $A^c$, $A^1$, $A^2$, $A^3$, $A^4$, $A^5$, and $A^6$ are chelating moieties having the structure:

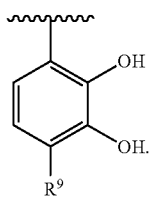

$R^9$ is as defined herein.

In some embodiments, at least one of $A^1$, $A^2$, $A^3$, $A^4$, $A^5$, and $A^6$ does not have the structure:

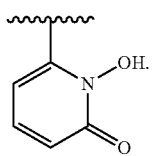 [SMILES: *c1cccc(=O)n1O]

In some embodiments, none of $A^1$, $A^2$, $A^3$, $A^4$, $A^5$, and $A^6$ have the structure:

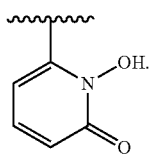 [SMILES: *c1cccc(=O)n1O]

In some embodiments, one, some or all of the chelating moieties ($A^c$ or $A^1$, $A^2$, $A^3$, $A^4$, $A^5$, and $A^6$) comprise(s) a modifying moiety. Modifying moieties are as defined herein. In some embodiments, one, two, three, four, five or six of the chelating moieties ($A^c$ or $A^1$, $A^2$, $A^3$, $A^4$, $A^5$, and $A^6$) comprise(s) a modifying moiety.

In some embodiments, $R^6$, $R^7$, $R^8$, $R^9$, or $R^{10}$ of a given chelating moiety ($A^c$ or $A^1$, $A^2$, $A^3$, $A^4$, $A^5$, and $A^6$) comprises a modifying moiety. In some embodiments, $R^6$, $R^7$, $R^8$, $R^9$, or $R^{10}$ of a given chelating moiety ($A^c$ or $A^1$, $A^2$, $A^3$, $A^4$, $A^5$, and $A^6$) is a modifying moiety. In some embodiments, $R^6$, $R^9$, or $R^{10}$ of a given chelating moiety ($A^c$ or $A^1$, $A^2$, $A^3$, $A^4$, $A^5$, and $A^6$) comprises a modifying moiety. In some embodiments, $R^6$, $R^9$, or $R^{10}$ of a given chelating moiety ($A^c$ or $A^1$, $A^2$, $A^3$, $A^4$, $A^5$, and $A^6$) is a modifying moiety.

In some embodiments, $R^6$, $R^7$, $R^8$, $R^9$, or $R^{10}$ of a given chelating moiety ($A^c$ or $A^1$, $A^2$, $A^3$, $A^4$, $A^5$, and $A^6$) is —C(O)NR$^{17}$R$^{18}$, wherein $R^{17}$ or $R^{18}$ comprises a modifying moiety. In some embodiments, $R^6$, $R^7$, $R^8$, $R^9$, or $R^{10}$ of a given chelating moiety ($A^c$ or $A^1$, $A^2$, $A^3$, $A^4$, $A^5$, and $A^6$) is —C(O)NR$^{17}$R$^{18}$, wherein $R^{17}$ is H and $R^{18}$ comprises a modifying moiety. In some embodiments, $R^6$, $R^7$, $R^8$, $R^9$, or $R^{10}$ of a given chelating moiety ($A^c$ or $A^1$, $A^2$, $A^3$, $A^4$, $A^5$, and $A^6$) is —C(O)NR$^{17}$R$^{18}$, wherein $R^{17}$ is H and $R^{18}$ is a modifying moiety. In some embodiments, $R^6$, $R^9$, or $R^{10}$ of a given chelating moiety ($A^c$ or $A^1$, $A^2$, $A^3$, $A^4$, $A^5$, and $A^6$) is —C(O)NR$^{17}$R$^{18}$, wherein $R^{17}$ is H and $R^{18}$ is a modifying moiety. In some embodiments, $R^6$, $R^9$, or $R^{10}$ of a given chelating moiety ($A^c$ or $A^1$, $A^2$, $A^3$, $A^4$, $A^5$, and $A^6$) is —C(O)NR$^{17}$R$^{18}$, wherein $R^{17}$ is H and $R^{18}$ is 2-methoxyethyl.

In some embodiments, $R^6$, $R^7$, $R^8$, $R^9$, or $R^{10}$ of a given chelating moiety ($A^c$ or $A^1$, $A^2$, $A^3$, $A^4$, $A^5$, and $A^6$) is —CH$_2$C(O)NR$^{17}$R$^{18}$, wherein $R^{17}$ or $R^{18}$ comprises a modifying moiety. In some embodiments, $R^6$, $R^7$, $R^8$, $R^9$, or $R^{10}$ of a given chelating moiety ($A^c$ or $A^1$, $A^2$, $A^3$, $A^4$, $A^5$, and $A^6$) is —CH$_2$C(O)NR$^{17}$R$^{18}$, wherein $R^{17}$ is H and $R^{18}$ comprises a modifying moiety. In some embodiments, $R^6$, $R^7$, $R^8$, $R^9$, or $R^{10}$ of a given chelating moiety ($A^c$ or $A^1$, $A^2$, $A^3$, $A^4$, $A^5$, and $A^6$) is —CH$_2$C(O)NR$^{17}$R$^{18}$, wherein $R^{17}$ is H and $R^{18}$ is a modifying moiety. In some embodiments, $R^6$, $R^9$, or $R^{10}$ of a given chelating moiety ($A^c$ or $A^1$, $A^2$, $A^3$, $A^4$, $A^5$, and $A^6$) is —CH$_2$C(O)NR$^{17}$R$^{18}$, wherein $R^{17}$ is H and $R^{18}$ is a modifying moiety. In some embodiments, $R^6$, $R^9$, or $R^{10}$ of a given chelating moiety ($A^c$ or $A^1$, $A^2$, $A^3$, $A^4$, $A^5$, and $A^6$) is —CH$_2$C(O)NR$^{17}$R$^{18}$, wherein $R^{17}$ is H and $R^{18}$ is 2-methoxyethyl.

In some embodiments, when $A^c$ has a structure according to formula (I) or (1), $A^c$ is attached to $L^4$ through $R^6$, and $R^{10}$ comprises a modifying moiety. In some embodiments, when $A^c$ has a structure according to formula (I) or (1), $A^c$ is attached to $L^4$ through $R^{10}$, and $R^6$ comprises a modifying moiety. In some embodiments, when $A^c$ has a structure according to formula (II), (III), (2a), (2b), (3), (4), or (5), A is attached to $L^4$ through $R^6$, and $R^9$ comprises a modifying moiety. In some embodiments, when A has a structure according to formula (II), (III), (2a), (2b), (3), (4), or (5), $A^c$ is attached to $L^4$ through $R^9$, and $R^6$ comprises a modifying moiety.

In some embodiments, when $A^1$ has a structure according to formula (I) or (1), $A^1$ is attached to $L^{A1}$ through $R^6$, and $R^{10}$ comprises a modifying moiety. In some embodiments, when $A^1$ has a structure according to formula (I) or (1), $A^1$ is attached to $L^{A1}$ through $R^{10}$, and $R^6$ comprises a modifying moiety. In some embodiments, when $A^1$ has a structure according to formula (II), (III), (2a), (2b), (3), (4), or (5), $A^1$ is attached to $L^{A1}$ through $R^6$, and $R^9$ comprises a modifying moiety. In some embodiments, when $A^1$ has a structure according to formula (II), (III), (2a), (2b), (3), (4), or (5), $A^1$ is attached to $L^{A1}$ through $R^9$, and $R^6$ comprises a modifying moiety.

In some embodiments, when $A^2$ has a structure according to formula (I) or (1), $A^2$ is attached to $L^{A2}$ through $R^6$, and $R^{10}$ comprises a modifying moiety. In some embodiments, when $A^2$ has a structure according to formula (I) or (1), $A^2$ is attached to $L^{A2}$ through $R^{10}$, and $R^6$ comprises a modifying moiety. In some embodiments, when $A^2$ has a structure according to formula (II), (III), (2a), (2b), (3), (4), or (5), $A^2$ is attached to $L^{A2}$ through $R^6$, and $R^9$ comprises a modifying moiety. In some embodiments, when $A^2$ has a structure according to formula (II), (III), (2a), (2b), (3), (4), or (5), $A^2$ is attached to $L^{A2}$ through $R^9$, and $R^6$ comprises a modifying moiety.

In some embodiments, when $A^3$ has a structure according to formula (I) or (1), $A^3$ is attached to $L^{A3}$ through $R^6$, and $R^{10}$ comprises a modifying moiety. In some embodiments, when $A^3$ has a structure according to formula (I) or (1), $A^3$ is attached to $L^{A3}$ through $R^{10}$, and $R^6$ comprises a modifying moiety. In some embodiments, when $A^3$ has a structure according to formula (II), (III), (2a), (2b), (3), (4), or (5), $A^3$ is attached to $L^{A3}$ through $R^6$, and $R^9$ comprises a modifying moiety. In some embodiments, when $A^3$ has a structure according to formula (II), (III), (2a), (2b), (3), (4), or (5), $A^3$ is attached to $L^{A3}$ through $R^9$, and $R^6$ comprises a modifying moiety.

In some embodiments, when $A^4$ has a structure according to formula (I) or (1), $A^4$ is attached to $L^{A4}$ through $R^6$, and $R^{10}$ comprises a modifying moiety. In some embodiments, when $A^4$ has a structure according to formula (I) or (1), $A^4$ is attached to $L^{44}$ through $R^{10}$, and $R^6$ comprises a modifying moiety. In some embodiments, when $A^4$ has a structure according to formula (II), (III), (2a), (2b), (3), (4), or (5), $A^4$ is attached to $L^{44}$ through $R^6$, and $R^9$ comprises a modifying moiety. In some embodiments, when $A^4$ has a structure according to formula (II), (III), (2a), (2b), (3), (4), or (5), $A^4$ is attached to $L^{44}$ through $R^9$, and $R^6$ comprises a modifying moiety.

In some embodiments, when $A^5$ has a structure according to formula (I) or (1), $A^5$ is attached to $L^{45}$ through $R^6$, and $R^{10}$ comprises a modifying moiety. In some embodiments, when $A^5$ has a structure according to formula (I) or (1), $A^5$ is attached to $L^{45}$ through $R^{10}$, and $R^6$ comprises a modifying moiety. In some embodiments, when $A^5$ has a structure according to formula (II), (III), (2a), (2b), (3), (4), or (5), $A^5$ is attached to $L^{45}$ through $R^6$, and $R^9$ comprises a modifying moiety. In some embodiments, when $A^5$ has a structure according to formula (II), (III), (2a), (2b), (3), (4), or (5), $A^5$ is attached to $L^{45}$ through $R^9$, and $R^6$ comprises a modifying moiety.

In some embodiments, when $A^6$ has a structure according to formula (I) or (1), $A^6$ is attached to $L^{46}$ through $R^6$, and $R^{10}$ comprises a modifying moiety. In some embodiments, when $A^6$ has a structure according to formula (I) or (1), $A^6$ is attached to $L^{46}$ through $R^{10}$, and $R^6$ comprises a modifying moiety. In some embodiments, when $A^6$ has a structure according to formula (II), (III), (2a), (2b), (3), (4), or (5), $A^6$ is attached to $L^{46}$ through $R^6$, and $R^9$ comprises a modifying moiety. In some embodiments, when $A^6$ has a structure according to formula (II), (III), (2a), (2b), (3), (4), or (5), $A^6$ is attached to $L^{46}$ through $R^9$, and $R^6$ comprises a modifying moiety.

2.1.2. Linker to Functional/Targeting Moiety

A "linker", "linking member", or "linking moiety" as used herein is a moiety that joins or potentially joins, covalently or noncovalently, a first moiety to a second moiety. In particular, a linker attaches or could potentially attach a ligand described herein to another molecule, such as a targeting moiety. In some embodiments, a linker attaches or could potentially attach a ligand described herein to a solid support. A linker comprising a reactive functional group that can be further reacted with a reactive functional group on a structure of interest in order to attach the structure of interest to the linker is referred to as a "functionalized linker". In exemplary embodiments, a linker is a functionalized linker. In exemplary embodiments, a ligand comprises one or more functionalized linkers. In some embodiments, a linker comprises a targeting moiety. In some embodiments, a linker to a targeting moiety comprises a bond to the targeting moiety.

A linker can be any useful structure for that joins a ligand to a reactive functional group or a targeting moiety, such as an antibody. Examples of a linker include 0-order linkers (i.e., a bond), substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Further exemplary linkers include substituted or unsubstituted ($C_1$, $C_2$, $C_3$, $C_4$, $C_5$, $C_6$, $C_7$, $C_8$, $C_9$ or $C_{10}$) alkyl, substituted or unsubstituted heteroalkyl, —C(O)NR'—, —C(O)O—, —C(O)S—, and —C(O)CR'R", wherein R' and R" are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, a linker includes at least one heteroatom. Exemplary linkers also include —C(O)NH—, —C(O), —NH—, —S—, —O—, and the like. In an exemplary embodiment, a linker is a heteroalkyl substituted with a reactive functional group.

Reactive Functional Groups

In one embodiment, a linker comprises a reactive functional group (or a "reactive functional moiety", used synonymously), which can be further reacted to covalently attach the linker to a targeting moiety. Reactive functional groups and classes of reactions useful in practicing the present invention are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in March, Advanced Organic Chemistry (3rd Ed., John Wiley & Sons, New York, 1985); Hermanson, Bioconjugate Techniques (Academic Press, San Diego, 1996); and Feeney et al., Modification of Proteins, Advances in Chemistry Series, Vol. 198 (American Chemical Society, Washington, D.C., 1982).

In some embodiments, a reactive functional group refers to a group selected from olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds., Organic Functional Group Preparations, (Academic Press, San Diego, 1989)).

A reactive functional group can be chosen according to a selected reaction partner. As an example, an activated ester, such as an NHS ester will be useful to label a protein via lysine residues. Sulfhydryl reactive groups, such as maleimides can be used to label proteins via amino acid residues carrying an SH-group (e.g., cystein). Antibodies may be labeled by first oxidizing their carbohydrate moieties (e.g., with periodate) and reacting resulting aldehyde groups with a hydrazine containing ligand.

The reactive functional groups can be chosen such that they do not participate in, or interfere with, the reactions necessary to assemble the reactive ligand. Alternatively, a reactive functional group can be protected from participating in the reaction by means of a protecting group. Those of skill in the art understand how to protect a particular functional group so that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Amines and Amino-Reactive Groups

In one embodiment, a reactive functional group is selected from an amine, (such as a primary or secondary amine), hydrazine, hydrazide and sulfonylhydrazide. Amines can, for example, be acylated, alkylated or oxidized. Useful non-limiting examples of amino-reactive groups include N-hydroxysuccinimide (NHS) esters, sulfur-NHS esters, imidoesters, isocyanates, isothiocyanates, acylhalides, arylazides, p-nitrophenyl esters, aldehydes, sulfonyl chlorides, thiazolides and carboxyl groups.

NHS esters and sulfo-NHS esters react preferentially with a primary (including aromatic) amino groups of a reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with amine groups of a molecule such as a protein. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus cross-linking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components (e.g., ε-amino group of lysine residues). Although unstable, Schiff bases are formed upon reaction of the protein amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., *Biochemistry*, 1981, 20: 4836-4842, e.g., teach how to modify a protein with carbodiimides.

Sulfhydryl and Sulfhydryl-Reactive Groups

In another embodiment, a reactive functional group is selected from a sulfhydryl group (which can be converted to disulfides) and sulfhydryl-reactive group. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

Other Reactive Functional Groups

Other exemplary reactive functional groups include:
(i) carboxyl groups and various derivatives thereof including, but not limited to, N-hydroxybenztriazole esters, acid halides, acyl imidazoles, thioesters, p-nitrophenyl esters, alkyl, alkenyl, alkynyl and aromatic esters;
(ii) hydroxyl groups, which can be converted to esters, ethers, aldehydes, etc.;
(iii) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(iv) dienophile groups, which are capable of participating in Diels-Alder reactions such as, for example, maleimido groups;
(v) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(vi) alkenes, which can undergo, for example, cycloadditions, acylation, Michael addition, etc;
(vii) epoxides, which can react with, for example, amines and hydroxyl groups; (ix) phosphoramidites and other standard functional groups useful in nucleic acid synthesis and
(x) any other functional group useful to form a covalent bond between the functionalized ligand and a molecular entity or a surface.

Functional Groups with Non-Specific Reactivities

In addition to the use of site-specific reactive moieties, the present invention contemplates the use of non-specific reactive groups to link a ligand to a targeting moiety. Non-specific groups include photoactivatable groups, for example.

Photoactivatable groups are ideally inert in the dark and are converted to reactive species in the presence of light. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein cross-links.

In exemplary embodiments, a linker joins a ligand to a targeting moiety. That is, in exemplary embodiments, a linker comprises a targeting moiety. In some embodiments, a ligand comprises a linker to a targeting moiety. Any linker described herein may be a linker comprising a reactive functional group that could react with a reactive functional group on a targeting moiety to join the linker to the targeting moiety. Any linker described herein may be a linker comprising a bond to a targeting moiety. The term "targeting moiety" refers to a moiety serves to target or direct the molecule to which it is attached (e.g., a ligand or a ligand complexed to a metal ion (such as a radionuclide)) to a particular location or molecule. Thus, for example, a targeting moiety may be used to target a molecule to a specific target protein or enzyme, or to a particular cellular location, to a particular cell type or to a diseased tissue. As will be appreciated by those in the art, the localization of proteins within a cell is a simple method for increasing effective concentration. For example, shuttling an imaging agent and/or therapeutic into the nucleus confines them to a smaller space thereby increasing concentration. Finally, the physiological target may simply be localized to a specific compartment, and the agents must be localized appropriately.

The targeting moiety can be a small molecule (e.g., MW<500D), which includes both non-peptides and peptides. Examples of a targeting moiety also include peptides, polypeptides (including proteins, and in particular antibodies, which includes antibody fragments), nucleic acids, oligonucleotides, carbohydrates, lipids, hormones (including proteinaceous and steroid hormones (for instance, estradiol)), growth factors, lectins, receptors, receptor ligands, cofactors and the like. Targets of a targeting moiety can include a complementary nucleic acid, a receptor, an antibody, an antigen or a lectin, for example.

In exemplary embodiments, a targeting moiety can bind to a target with high binding affinity. In other words, a targeting moiety with high binding affinity to a target has a high specificity for or specifically binds to the target. In some embodiments, a high binding affinity is given by a dissociation constant $K_d$ of about $10^{-7}$ M or less. In exemplary embodiments, a high binding affinity is given by a dissociation constant $K_d$ of about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less or about $10^{-15}$ M or less. A compound may have a high binding affinity for a target if the compound comprises a portion, such as a targeting moiety, that has a high binding affinity for the target.

In exemplary embodiments, a targeting moiety is an antibody. An "antibody" refers to a protein comprising one or more polypeptides substantially encoded by all or part of the recognized immunoglobulin genes. The recognized immunoglobulin genes, for example in humans, include the kappa (κ), lambda (λ) and heavy chain genetic loci, which together compose the myriad variable region genes, and the constant region genes mu (μ), delta (δ), gamma (γ), epsilon (ε) and alpha (α), which encode the IgM, IgD, IgG, IgE, and IgA isotypes respectively. Antibody herein is meant to include full length antibodies and antibody fragments, and may refer to a natural antibody from any organism, an engineered antibody or an antibody generated recombinantly for experimental, therapeutic or other purposes as further defined below. Antibody fragments include Fab, Fab', F(ab')$_2$, Fv, scFv or other antigen-binding subsequences of antibodies and can include those produced by the modification of whole antibodies or those synthesized de novo using recombinant DNA technologies. The term "antibody" refers to both monoclonal and polyclonal antibodies. Antibodies can be antagonists, agonists, neutralizing, inhibitory or stimulatory.

While a targeting moiety may be appended to a ligand in order to localize the compound to a specific region in an animal, certain ligands have a natural affinity for cells, tissue, organs or some other part of the animal. For example, a ligand disclosed herein might have a natural or intrinsic affinity for bone. Thus, in some embodiments, a ligand does not comprise a targeting moiety or a linker to a targeting moiety. A ligand lacking a targeting moiety can be used in any method that does not require specific targeting.

In some embodiments, a ligand comprises a linker to a solid support. That is, any linker described herein may be a linker comprising a reactive functional group that could react with a reactive functional group on a solid support to join the linker to the solid support. Any linker described herein may be a linker comprising a bond to a solid support. A "solid support" is any material that can be modified to contain discrete individual sites suitable for the attachment or association of a ligand. Suitable substrates include biodegradable beads, non-biodegradable beads, silica beads, magnetic beads, latex beads, glass beads, quartz beads, metal beads, gold beads, mica beads, plastic beads, ceramic beads, or combinations thereof. Of particular use are biocompatible polymers, including biodegradable polymers that are slowly removed from the system by enzymatic degradation. Example biodegradable materials include starch, cross-linked starch, poly(ethylene glycol), polyvinylpyrrolidine, polylactides (PLA), polyglycolides (PGA), poly(lactide-co-glycolides) (PLGA), polyanhydrides, polyorthoesters, poly(DTH iminocarbonate), poly(bisphenol A iminocarbonate), polycyanoacrylate, polyphosphazene, mixtures thereof and combinations thereof. Other suitable substances for forming the particles exist and can be used. In some embodiments, a solid support is a bead comprising a cross-linked starch, for example, cross-linked potato starch. Beads made from starch are completely biodegradable in the body, typically by serum amylase, a naturally occurring enzyme found in the body. In these embodiments, the ligand optionally further comprises a targeting moiety or a linker to a targeting moiety. In cases where a ligand that is attached to a solid support does not comprise a targeting moiety, the ligand can be localized directly by the practitioner, for example, by direct surgical implantation.

In some embodiments, a linker has the structure -$L^{11}$-X, wherein $L^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and X is selected from a reactive functional group, a protected functional group, or a targeting moiety.

In some embodiments, $L^{11}$ is selected from substituted or unsubstituted alkyl and substituted or unsubstituted heteroalkyl. In some embodiments, $L^{11}$ is heteroalkyl. In some embodiments, $L^{11}$ is ($C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ or $C_{20}$) alkyl in which 1, 2 or 3 atoms are replaced with a heteroatom, such as nitrogen or oxygen. In some embodiments, $L^{11}$ comprises a modifying moiety.

In some embodiments, X is selected from —$NH_2$, —C(O)OH, alkyl ester (e.g., methyl ester), N-hydroxysuccinimide (NHS) ester, sulfo-NHS ester, isothiocyanate, and maleimide. In some embodiments, X is selected from —$NH_2$ and —C(O)OH.

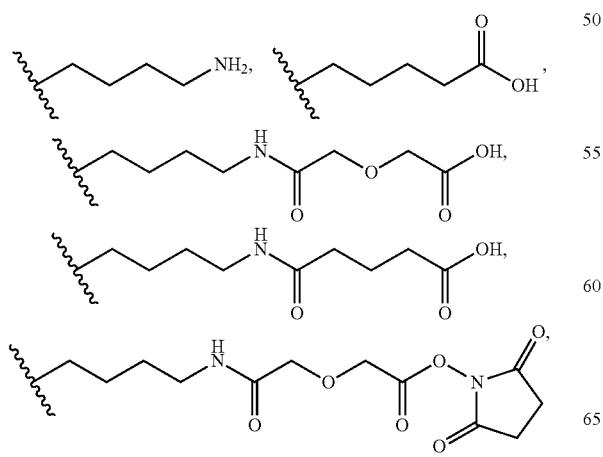

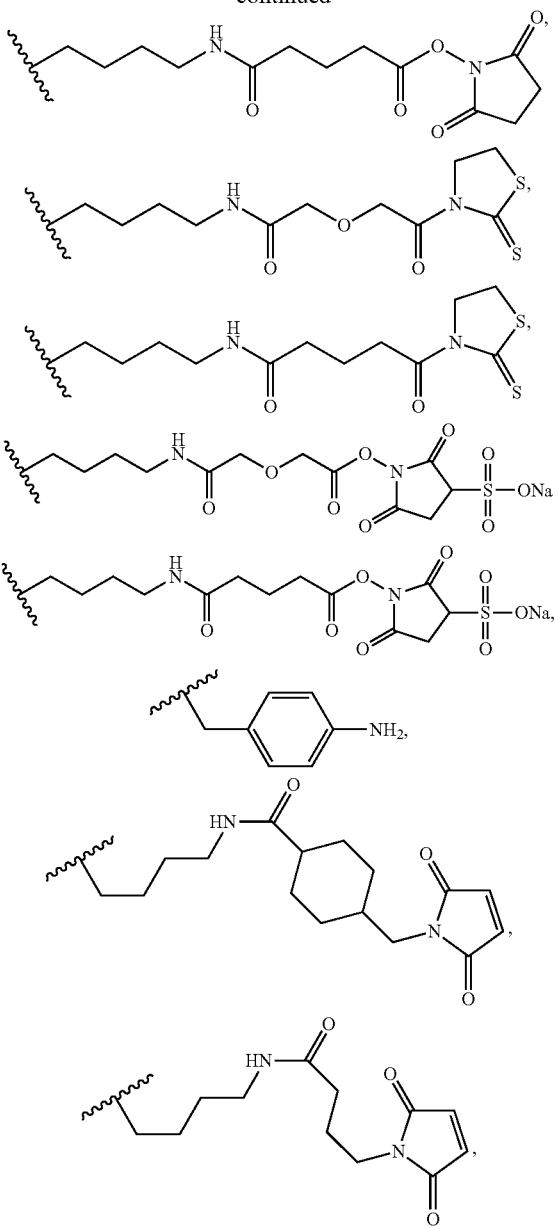

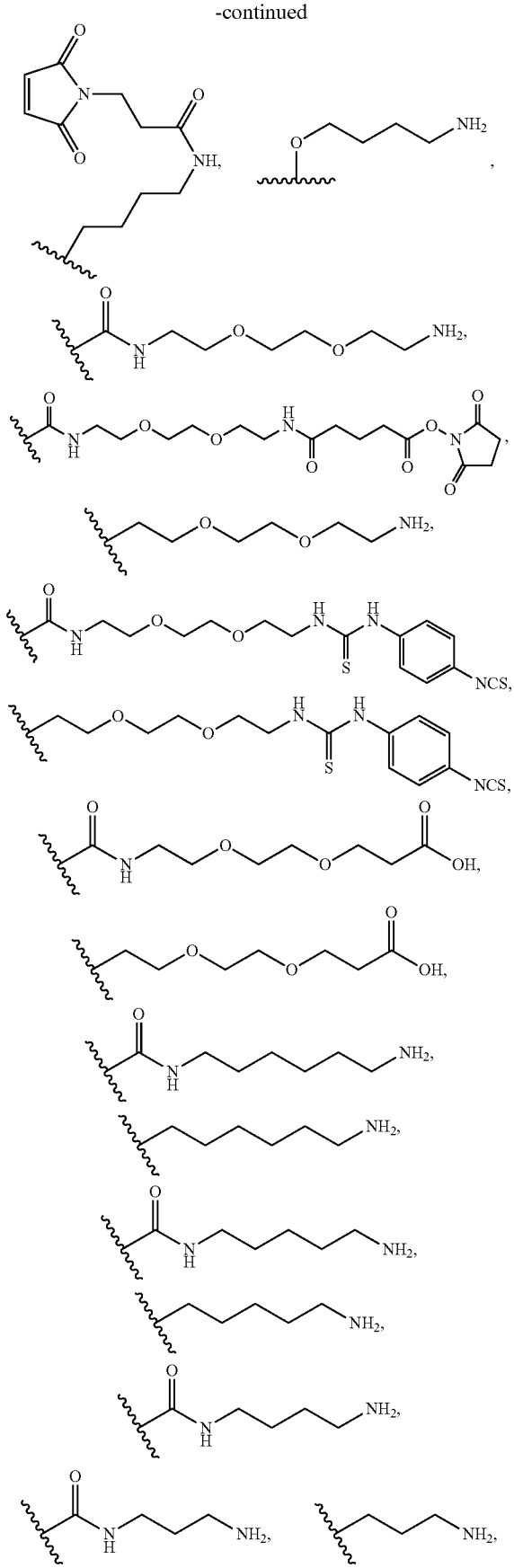
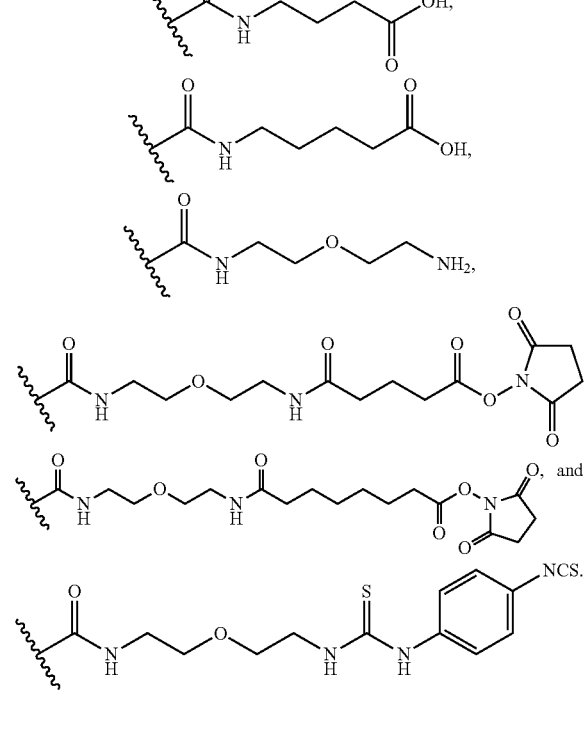

In some embodiments, a linker has the structure:

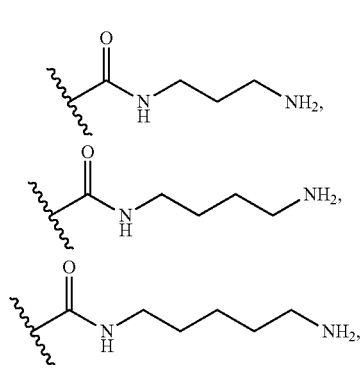

wherein $R^L$ is selected from substituted or unsubstituted alkyl, and substituted or unsubstituted heteroalkyl; and X is as defined herein. In some embodiments, $R^L$ is a substituted or unsubstituted alkoxyalkyl. In some embodiments, $R^L$ is a substituted or unsubstituted monoether. In some embodiments, $R^L$ is a substituted or unsubstituted polyether. In some embodiments, the polyether has from 2 to 10 (i.e., 2, 3, 4, 5, 6, 7, 8, 9, or 10) ether groups. In some embodiments, $R^L$ comprises a modifying moiety.

In some embodiments, a linker has a structure selected from:

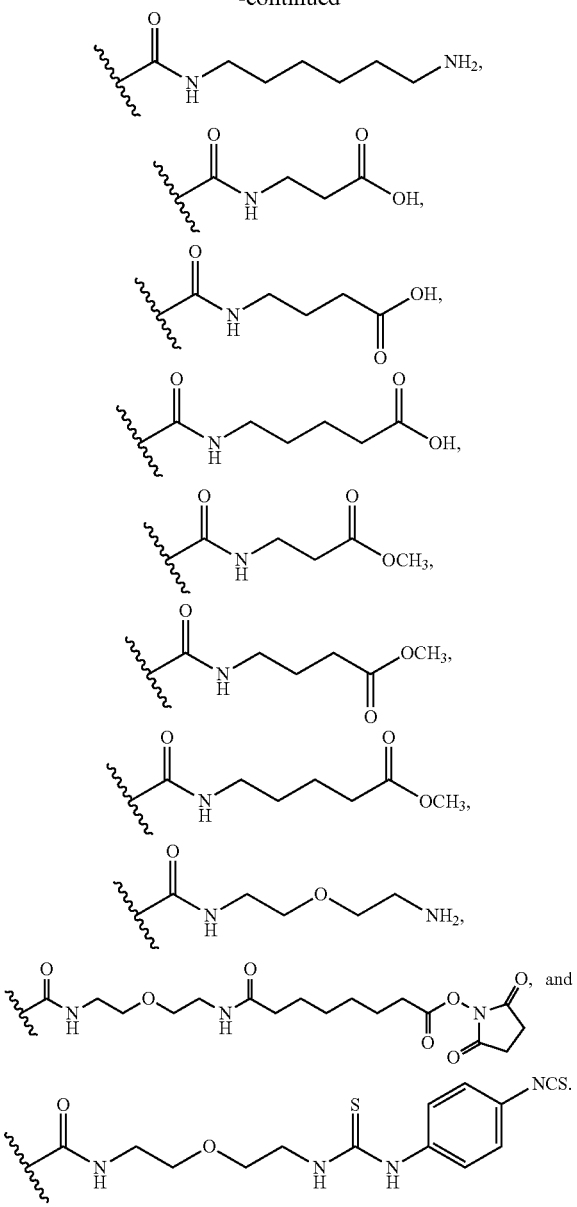

In some embodiments, a linker has a structure selected from:

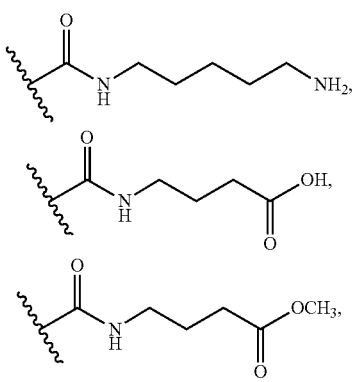

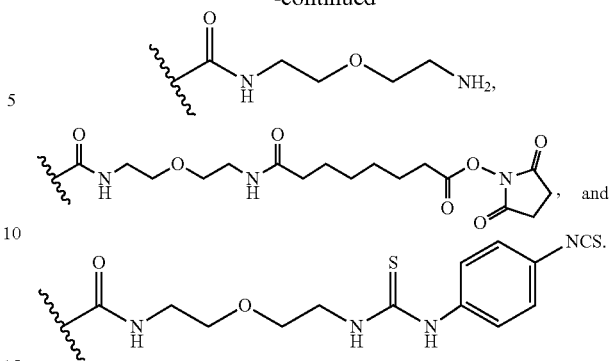

In exemplary embodiments, X is a targeting moiety.

In exemplary embodiments, a linker is a linker to a targeting moiety. In some embodiments, the targeting moiety is selected from a polypeptide, a nucleic acid, a lipid, a polysaccharide, a small molecule, a cofactor and a hormone. In exemplary embodiments, the targeting moiety is an antibody or antibody fragment.

In a linker with multiple reactive functional groups, a particular functional group can be chosen such that it does not participate in, or interfere with, the reaction controlling the attachment of the functionalized spacer component to another ligand component. Alternatively, the reactive functional group can be protected from participating in the reaction by the presence of a protecting group. Those of skill in the art understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

2.1.3. Modifying Moiety

In some embodiments, one or more of $Y^1$, $Y^2$, L, and $A^c$ comprise(s) a modifying moiety. In some embodiments, one or more of $Y^1$, $Y^2$, $L^{s1}$, $L^{s2}$, $L^{s3}$, $L^{s4}$, $L^{s5}$, $A^1$, $A^2$, $A^3$, $A^4$, $A^5$, and $A^6$ comprise(s) a modifying moiety. In some embodiments, a linker comprises a modifying moiety. Each of the modifying moieties can be the same or different. The modifying moiety modifies various properties of the ligand and/or a complex formed between the ligand and a metal ion, such as solubility, charge, or affinity. In some embodiments, the modifying moiety does not interact with the metal when the ligand is complexed to a metal. In some embodiments, the modifying moiety is a solubilizing group, a hormone-derived moiety, a prodrug moiety (for example, with a cleavable moiety), an oligonucleotide, ssDNA, dsDNA, RNA, or a peptide. The solubilizing group improves solubility of the ligand and/or a complex formed between the ligand and a metal ion in aqueous media. In some embodiments, the hormone (of the hormone-derived moiety) is a steroid. In some embodiments, the steroid is estradiol. In some embodiments, the modifying moiety is an estradiol-derived moiety. Peptides of a hydrophilic and hydrophobic nature by virtue of their amino acid composition may be used to tune solubility of the ligand and/or a complex formed between the ligand and a metal ion.

In some embodiments, the modifying moiety is substituted or unsubstituted heteroalkyl. In some embodiments, the modifying moiety is a substituted or unsubstituted alkoxyalkyl. In some embodiments, the modifying moiety is a substituted or unsubstituted monoether. In some embodiments, the modifying moiety is a substituted or unsubstituted polyether. In some embodiments, the modifying moiety comprises an estradiol-derived moiety. In some embodiments, the modifying moiety is a polyether substituted with an estradiol-derived moiety.

In some embodiments, the modifying moiety is selected from:

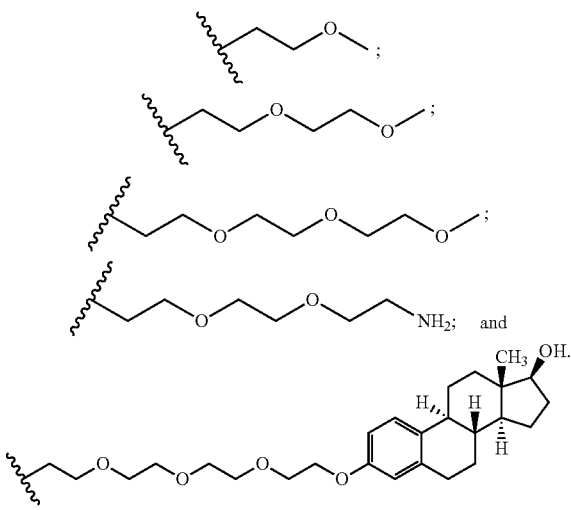

In some embodiments, the modifying moiety is a peptide. In some embodiments, the modifying moiety is

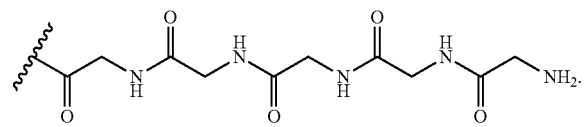 [SMILES: *C(=O)CNC(=O)CNC(=O)CNC(=O)CNC(=O)CN]

In some embodiments, the modifying moiety comprises an oligunucleotide.

2.1.4. Exemplary Ligands

In some embodiments, the invention provides a ligand having the structure:

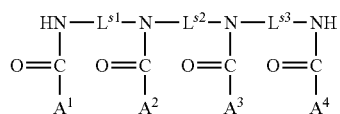

wherein $L^{s1}$, $L^{s2}$, and $L^{s3}$ are independently selected from substituted or unsubstituted alkyl, and substituted or unsubstituted heteroalkyl; $A^1$, $A^2$, $A^3$, and $A^4$ are members independently selected from:

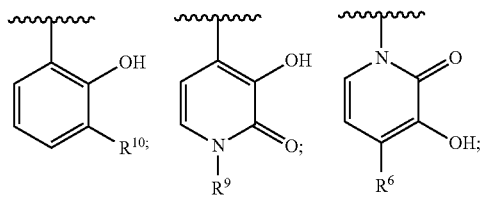

-continued

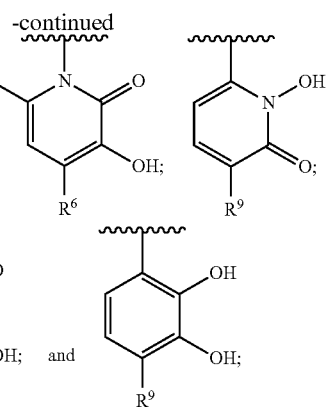

wherein $R^6$, $R^9$, and $R^{10}$ are as defined herein. In some embodiments, the ligand is covalently modified with at least one linker. In some embodiments, one of $L^{s1}$, $L^{s2}$, and $L^{s3}$ is substituted with a linker. In some embodiments, $L^{s2}$ is substituted with a linker. In some embodiments, $L^{s1}$ is substituted with a linker. In some embodiments, $L^{s3}$ is substituted with a linker. In some embodiments, $L^{s1}$ and $L^{s3}$ are each independently selected from unsubstituted $C_3$ and $C_4$ alkyl; and $L^{s2}$ is $C_3$ or $C_4$ alkyl substituted with a linker. In some embodiments, $L^{s2}$ and $L^{s3}$ are each independently selected from unsubstituted $C_3$ and $C_4$ alkyl; and $L^{s1}$ is $C_3$ or $C_4$ alkyl substituted with a linker. In some embodiments, $L^{s1}$ and $L^{s2}$ are each independently selected from unsubstituted $C_3$ and $C_4$ alkyl; and $L^{s3}$ is $C_3$ or $C_4$ alkyl substituted with a linker.

In some embodiments, the invention provides a ligand having the structure:

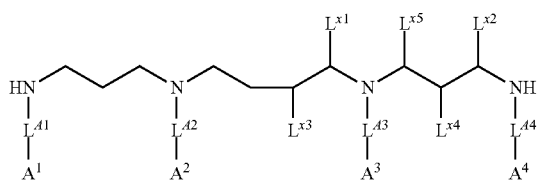

wherein $L^{x1}$, $L^{x2}$, $L^{x3}$, $L^{x4}$, and $L^{x5}$ are independently selected from H and a linker. $L^{A1}$, $L^{A2}$, $L^{A3}$, $L^{A4}$, $A^1$, $A^2$, $A^3$, and $A^4$ are as defined herein. In some embodiments, one of $L^{x1}$, $L^{x2}$, $L^{x3}$, $L^{x4}$, and $L^{x5}$ is a linker. In some embodiments, $L^{x1}$ is a linker; and $L^{x2}$, $L^{x3}$, $L^{x4}$, and $L^{x5}$ are H. In some embodiments, $L^{x2}$ is a linker; and $L^{x1}$, $L^{x3}$, $L^{x4}$, and $L^{x5}$ are H. In some embodiments, the linker has the structure:

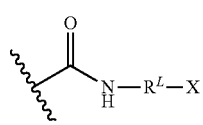

wherein $R^L$ and X are as defined herein. In some embodiments, $L^{A1}$, $L^{A2}$, $L^{A3}$, and $L^{A4}$ are independently selected from a bond, —C(O)—, —(CH$_2$)$_a$C(O)—, and —O(CH$_2$)$_a$C(O)—; wherein a is an integer selected from 1, 2, 3, 4, 5, and 6. In some embodiments, $A^1$, $A^2$, $A^3$, and $A^4$ are members independently selected from:

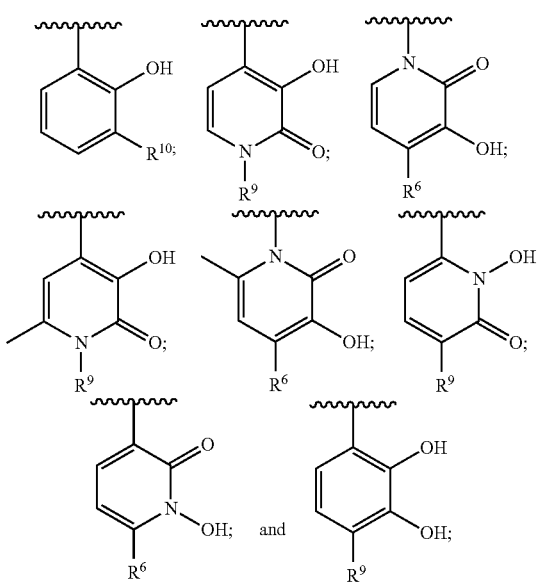

wherein R⁶, R⁹, and R¹⁰ are as defined herein. In some embodiments, R⁶, R⁹, and R¹⁰ comprise a modifying moiety.

In some embodiments, the invention provides a ligand having the structure:

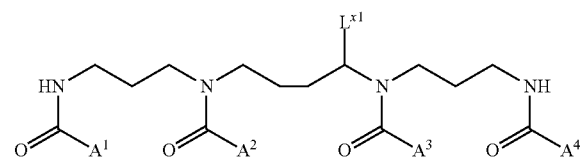

wherein
$L^{x1}$ is H or a linker; and $A^1$, $A^2$, $A^3$, and $A^4$ are members independently selected from:

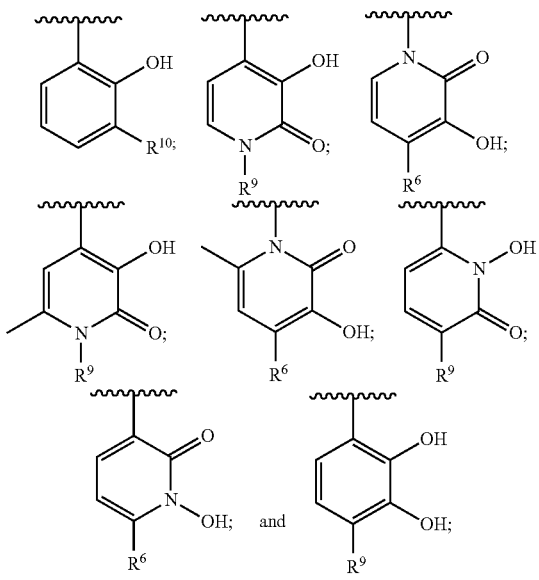

wherein R⁶, R⁹, and R¹⁰ are as defined herein. In some embodiments, $L^{x1}$ is a linker. In some embodiments, the linker has the structure:

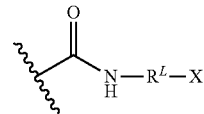

wherein $R^L$ is selected from substituted or unsubstituted alkyl, and substituted or unsubstituted heteroalkyl; and X is as defined herein. In some embodiments, R⁶, R⁹, and R¹⁰ comprise a modifying moiety.

In some embodiments, the invention provides a ligand having the structure:

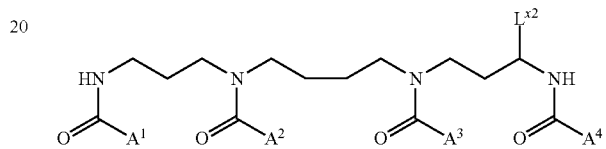

wherein $L^{x2}$ is H or a linker; and $A^1$, $A^2$, $A^3$, and $A^4$ are members independently selected from:

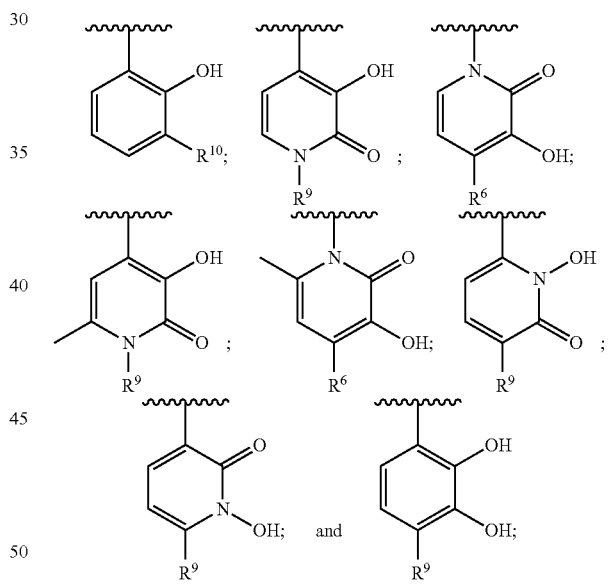

wherein R⁶, R⁹, and R¹⁰ are as defined herein. In some embodiments, $L^{x2}$ is a linker. In some embodiments, the linker has the structure:

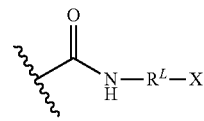

wherein $R^L$ is selected from substituted or unsubstituted alkyl, and substituted or unsubstituted heteroalkyl; and X is as defined herein. In some embodiments, R⁶, R⁹, and R¹⁰ comprise a modifying moiety.

Additional exemplary ligands are shown below:
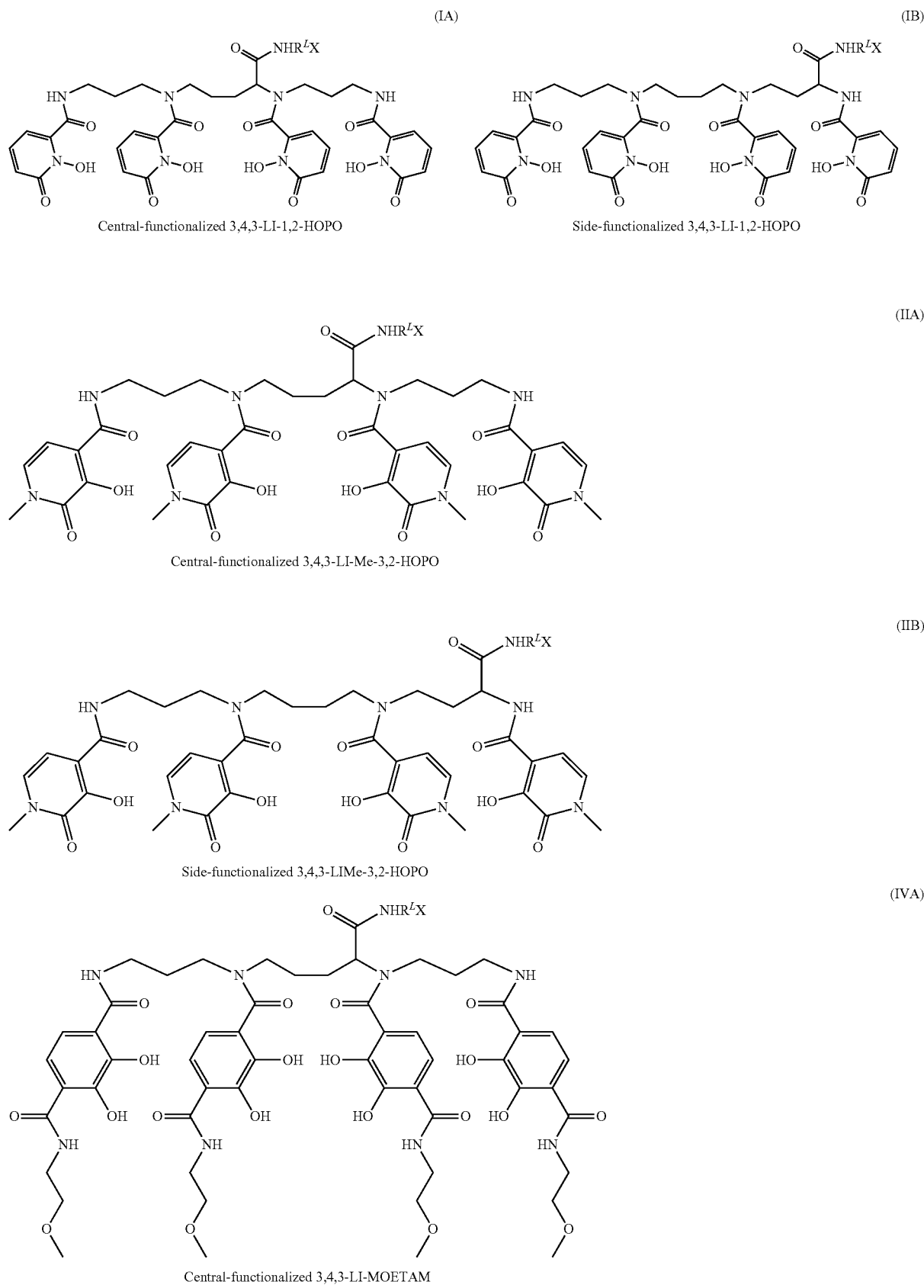

-continued
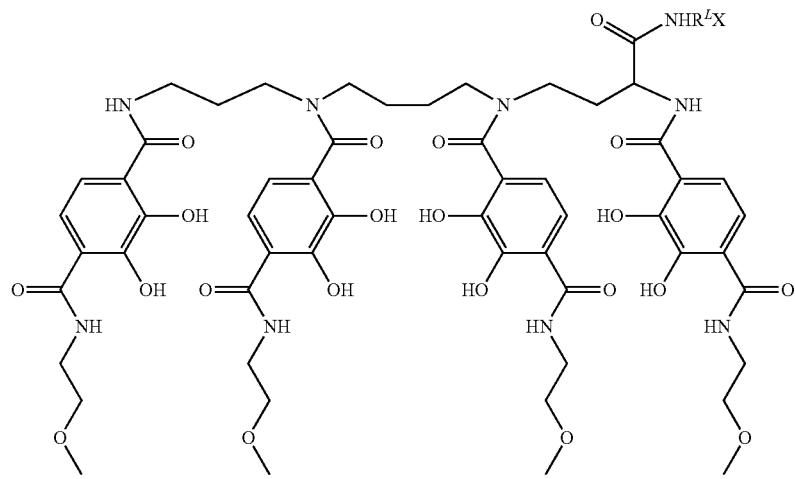
Side-functionalized 3,4,3-LI-MOETAM
(IVB)
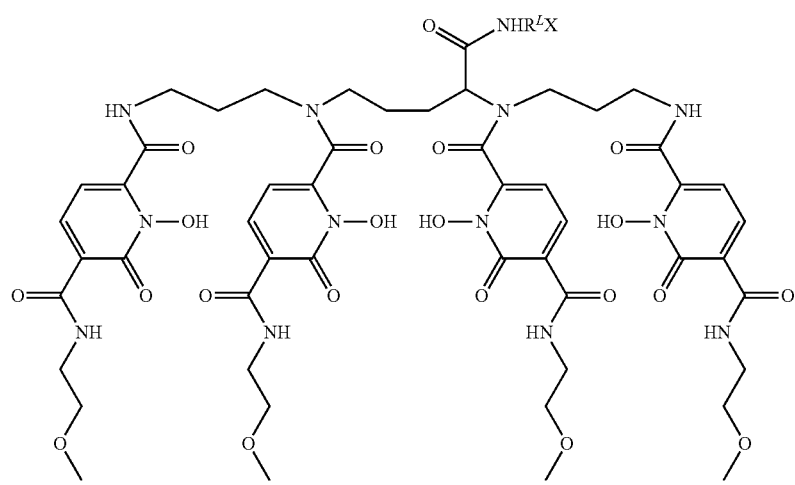
Central-functionalized 3,4,3-LI-1,2-HOPODA
(VA)
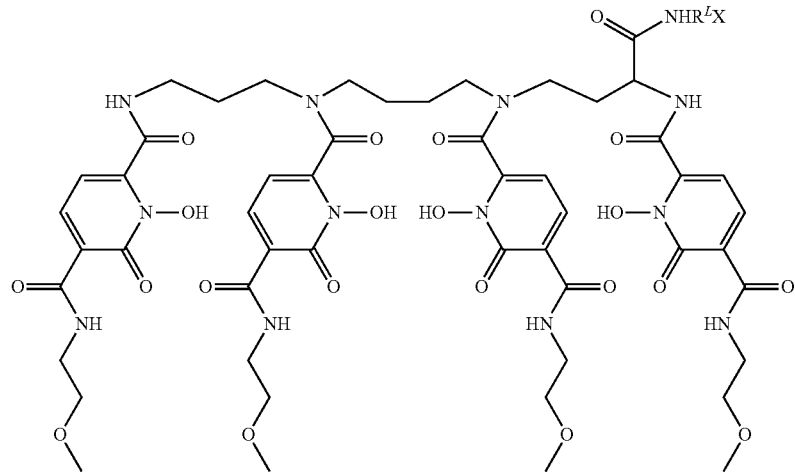
Side-functionalized 3,4,3-LI-1,2-HOPODA
(VB)

-continued
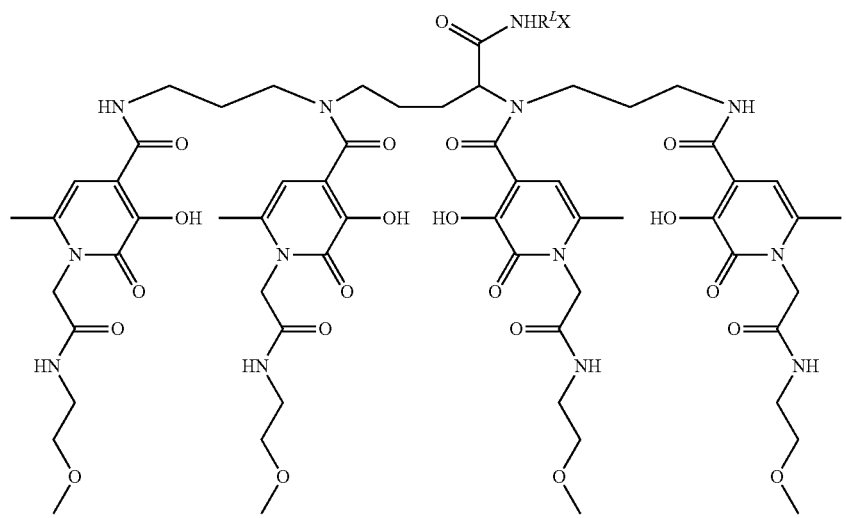
Central-functionalized 3,4,3-LI-6-Me-3,2-HOPODA
(VIA)
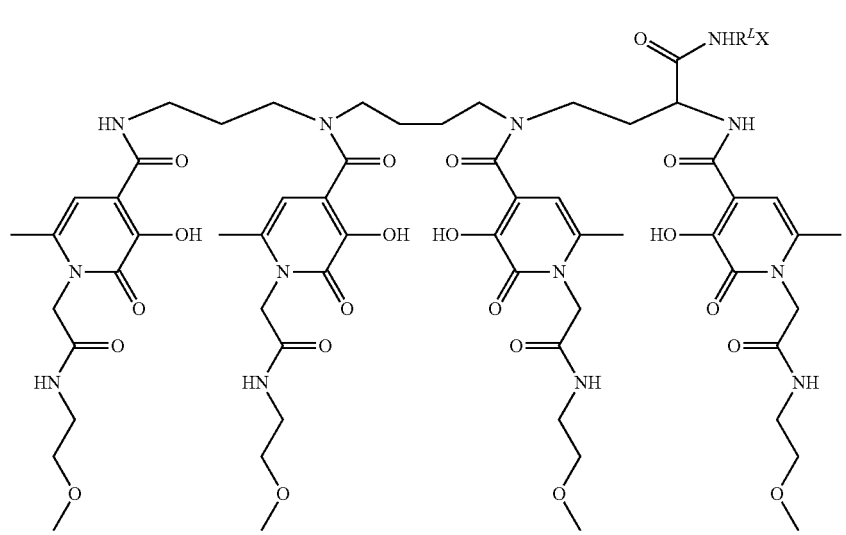
Side-functionalized 3,4,3-LI-6-Me-3,2-HOPODA
(VIB)
$R^L$ and X are as defined herein.
Additional exemplary ligands are shown below:
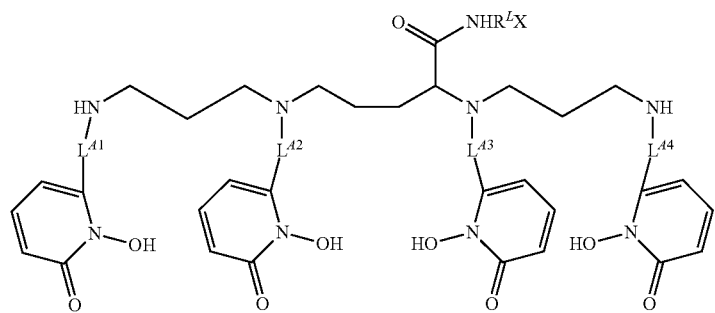
Central-functionalized 3,4,3-LIR-1,2-HOPO -continued
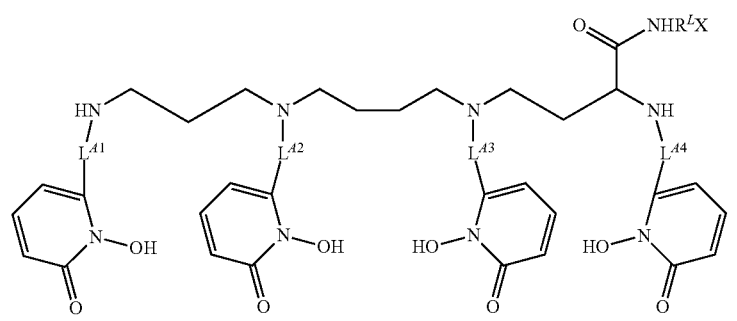
Side-functionalized 3,4,3-LIR-1,2-HOPO
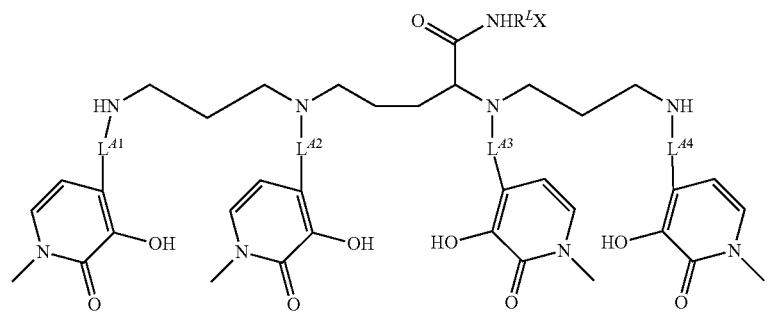
Central-functionalized 3,4,3-LIR-Me-3,2-HOPO
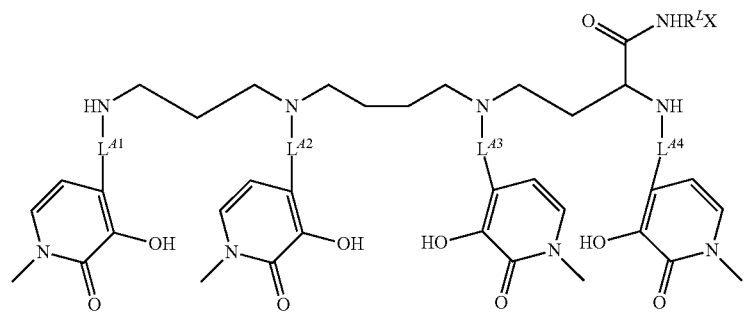
Side-functionalized 3,4,3-LIR-Me-3,2-HOPO
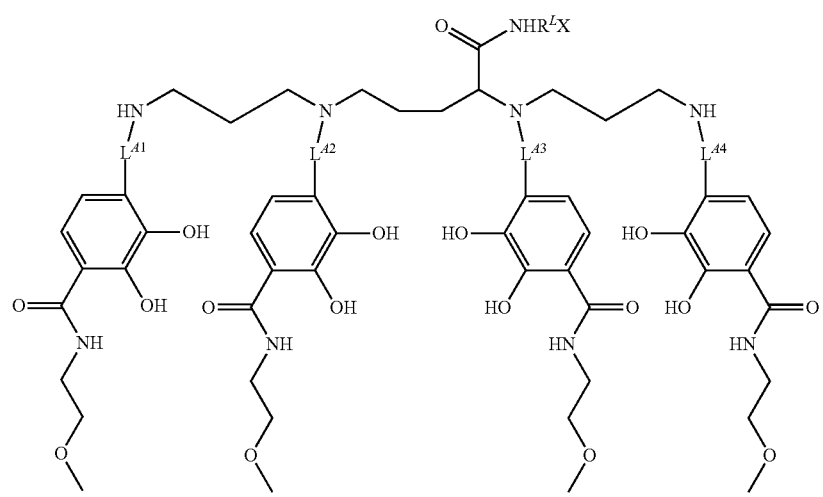
Central-functionalized 3,4,3-LIR-MOETAM

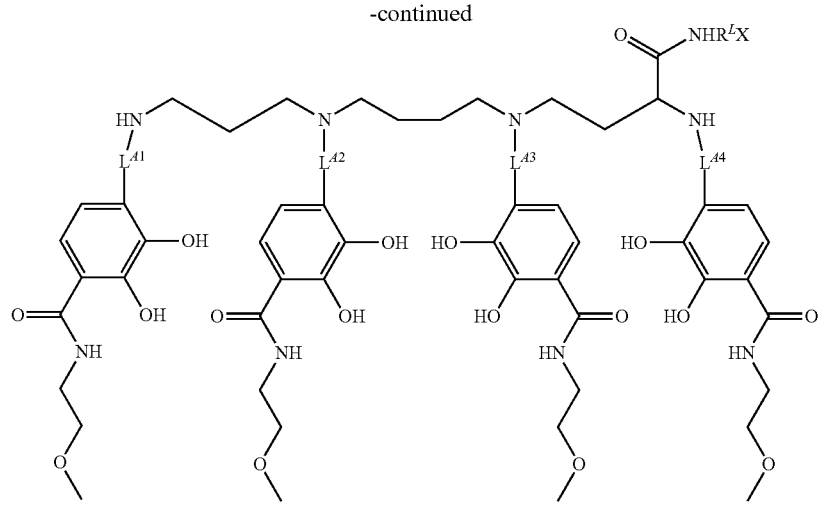
Side-functionalized 3,4,3-LIR-MOETAM
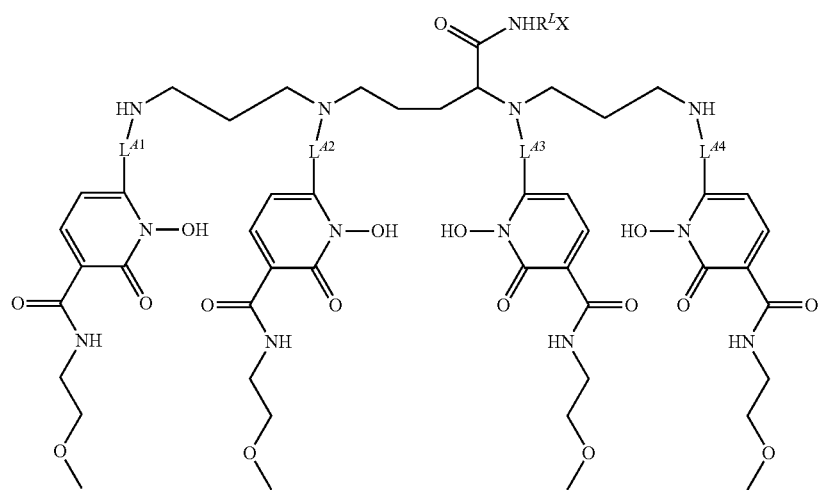
Central-functionalized 3,4,3-LIR-1,2-HOPODA
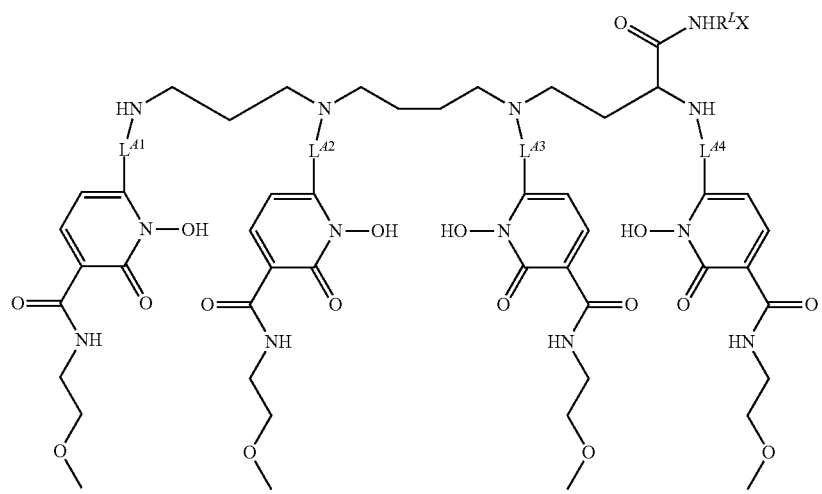
Side-functionalized 3,4,3-LIR-1,2-HOPODA $L^{A1}$, $L^{A2}$, $L^{A3}$, $L^{A4}$, $R^L$, and X are as defined herein. In some embodiments, $L^{A1}$, $L^{A2}$, $L^{A3}$, and $L^{A4}$ are independently selected from —C(O)—, —(CH$_2$)$_a$C(O)—, and —O(CH$_2$)$_a$C(O)—, wherein a is an integer selected from 1, 2, 3, 4, 5, and 6.
Additional exemplary ligands are shown below:
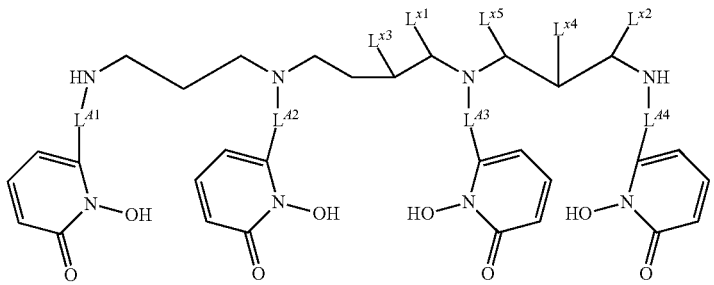
Functionalized 3,4,3-LIR-1,2,-HOPO
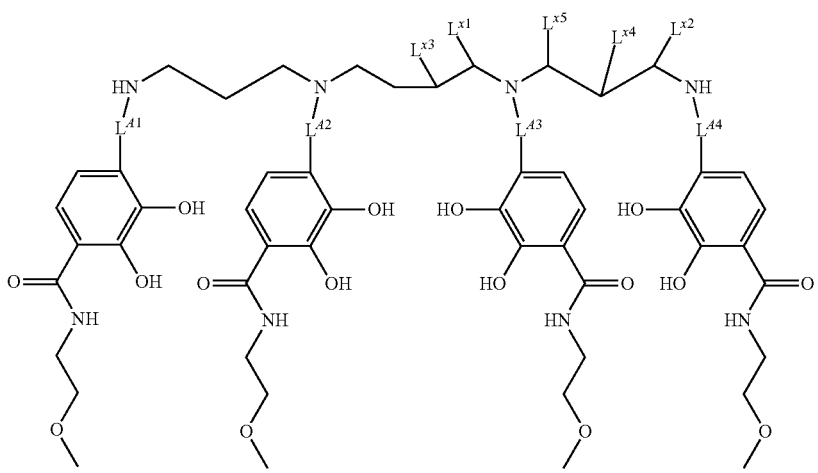
Functionalized 3,4,3-LIR-MOETAM
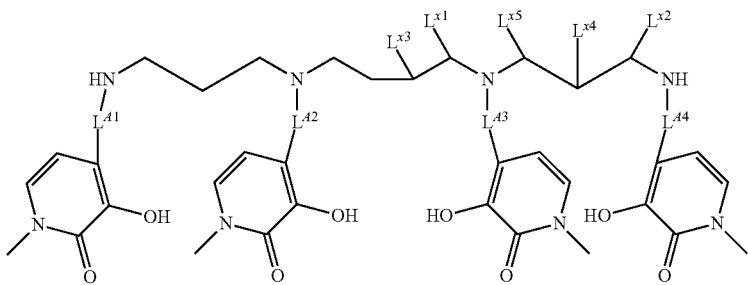
Functionalized 3,4,3-LIR-Me-3,2-HOPO

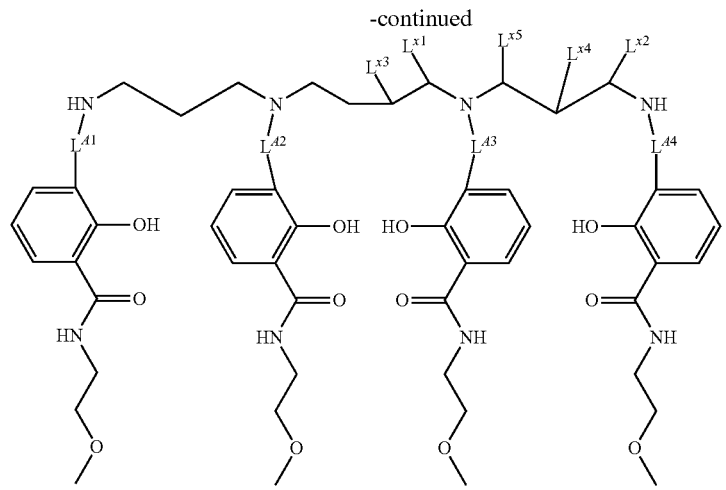

Functionalized 3,4,3-LIR-MOE-IAM $L^{x1}$, LX, $L^{x3}$, $L^{x4}$, and $L^{x5}$ are independently selected from H and a linker. $L^{A1}$, $L^{A2}$, $L^{A3}$, and $L^{A4}$ are as defined herein. In some embodiments, one of $L^{x1}$, $L^{x2}$, $L^{x3}$, $L^{x4}$, and $L^{x5}$ is a linker. In some embodiments, $L^{x1}$ is a linker; and $L^{x2}$, $L^{x3}$, $L^{x4}$, and $L^{x5}$ are H. In some embodiments, $L^{x2}$ is a linker; and $L^{x1}$, $L^{x3}$, $L^{x4}$, and $L^{x5}$ are H. In some embodiments, the linker has the structure:

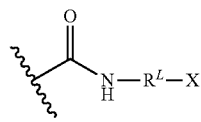

wherein $R^L$ and X are as defined herein. In some embodiments, $L^{A1}$, $L^{A2}$, $L^{A3}$, and $L^{A4}$ are independently selected from —C(O)—, —(CH$_2$)$_a$C(O)—, and —O(CH$_2$)$_a$C(O)—, wherein a is an integer selected from 1, 2, 3, 4, 5, and 6.

Additional exemplary ligands are shown below:

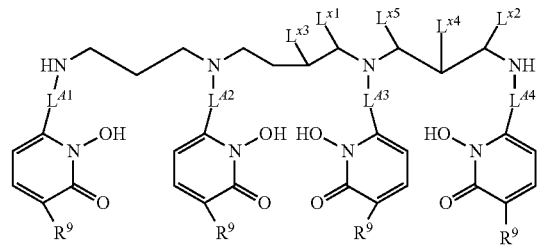

Functionalized 3,4,3-LIR-1,2-HOPO (up)

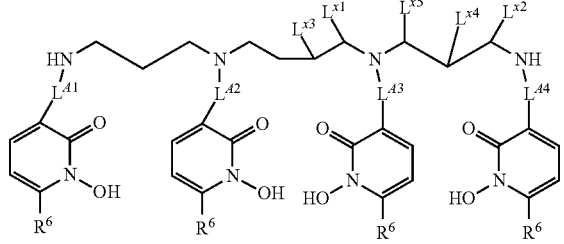

Functionalized 3,4,3-LIR-1,2-HOPO (down)

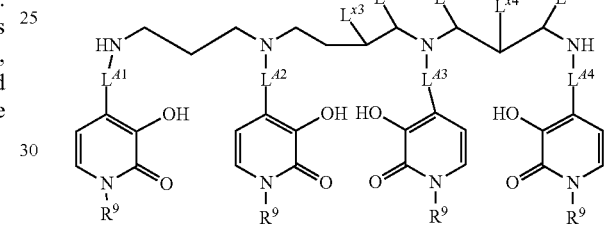

Functionalized 3,4,3-LIR-Me-3,2-HOPO (up)

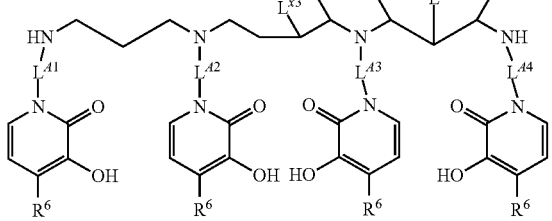

Functionalized 3,4,3-LIR-Me-3,2-HOPO (down)

$L^{x1}$, $L^{x2}$, $L^{x3}$, $L^{x4}$, and $L^{x5}$ are independently selected from H and a linker. $L^{A1}$, $L^{A2}$, $L^{A3}$, $L^{A4}$, $R^6$ and $R^9$ are as defined herein. In some embodiments, one of $L^{x1}$, $L^{x2}$, $L^{x3}$, $L^{x4}$, and $L^{x5}$ is a linker. In some embodiments, $L^{x1}$ is a linker; and $L^{x2}$, $L^{x3}$, $L^{x4}$, and $L^{x5}$ are H. In some embodiments, $L^{x2}$ is a linker; and $L^{x1}$, $L^{x3}$, $L^{x4}$, and $L^{x5}$ are H. In some embodiments, the linker has the structure:

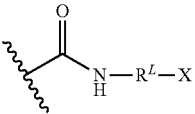

wherein $R^L$ and X are as defined herein. In some embodiments, $L^{A1}$, $L^{A2}$, $L^{A3}$, and $L^{A4}$ are independently selected from —C(O)—, —(CH$_2$)$_a$C(O)—, and —O(CH$_2$)$_a$C(O)—, wherein a is an integer selected from 1, 2, 3, 4, 5, and 6. In some embodiments, $R^6$ and $R^9$ comprise a modifying moiety.

Additional exemplary ligands are shown in the Examples.

In some embodiments, the ligand does not have the structure:

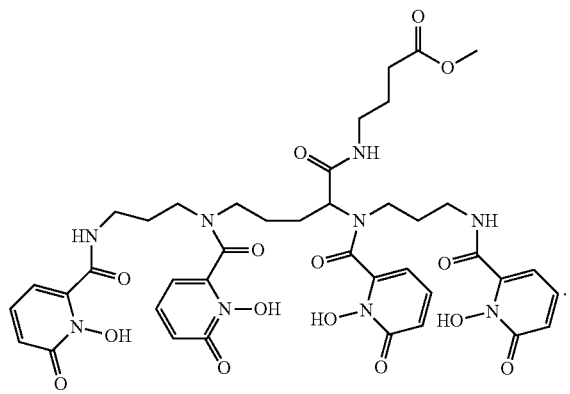

2.2. Complexes

In one aspect, the invention provides a complex of a compound (ligand) disclosed herein with a metal ion.

Any of the combinations of compounds (ligands) disclosed herein and a metal ion disclosed herein are encompassed by this disclosure and specifically provided by the invention.

In some embodiments, the complex is luminescent.

In another aspect, the invention provides a complex of a compound (ligand) disclosed herein with an element, or ion thereof, from periods 4, 5, 6 and 7 and/or from groups 13, 14, 15, 16.

2.2.1. Metals

In some embodiments, the metal is an actinide. In some embodiments, the actinide is thorium (Th). In some embodiments, the metal is a lanthanide. In some embodiments, the lanthanide is terbium (Tb). In some embodiments, the lanthanide is europium (Eu). In some embodiments, the lanthanide is dysprosium (Dy). In some embodiments, the lanthanide is lutetium (Lu). In some embodiments, the lanthanide is gadolinium (Gd). In some embodiments the metal is yttrium (Y). In some embodiments, the metal is zirconium (Zr). In some embodiments, the metal ion is yttrium(III). In some embodiments, the metal ion is europium(III). In some embodiments, the metal ion is terbium(III). In some embodiments, the metal ion is zirconium(IV). In some embodiments, the metal ion is thorium(IV). In some embodiments, the metal ion is selected from $Th^{4+}$, $Zr^{4+}$, $Eu^{3+}$, $Dy^{3+}$, $Tb^{3+}$, $Lu^{3+}$, and $Y^{3+}$. In some embodiments, the metal (ion) is a radionuclide. In some embodiments, the metal ion is $^{227}Th(IV)$. In some embodiments, the metal ion is $^{89}Zr(IV)$.

In some embodiments, the metal is $^{177}Lu$. In some embodiments, the metal is $^{166}Ho$. In some embodiments, the metal is $^{153}Sm$. In some embodiments, the metal is $^{90}Y$. In some embodiments, the metal is $^{86}Y$. In some embodiments, the metal is $^{166}Dy$. In some embodiments, the metal is $^{165}Dy$. In some embodiments, the metal is $^{169}Er$. In some embodiments, the metal is $^{175}Yb$. In some embodiments, the metal is $^{225}Ac$. In some embodiments, the metal is $^{149}Tb$. In some embodiments, the metal is $^{153}Gd$. In some embodiments, the metal is $^{230}U$.

In some embodiments, the metal is $^{111}In$. In some embodiments, the metal is $^{67}Ga$. In some embodiments, the metal is $^{67}Cu$. In some embodiments, the metal is $^{64}Cu$. In some embodiments, the metal is $^{186}Re$. In some embodiments, the metal is $^{188}Re$. In some embodiments, the metal is $^{111}Ag$. In some embodiments, the metal is $^{109}Pd$. In some embodiments, the metal is $^{212}Pb$. In some embodiments, the metal is $^{203}Pb$. In some embodiments, the metal is $^{212}Bi$. In some embodiments, the metal is $^{213}Bi$. In some embodiments, the metal is $^{195m}Pt$. In some embodiments, the metal is $^{201}Tl$. In some embodiments, the metal is $^{55}Co$. In some embodiments, the metal is $^{99m}Tc$.

In some embodiments, the complex does not have the structure:

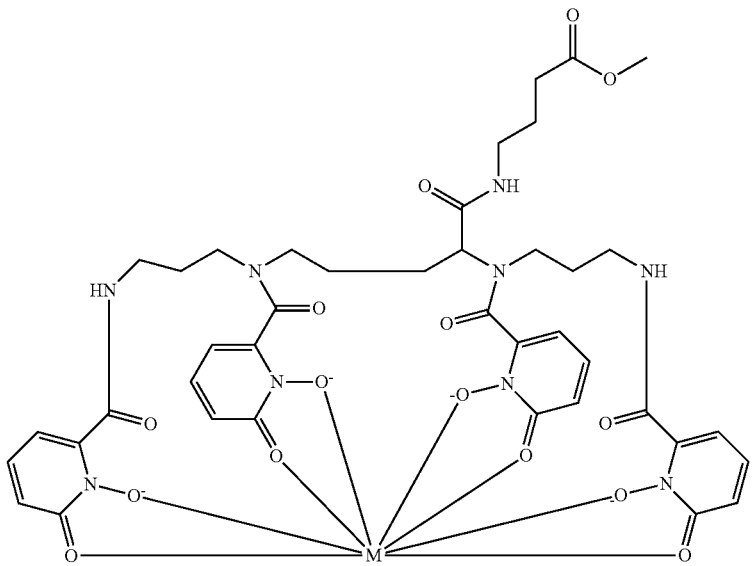

wherein M is $Th^{4+}$, $Zr^{4+}$, $Lu^{3+}$, or $Y^{3+}$.

2.2.1.1. Radionuclides

The chelating moieties disclosed herein can be used to bind metal ions, in particular, a radionuclide. The term "radionuclide" or "radioisotope" refers to a radioactive isotope or element with an unstable nucleus that tends to undergo radioactive decay. Numerous decay modes are known in the art and include alpha decay, proton emission, neutron emission, double proton emission, spontaneous fission, cluster decay, β⁻ decay, positron emission (β⁺ decay), electron capture, bound state beta decay, double beta decay, double electron capture, electron capture with positron emission, double positron emission, isomeric transition and internal conversion.

Exemplary radionuclides include alpha-emitters, which emit alpha particles during decay. In some embodiments, a radionuclide is an emitter of a gamma ray or a particle selected from an alpha particle, an electron and a positron.

In some embodiments, the radionuclide is an actinide. In some embodiments, the radionuclide is a lanthanide. In some embodiments, the radionuclide is a 3⁺ ion. In some embodiments, the radionuclide is a 4⁺ ion. In some embodiments the radionuclide is a 2⁺ ion.

Of particular use in the complexes provided herein are radionuclides selected from isotopes of U, Pu, Fe, Cu, Sm, Gd, Tb, Dy, Ho, Er, Yb, Lu, Y, Th, Zr, In, Ga, Bi, Ra, At and Ac. In some embodiments, a radionuclide is selected form radium-223, thorium-227, astatine-211, bismuth-213, Lutetium-177, and actinium-225. Other useful radioisotopes include bismuth-212, iodine-123, copper-64, iridium-192, osmium-194, rhodium-105, samarium-153, and yttrium-88, yttrium-90, and yttrium-91. In exemplary embodiments, the radionuclide is thorium, particularly selected from thorium-227 and thorium-232. In some embodiments, thorium-226 is excluded. In some embodiments, U is excluded. In some embodiments, uranium-230 is excluded. That is, in some embodiments, a radionuclide is not U, or a radionuclide is not uranium-230 or a radionuclide is not thorium-226.

²³²Th exists in nature as an α-emitter with a half life of 1.4×10¹⁰ yr. In aqueous solution, Th(IV) is the only oxidation state. Thorium(IV) ion is bigger than Pu(IV) and usually forms complexes with 9 or higher coordination number. For example, the crystal structure of both Th(IV) complexes of simple bidentate 1,2-HOPO and Me-3,2-HOPO have been determined as nine coordinated species.

Similar to other actinide ions, thorium(IV) prefers forming complexes with oxygen, especially negative oxygen donor ligands. Thorium(IV) also prefers octadentate or higher multidentate ligands:

| Ligand | Acac | NTA | HEDTA* | EDTA** | DTPA | TTHA |
|---|---|---|---|---|---|---|
| Ligand Type | Bi-dentate | Tetra- | Hexa- | Hexa- | Octa- | Deca- |
| Log $K_1$ | 7.85 | 16.9 | 18.5 | 25.3 | 30.34 | 31.9 |

*with one alcoholic oxygen and three carboxyl groups;
**with four carboxyl groups.

Other radionuclides with diagnostic and therapeutic value that can be used with the compounds disclosed herein can be found, for example, in U.S. Pat. Nos. 5,482,698 and 5,601,800; and Boswell and Brechbiel, Nuclear Medicine and Biology, 2007 October, 34(7): 757-778 and the manuscript thereof made available in PMC 2008 Oct. 1.

3. Uses

The ligands and complexes disclosed herein can be used in a wide variety of therapeutic and diagnostic settings.

In one aspect, the invention provides a method of treating a disease in an animal comprising administering a complex disclosed herein to the animal, whereby the disease is ameliorated or eliminated.

In one aspect, the invention provides a method of diagnosing a disease in an animal comprising (a) administering a complex disclosed herein to the animal and (b) detecting the presence or absence of a signal emitted by the complex. In some embodiments, the detecting step comprises obtaining an image based on the signal.

In some embodiments, the disease is cancer.

In some embodiments, the complex comprises a linker to a targeting moiety and the method further comprises localizing the complex to a targeting site in the animal by binding the targeting moiety to the targeting site.

The compounds disclosed herein are particularly well suited for the preparation of stable, pre-labeled antibodies for use in the diagnosis and treatment of cancer and other diseases. For example, antibodies expressing affinity for specific tumors or tumor-associated antigens are labeled with a diagnostic radionuclide-complexed chelate, and the labeled antibodies can be further stabilized through lyophilization. Where a chelate is used, it generally is covalently attached to the antibody. The antibodies used can be polyclonal or monoclonal, and the radionuclide-labeled antibodies can be prepared according to methods known in the art. The method of preparation will depend upon the type of radionuclide and antibody used. A stable, lyophilized, radiolabeled antibody can be reconstituted with suitable diluent at the time of intended use, thus greatly simplifying the on site preparation process. The methods of the invention can be applied to stabilize many types of pre-labeled antibodies, including, but not limited to, polyclonal and monoclonal antibodies to tumors associated with melanoma, colon cancer, breast cancer, prostate cancer, etc. Such antibodies are known in the art and are readily available.

By way of summary, in exemplary embodiments, the present invention provides:

A compound having a structure selected from:

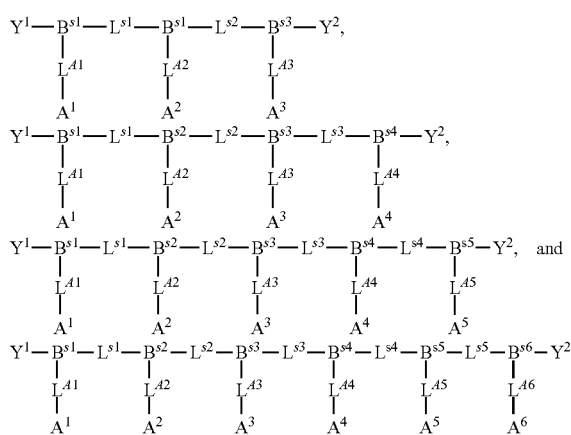

wherein the compound comprises a linker. $Y^1$ and $Y^2$ are independently selected from H, substituted or unsubstituted alkyl, and substituted or unsubstituted heteroalkyl. $B^{s1}$, $B^{s2}$, $B^{s3}$, $B^{s4}$, $B^{s5}$, and $B^{s6}$ are independently selected from N, $CR^s$, B, $SiR^s$, and P. $R^s$ is selected from H and unsubstituted $C_1$-$C_3$ alkyl. $L^{A1}$, $L^{A2}$, $L^{A3}$, $L^{A4}$, $L^{A5}$, and $L^{A6}$ are independently selected from a bond, —C(O)—, substituted or unsubstituted alkyl, and substituted or unsubstituted heteroalkyl. $L^{s1}$, $L^{s2}$, $L^{s3}$, $L^{s4}$, and $L^{s5}$ are independently selected from substituted or unsubstituted alkyl and substituted or unsubstituted heteroalkyl. $A^1$, $A^2$, $A^3$, $A^4$, $A^5$, and $A^6$ are chelating moieties having a structure independently selected from

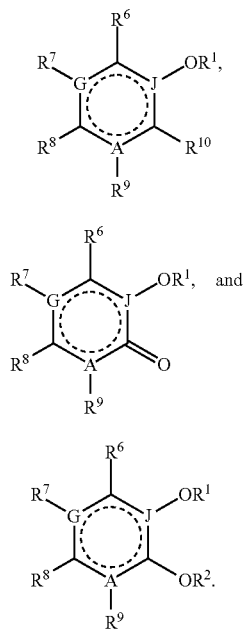

(I)

(II)

(III)

A and G are independently selected from carbon, nitrogen and oxygen. J is selected from carbon and nitrogen. Each $R^1$ and $R^2$ are independently selected from H, an enzymatically labile group, a hydrolytically labile group, a metabolically labile group, a photolytically labile group and a single negative charge. Each $R^6$, $R^7$, $R^8$, $R^9$, and $R^{10}$ are independently selected from a bond to $L^{41}$, $L^{42}$, $L^{43}$, $L^{44}$, $L^{45}$, or $L^{46}$, alkanediyl attached to $L^{41}$, $L^{42}$, $L^{43}$, $L^{44}$, $L^{45}$, or $L^{46}$, H, substituted or unsubstituted alkyl, substituted or unsubstituted heteroalkyl, halogen, CN, —$CF_3$, —$C(O)R^{17}$, —$SO_2NR^{17}R^{18}$, —$NR^{17}R^{18}$, —$OR^{17}$, —$S(O)_2R^{17}$, —$COOR^{17}$, —$S(O)_2OR^{17}$, —$OC(O)R^{17}$, —$C(O)NR^{17}R^{18}$, —$(CH_2)_mC(O)NR^{17}R^{18}$, —$O(CH_2)_mC(O)NR^{17}R^{18}$, —$NR^{17}C(O)R^{18}$, —$NR^{17}SO_2R^{18}$, and —$NO_2$. At least two of $R^6$, $R^7$, $R^8$, $R^9$, and $R^{10}$ are optionally joined to form a ring system selected from substituted or unsubstituted cycloalkyl, substituted or unsubstituted heterocycloalkyl, substituted or unsubstituted aryl and substituted or unsubstituted heteroaryl. m is an integer selected from 1, 2, 3, 4, 5, and 6. $R^{17}$ and $R^{18}$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. $R^{17}$ and $R^{18}$, together with the atoms to which they are attached, are optionally joined to form a 5-, 6- or 7-membered ring. When A is oxygen, $R^9$ is not present. When G is oxygen, $R^7$ is not present. $A^1$ is attached to $L^{41}$ through a member selected from $R^6$, $R^7$, $R^8$, $R^9$ and $R^{10}$. $A^2$ is attached to $L^{42}$ through a member selected from $R^6$, $R^7$, $R^8$, $R^9$ and $R^{10}$. $A^3$ is attached to $L^{43}$ through a member selected from $R^6$, $R^7$, $R^8$, $R^9$ and $R^{10}$. $A^4$ is attached to $L^{44}$ through a member selected from $R^6$, $R^7$, $R^8$, $R^9$ and $R^{10}$. $A^5$ is attached to $L^{45}$ through a member selected from $R^6$, $R^7$, $R^8$, $R^9$ and $R^{10}$. $A^6$ is attached to $L^{46}$ through a member selected from $R^6$, $R^7$, $R^8$, $R^9$ and $R^{10}$.

A compound according to the preceding paragraph, wherein when $A^1$ has a structure according to formula (I), $A^1$ is attached to $L^{41}$ through $R^6$ or $R^{10}$; when $A^1$ has a structure according to formula (II) or (III), $A^1$ is attached to $L^{41}$ through $R^6$ or $R^9$; when $A^2$ has a structure according to formula (I), $A^2$ is attached to $L^{42}$ through $R^6$ or $R^{10}$; when $A^2$ has a structure according to formula (II) or (III), $A^2$ is attached to $L^{42}$ through $R^6$ or $R^9$; when $A^3$ has a structure according to formula (I), $A^3$ is attached to $L^{43}$ through $R^6$ or $R^{10}$; when $A^3$ has a structure according to formula (II) or (III), $A^3$ is attached to $L^{43}$ through $R^6$ or $R^9$; when $A^4$ has a structure according to formula (I), $A^4$ is attached to $L^{44}$ through $R^6$ or $R^{10}$; when $A^4$ has a structure according to formula (II) or (III), $A^4$ is attached to $L^{44}$ through $R^6$ or $R^9$; when $A^5$ has a structure according to formula (I), $A^5$ is attached to $L^{45}$ through $R^6$ or $R^{10}$; when $A^5$ has a structure according to formula (II) or (III), $A^5$ is attached to $L^{45}$ through $R^6$ or $R^9$; when $A^6$ has a structure according to formula (I), $A^6$ is attached to $L^{46}$ through $R^6$ or $R^{10}$; and when $A^6$ has a structure according to formula (II) or (III), $A^6$ is attached to $L^{46}$ through $R^6$ or $R^9$.

A compound according to any preceding paragraph, wherein $A^1$, $A^2$, $A^3$, $A^4$, $A^5$, and $A^6$ are each independently selected from:

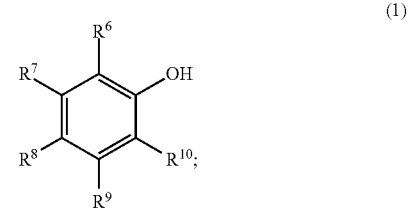

(1)

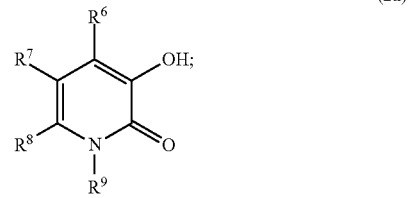

(2a)

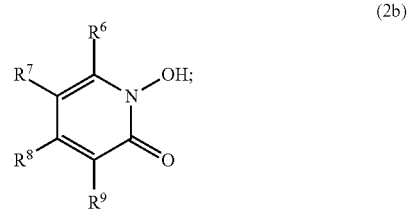

(2b)

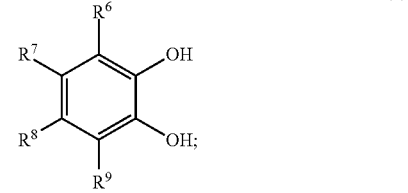

(3)

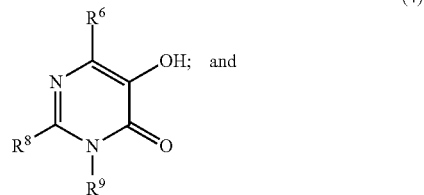

(4)

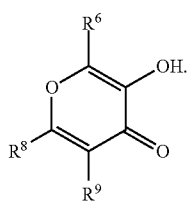

A compound according to the preceding paragraph, wherein when $A^1$ has a structure according to formula (1), $A^1$ is attached to $L^{A1}$ through $R^6$ or $R^{10}$; when $A^1$ has a structure according to formula (2a), (2b), (3), (4) or (5), $A^1$ is attached to $L^{A1}$ through $R^6$ or $R^9$; when $A^2$ has a structure according to formula (1), $A^2$ is attached to $L^{A2}$ through $R^6$ or $R^{10}$; when $A^2$ has a structure according to formula (2a), (2b), (3), (4) or (5), $A^2$ is attached to $L^{A2}$ through $R^6$ or $R^9$; when $A^3$ has a structure according to formula (1), $A^3$ is attached to $L^{A3}$ through $R^6$ or $R^{10}$; when $A^3$ has a structure according to formula (2a), (2b), (3), (4) or (5), $A^3$ is attached to $L^{A3}$ through $R^6$ or $R^9$; when $A^4$ has a structure according to formula (1), $A^4$ is attached to $L^{A4}$ through $R^6$ or $R^{10}$; when $A^4$ has a structure according to formula (2a), (2b), (3), (4) or (5), $A^4$ is attached to $L^{A4}$ through $R^6$ or $R^9$; when $A^5$ has a structure according to formula (1), $A^5$ is attached to $L^{A5}$ through $R^6$ or $R^{10}$; when $A^5$ has a structure according to formula (2a), (2b), (3), (4) or (5), $A^5$ is attached to $L^{A5}$ through $R^6$ or $R^9$; when $A^6$ has a structure according to formula (1), $A^6$ is attached to $L^{A6}$ through $R^6$ or $R^{10}$; and when $A^6$ has a structure according to formula (2a), (2b), (3), (4) or (5), $A^6$ is attached to $L^{A6}$ through $R^6$ or $R^9$.

A compound according to any preceding paragraph, wherein $A^1$, $A^2$, $A^3$, $A^4$, $A^5$, and $A^6$ are each independently selected from:

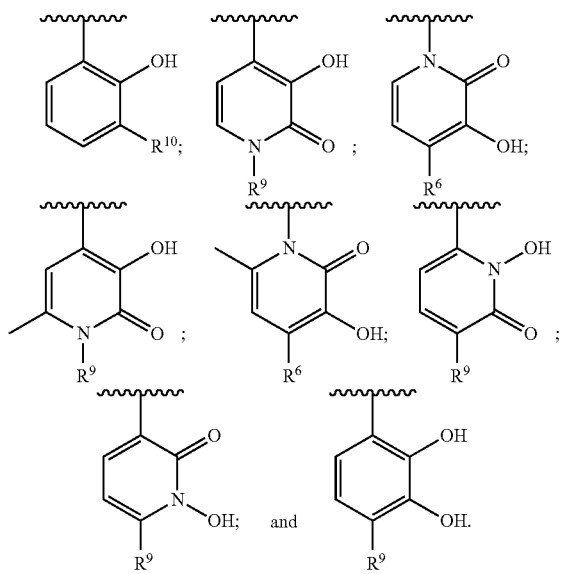

A compound according to any preceding paragraph, wherein $L^{s1}$, $L^{s2}$, $L^{s3}$, $L^{s4}$, and $L^{s5}$ are each independently selected from substituted or unsubstituted $C_1$, $C_2$, $C_3$, $C_4$, $C_5$, $C_6$, $C_7$ and $C_8$ alkyl.

A compound according to any preceding paragraph, wherein at least one of $L^{s1}$, $L^{s2}$, $L^{s3}$, $L^{s4}$, and $L^{s5}$ is substituted with a linker.

A compound according to any preceding paragraph, wherein $B^{s1}$, $B^{s2}$, $B^{s3}$, $B^{s4}$, $B^{s5}$, and $B^{s6}$ are each N.

A compound according to any preceding paragraph, wherein $L^{A1}$, $L^{A2}$, $L^{A3}$, $L^{A4}$, $L^{A5}$, and $L^{A6}$ are independently selected from a bond, —C(O)—, —(CH$_2$)$_a$C(O)—, and —O(CH$_2$)$_a$C(O)—; wherein a is an integer selected from 1, 2, 3, 4, 5, and 6.

A compound according to any preceding paragraph, wherein $L^{A1}$, $L^{A2}$, $L^{A3}$, $L^{A4}$, $L^{A5}$, and $L^{A6}$ are the same.

A compound according to any preceding paragraph, wherein $L^{A1}$, $L^{A2}$, $L^{A3}$, $L^{A4}$, $L^{A5}$, and $L^{A6}$ are each —C(O)—.

A compound according to any preceding paragraph, wherein $Y^1$ and $Y^2$ are each H.

A compound according to any preceding paragraph, having the structure

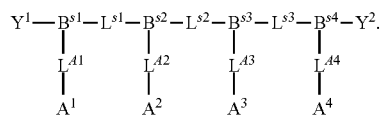

$L^{s1}$ and $L^{s3}$ are each independently selected from substituted or unsubstituted $C_2$, $C_3$, and $C_4$ alkyl. $L^{s2}$ is selected from substituted or unsubstituted $C_3$, $C_4$, and $C_5$ alkyl. At least one of $L^{s1}$, $L^{s2}$, and $L^{s3}$ is substituted with the linker.

A compound according to any preceding paragraph, having the structure

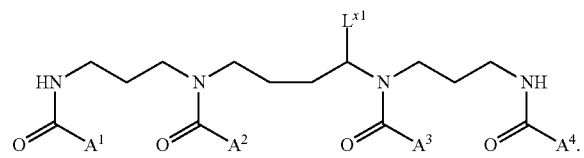

$L^{x1}$ is the linker.

A compound according to any preceding paragraph, having the structure

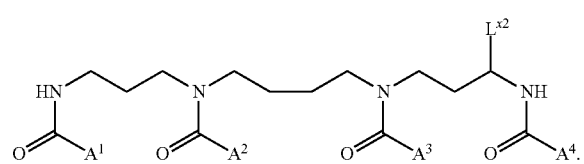

$L^{x2}$ is the linker.

A compound according to any preceding paragraph, having the structure

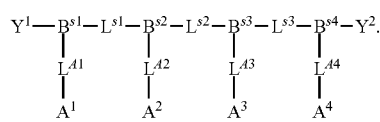

$Y^1$ is substituted alkyl comprising the linker. $Y^2$ is H. $B^{s1}$, $B^{s2}$, $B^{s3}$, and $B^{s4}$ are N. $L^{s1}$, $L^{s2}$, and $L^{s3}$ are each independently selected from unsubstituted $C_3$-$C_4$ alkyl. $L^{A1}$, $L^{A2}$, $L^{A3}$, and $L^{A4}$ are —C(O)—. $A^1$, $A^2$, $A^3$, and $A^4$ are chelating moieties having the structure

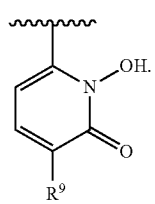

R⁹ is H.

A compound according to any preceding paragraph, wherein the linker has the structure -L¹¹-X. L¹¹ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. X is selected from a reactive functional group, a protected functional group, and a targeting moiety.

A compound according to any preceding paragraph, wherein the linker has the structure:

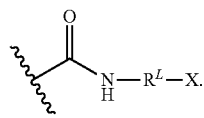

R^L is selected from substituted or unsubstituted alkyl, and substituted or unsubstituted heteroalkyl. X is selected from a reactive functional group, a protected functional group, and a targeting moiety.

A compound according to any preceding paragraph, wherein the linker has a structure selected from:

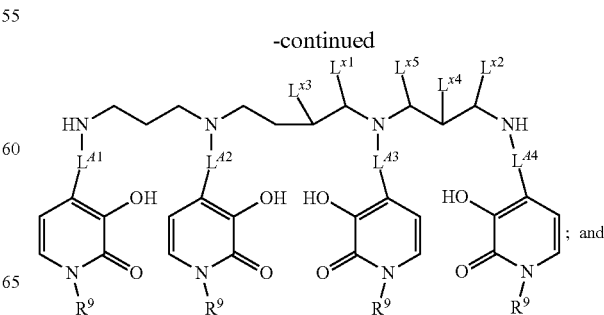

A compound according to any preceding paragraph, wherein the compound comprises one or more modifying moiety.

A compound according to the preceding paragraph, wherein one or more of A¹, A², A³, A⁴, A⁵, and A⁶ comprises a modifying moiety.

A compound according to the preceding paragraph, wherein, R⁶, R⁹ or R¹⁰ of each chelating moiety comprises a modifying moiety.

A compound according to any preceding paragraph, wherein the modifying moiety is selected from substituted or unsubstituted alkoxyalkyl and a substituted or unsubstituted polyether.

A compound according to any preceding paragraph, having a structure selected from:

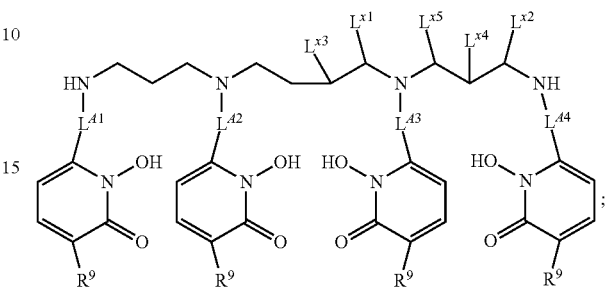

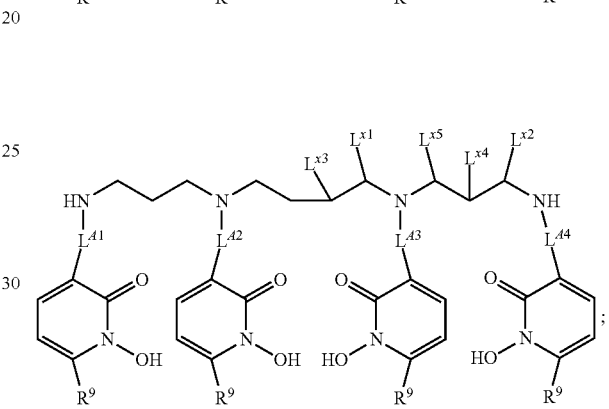

-continued

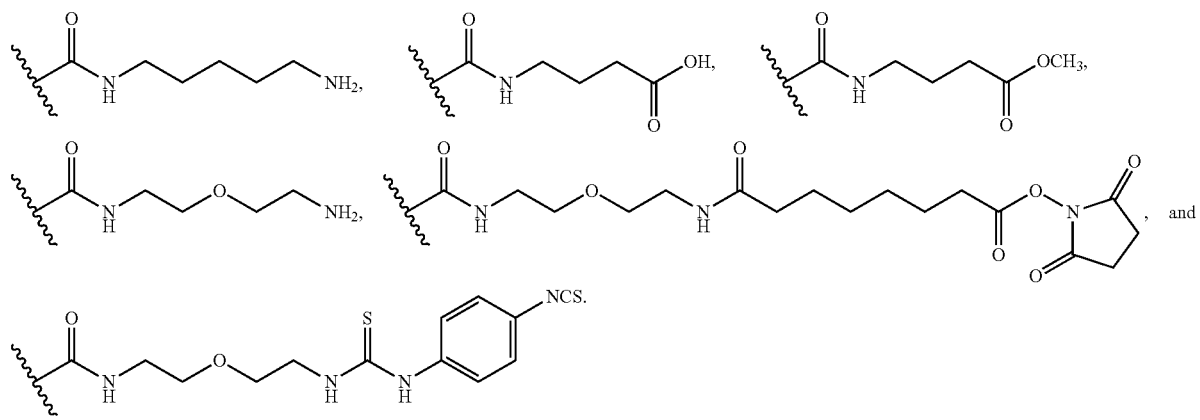

-continued
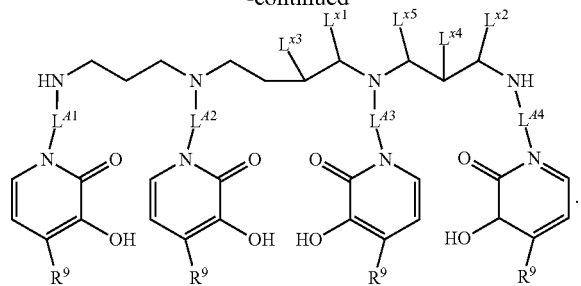
$L^{x1}$, $L^{x2}$, $L^{x3}$, $L^{x4}$, and $L^{x5}$ are independently selected from H and a linker, with the proviso that at least one of $L^{x1}$, $L^{x2}$, $L^{x3}$, $L^{x4}$, and $L^{x5}$ is the linker. Each $R^6$ and $R^9$ comprises a modifying moiety.
A compound according to any preceding paragraph, having a structure selected from:
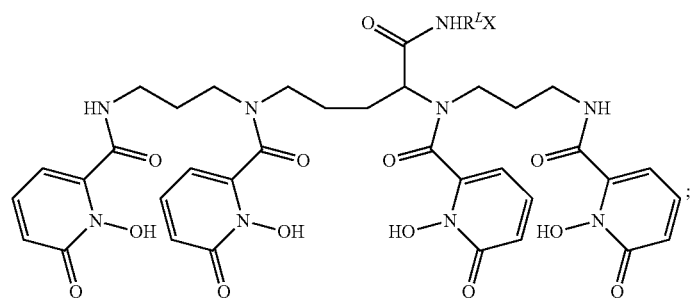
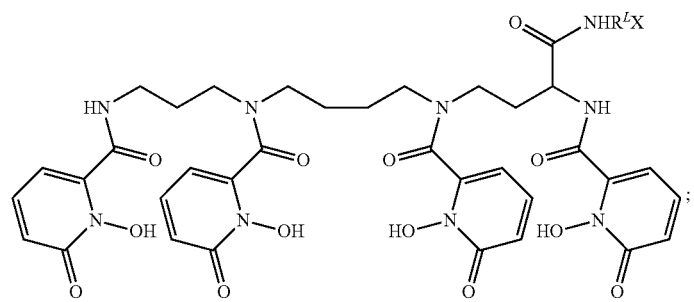
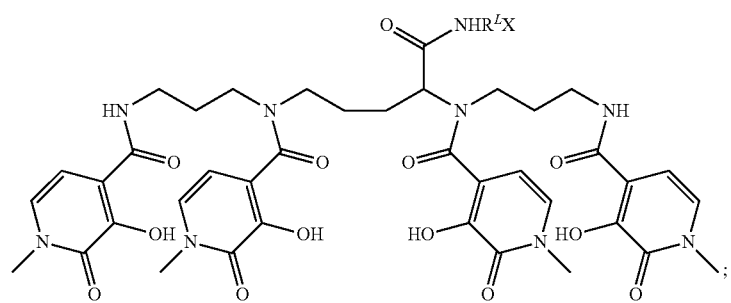
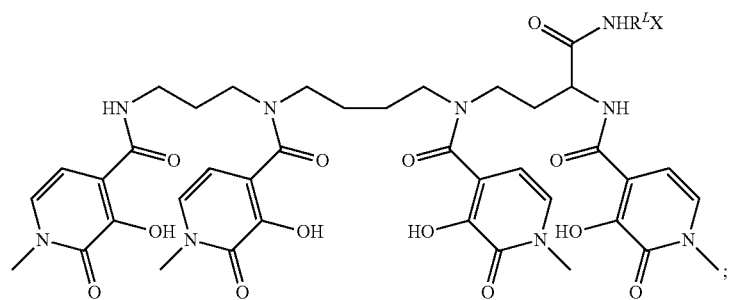

-continued
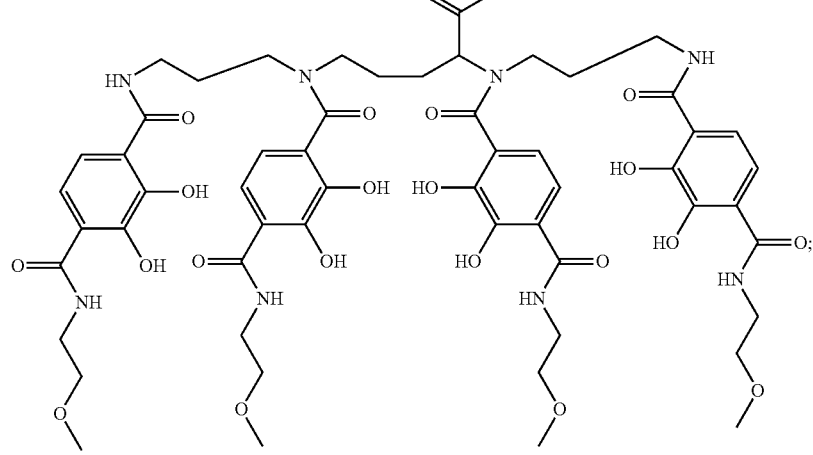
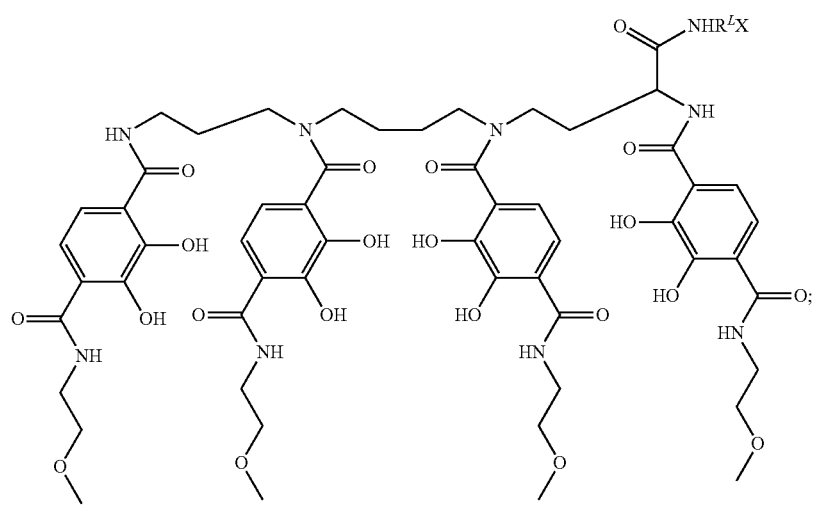
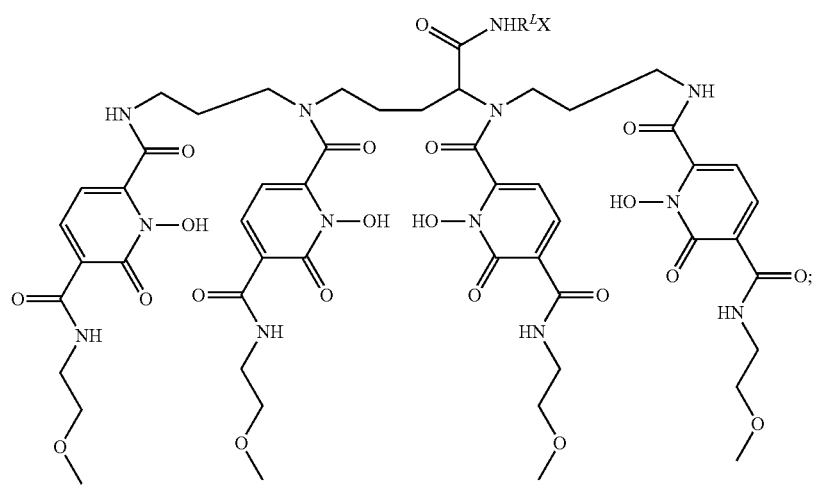

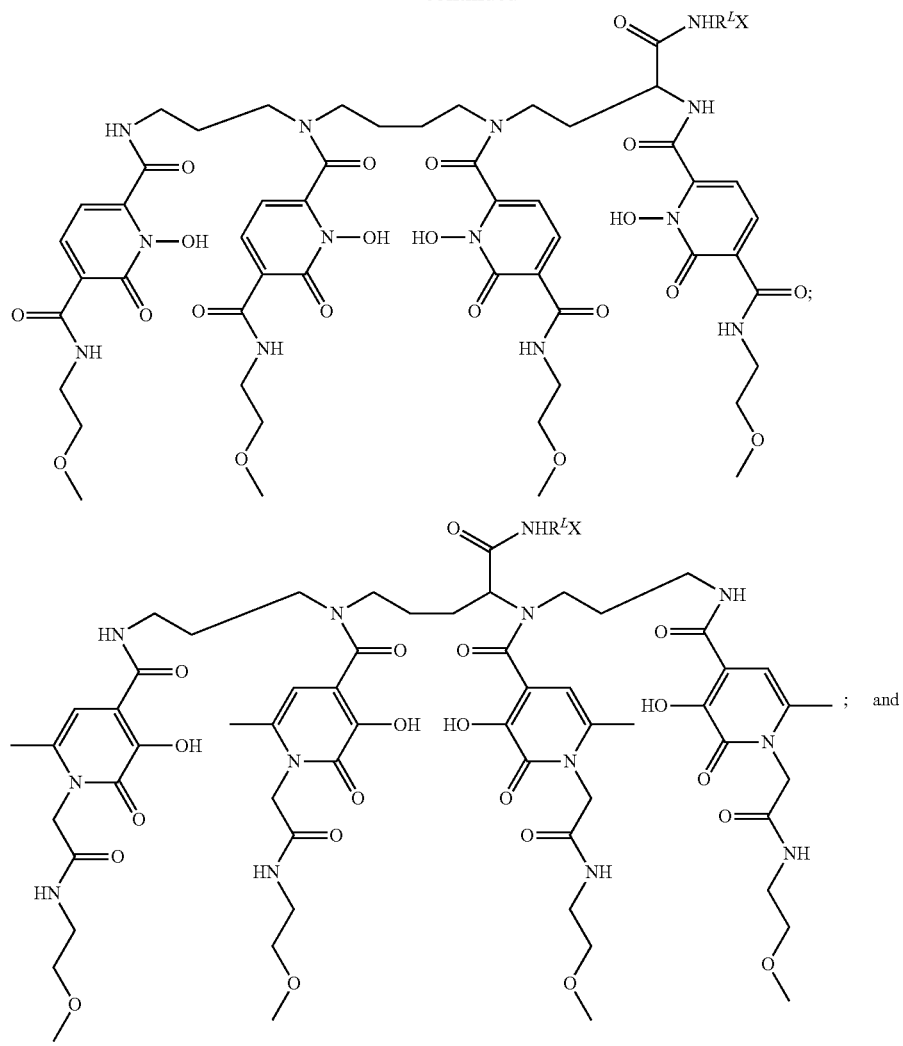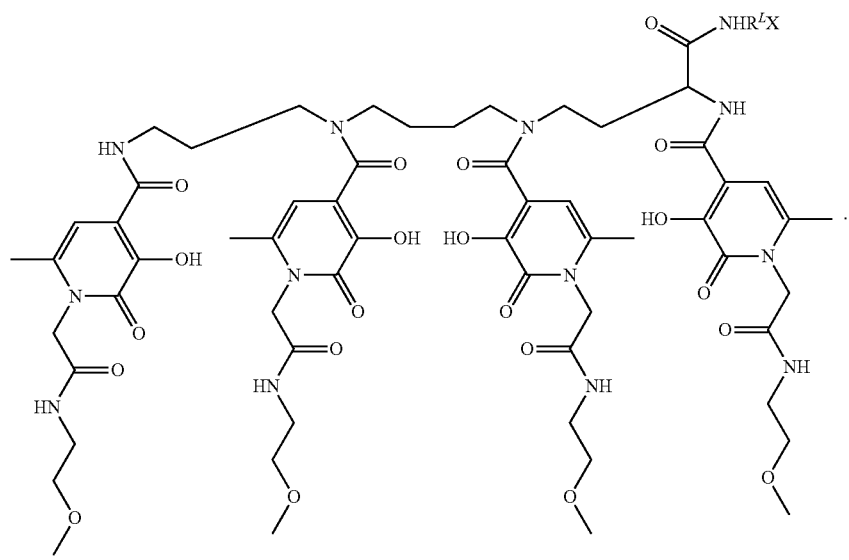

$R^L$ is selected from substituted or unsubstituted alkyl, and substituted or unsubstituted heteroalkyl. X is a reactive functional group or a targeting moiety.

A compound according to any preceding paragraph, wherein —$R^L$—X has a structure selected from:

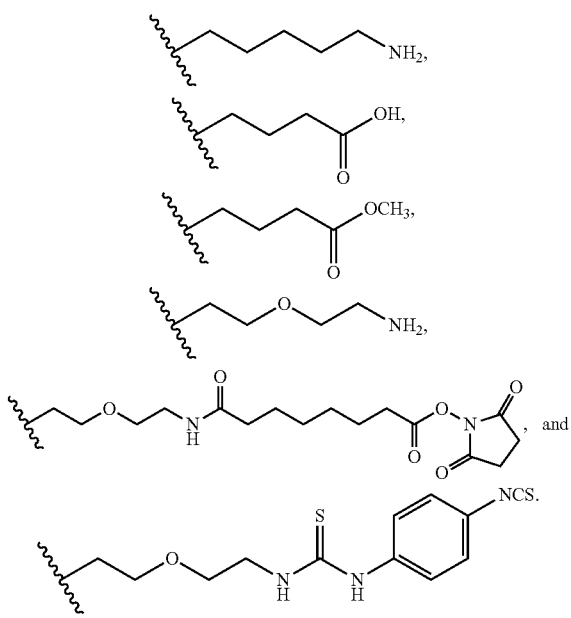

A complex comprising a compound according to any preceding paragraph and a metal ion.

A complex according to the preceding paragraph, wherein the metal is selected from a lanthanide, an actinide, yttrium (Y), and zirconium (Zr).

A complex according to any preceding paragraph, wherein the metal is selected from post-transition metals, metalloids, indium (In), gallium (Ga) and bismuth (Bi).

A complex according to any preceding paragraph, wherein the complex is luminescent.

A complex according to any preceding paragraph, wherein the lanthanide is luminescent.

A complex according to any preceding paragraph, wherein the lanthanide is selected from terbium (Tb), europium (Eu), dysprosium (Dy), and samarium (Sm).

A complex according to any preceding paragraph, wherein the lanthanide is gadolinium (Gd).

A complex according to any preceding paragraph, wherein the actinide is thorium (Th).

A complex according to any preceding paragraph, wherein the metal is a radionuclide.

A complex according to any preceding paragraph, wherein the metal is selected from $^{177}$Lu, $^{166}$Ho, $^{53}$Sm, $^{90}$Y, $^{86}$Y, $^{166}$Dy, $^{165}$Dy, $^{169}$Er, $^{175}$Yb, $^{225}$Ac, $^{149}$Tb, $^{153}$Gd, and $^{230}$U.

A complex according to any preceding paragraph, wherein the metal ion is $^{227}$Th(IV), $^{89}$Zr(IV), $^{177}$Lu(III), or $^{225}$Ac(III).

EXAMPLES

The compounds and complexes of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to limit the scope of reactions or reaction sequences that are useful in preparing the compounds of the present invention.

Design and Syntheses of Bi-Functionalized Spermine Based Octadentate Ligands

The spermine based ligand, 3,4,3-LI(1,2-HOPO), is a potent octadentate chelator of lanthanides and actinides. It forms a stable luminescent Eu(III) complex with quantum yield close to 20%. It is currently being developed as a drug to treat internal contamination with radionuclides by chelation therapy.

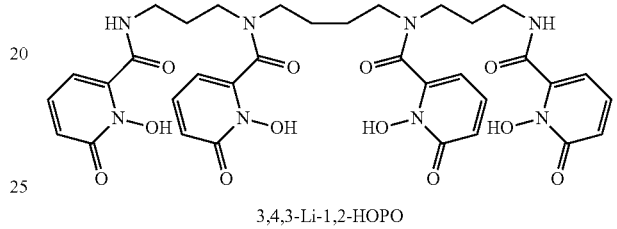

3,4,3-Li-1,2-HOPO

A bifunctional 3,4,3-1,2-HOPO and its analogues are expected to have extensive potential applications. The ligand scaffold of 3,4,3-LI-1,2-HOPO is spermine, and the object of synthesizing bifunctional 3,4,3-LI-1,2-HOPO is to add a functional group onto spermine that can be used as a linker to other molecules. Due to the symmetrical structure of spermine, there are two distinct positions available to functionalize spermine; in the central region or on the side, for example:

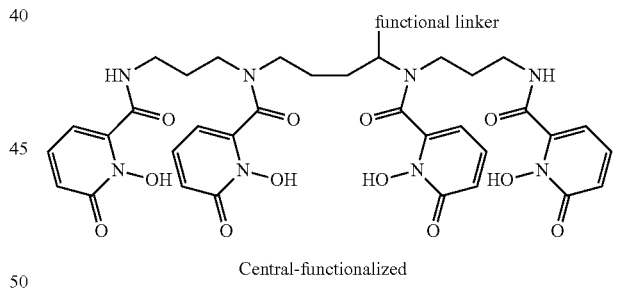

Central-functionalized

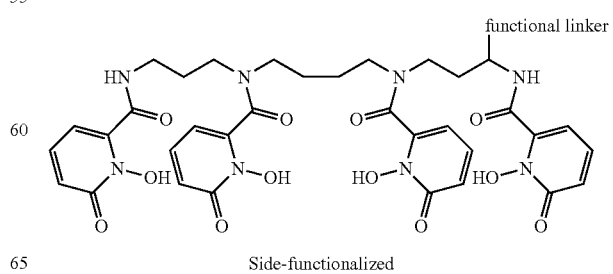

Side-functionalized

We have developed syntheses of both types of functionalized spermine scaffolds based on the readily available L-ornithine and L-aspartic acid derivatives.

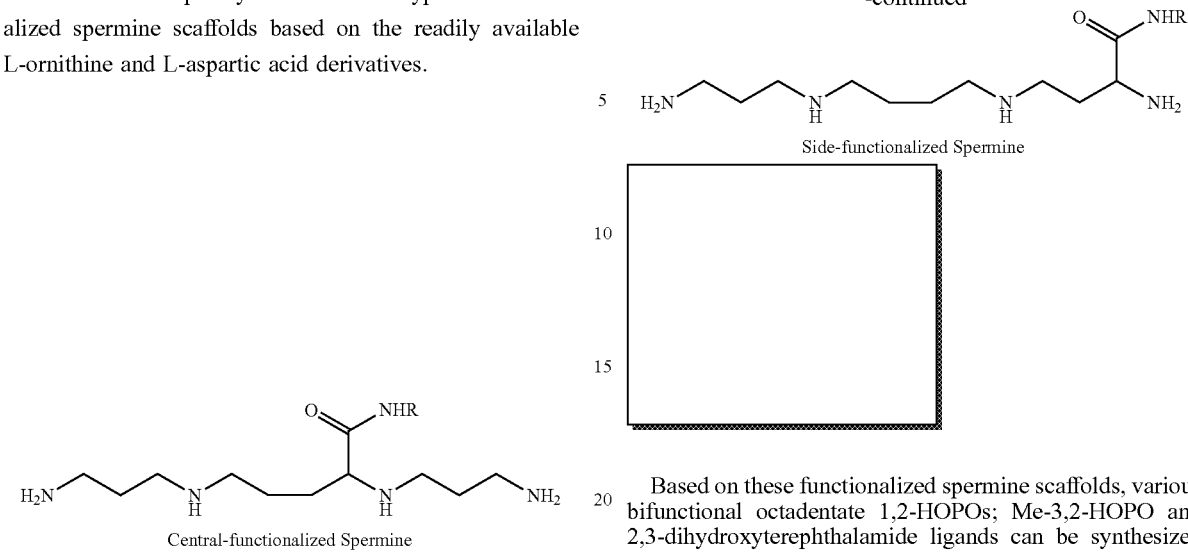
Side-functionalized Spermine

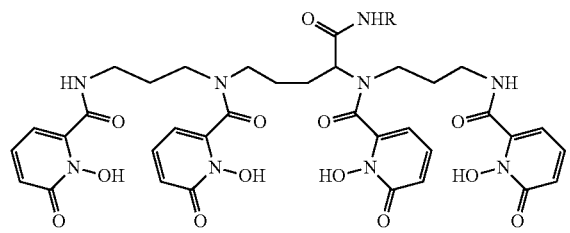
Central-functionalized Spermine

Based on these functionalized spermine scaffolds, various bifunctional octadentate 1,2-HOPOs; Me-3,2-HOPO and 2,3-dihydroxyterephthalamide ligands can be synthesized for the purposes of lanthanide luminescence and/or nuclear medicine. Some representative examples of such octadentate bifunctional chelators follow.

(IA)

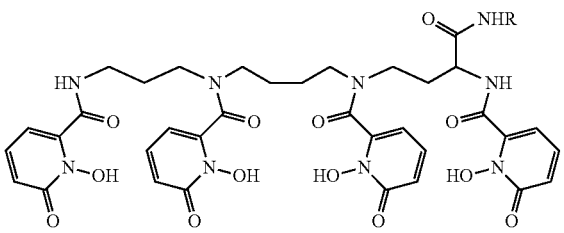
Central-functionalized 3,4,3-LI-1,2-HOPO (IB)

Side-functionalized 3,4,3-LI-1,2-HOPO (IIA)

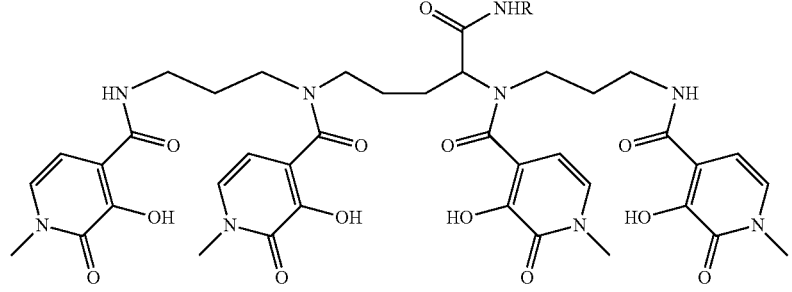
Central-functionalized 3,4,3-LI-Me-3,2-HOPO (IIB)

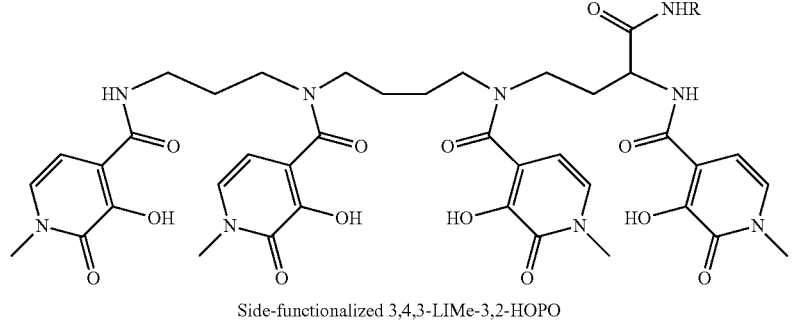
Side-functionalized 3,4,3-LIMe-3,2-HOPO

-continued
(IVA)
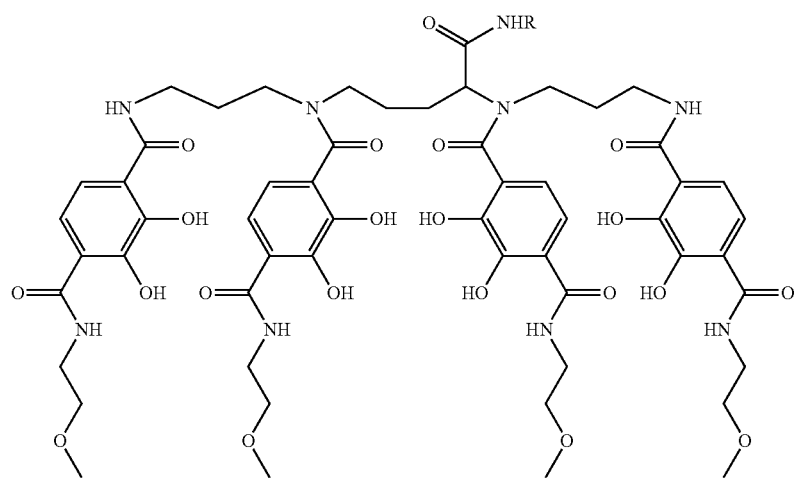
Central-functionalized 3,4,3-LI-MOETAM
(IVB)
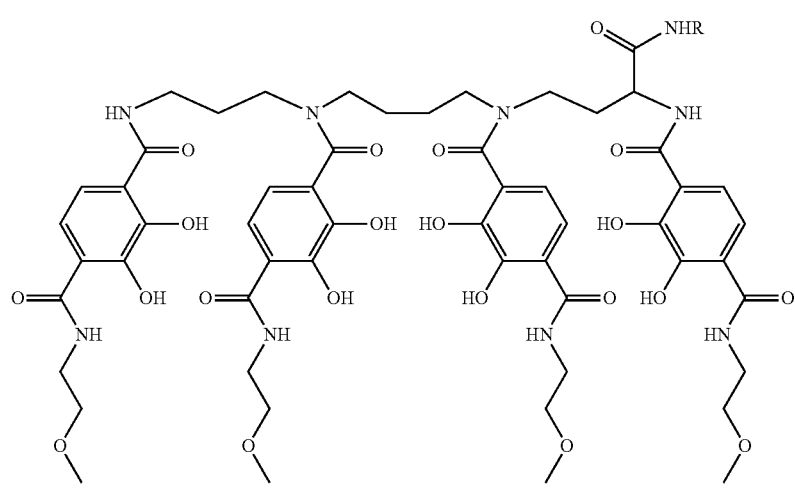
Side-functionalized 3,4,3-LI-MOETAM
(VA)
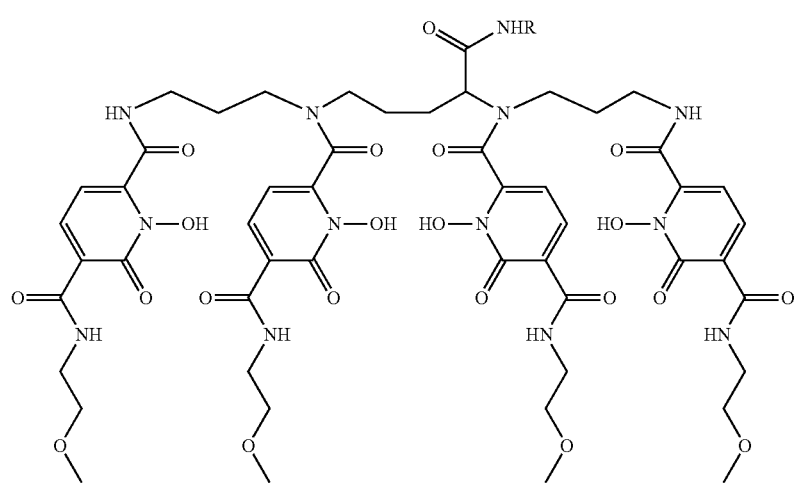
Central-functionalized 3,4,3-LI-1,2-HOPODA (VB)
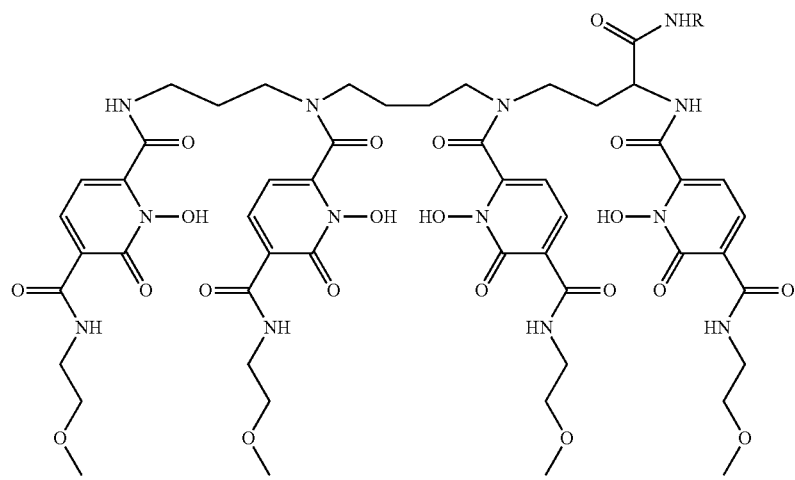
Side-functionalized 3,4,3-LI-1,2-HOPODA
(VIA)
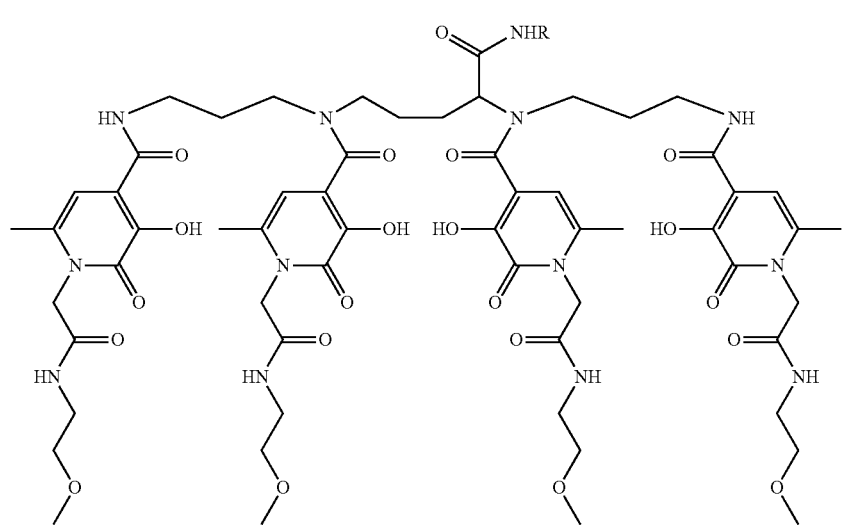
Central-functionalized 3,4,3-LI-6-Me-3,2-HOPODA
(VIB)
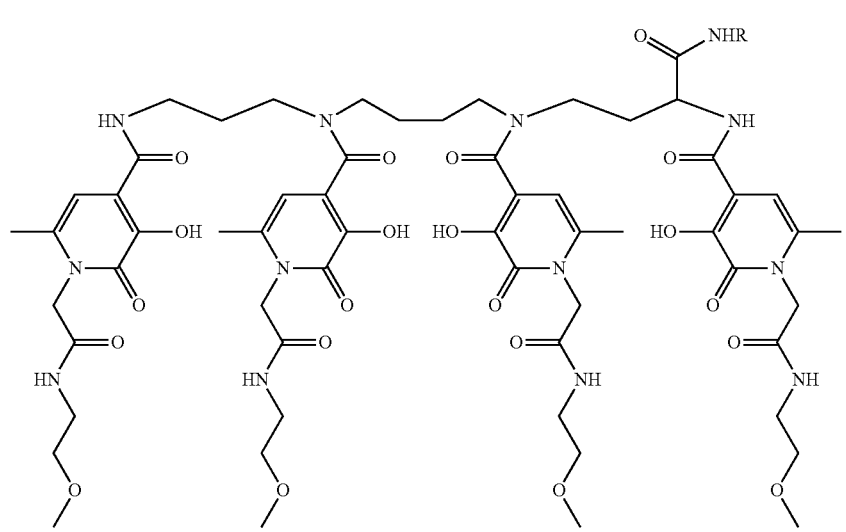
Side-functionalized 3,4,3-LI-6-Me-3,2-HOPODA -continued
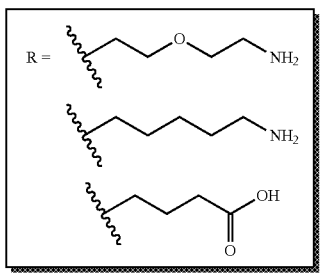
Example 1. Central Functionalized 3,4,3-LI-1,2-HOPO with Carboxylic Ester Group
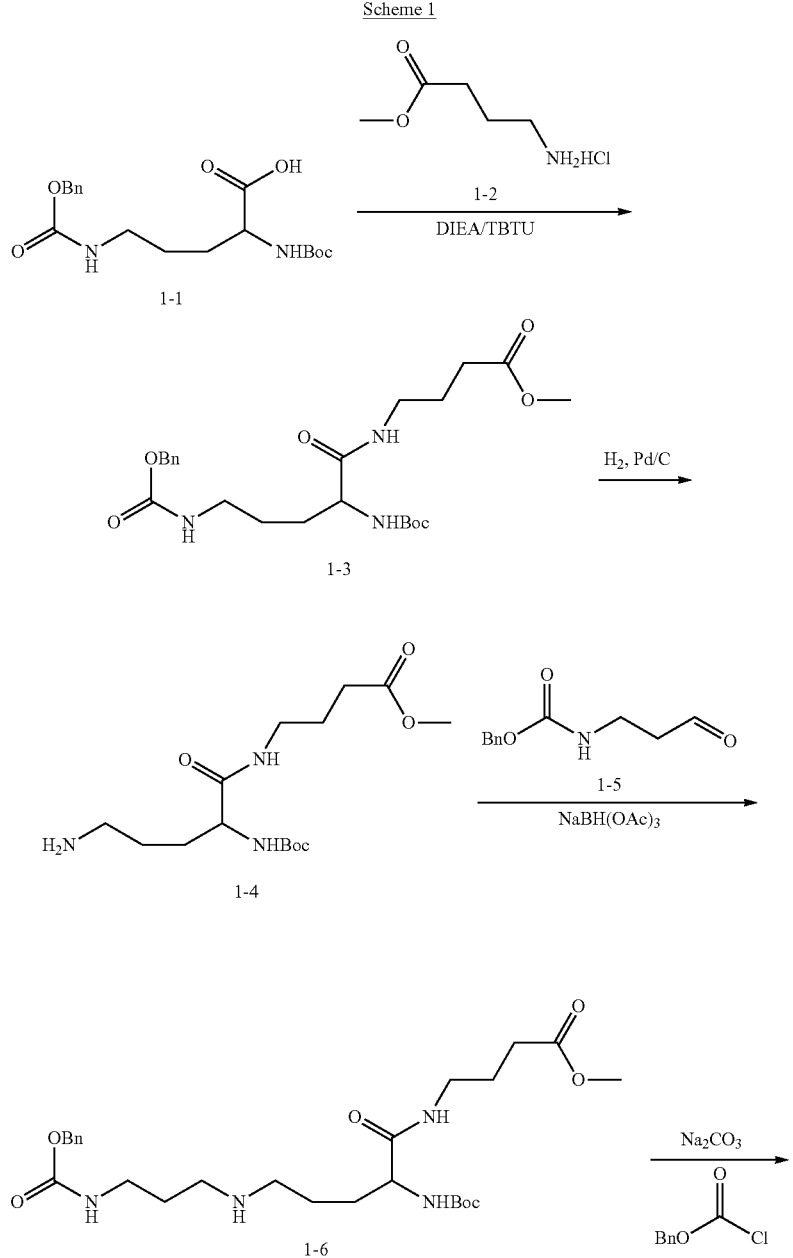

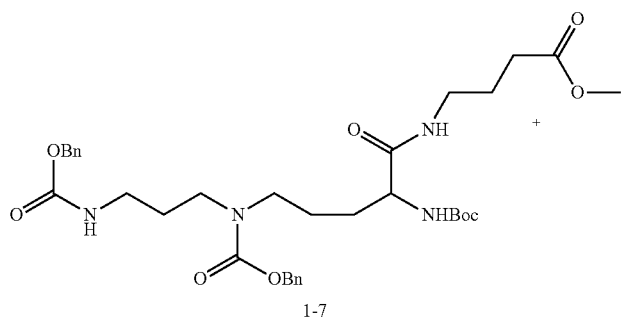
1-7
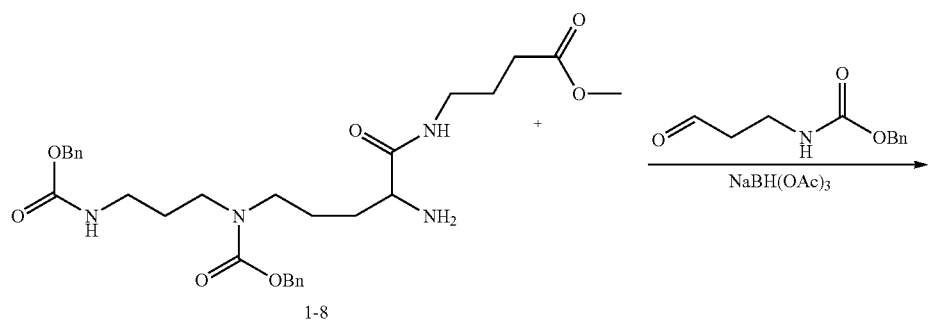
1-8
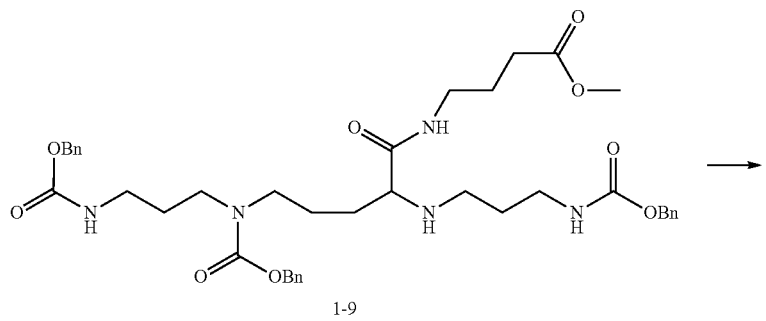
1-9
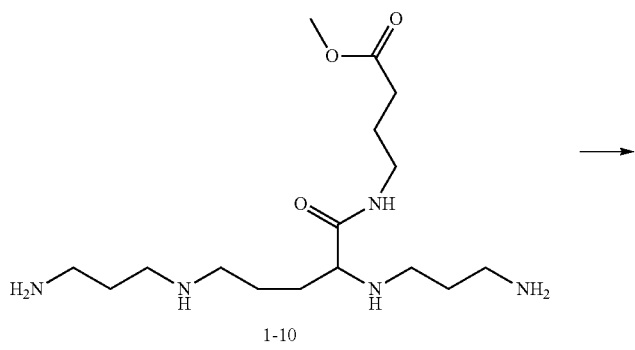
1-10

-continued
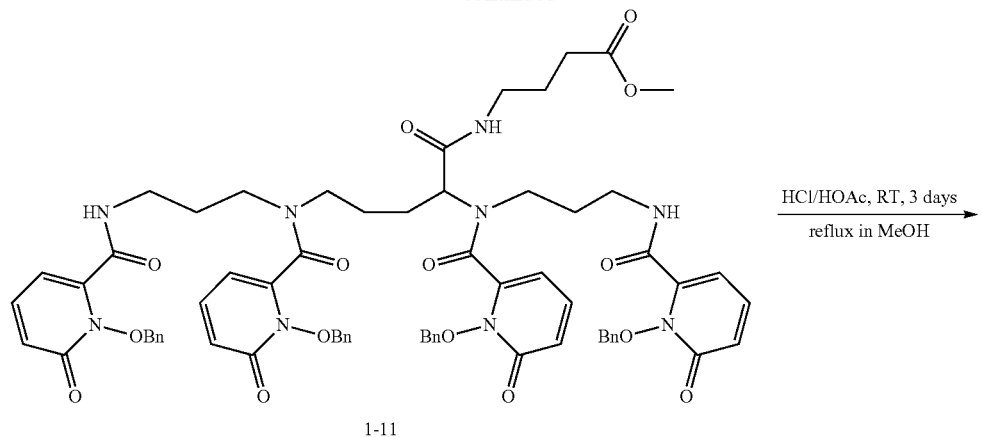
1-11
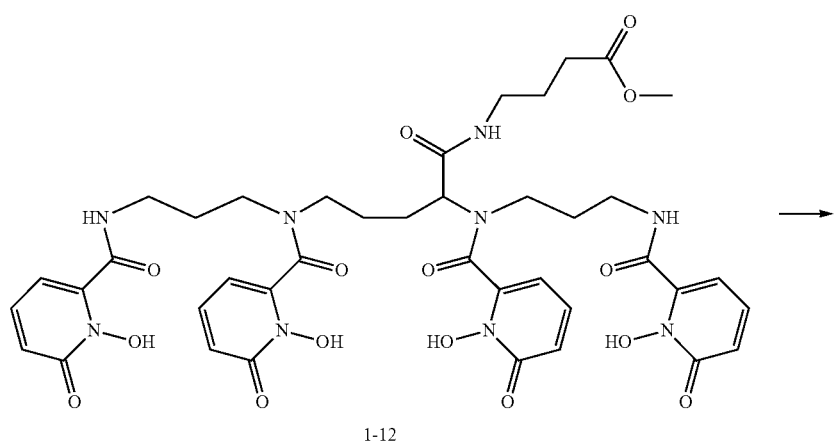
1-12
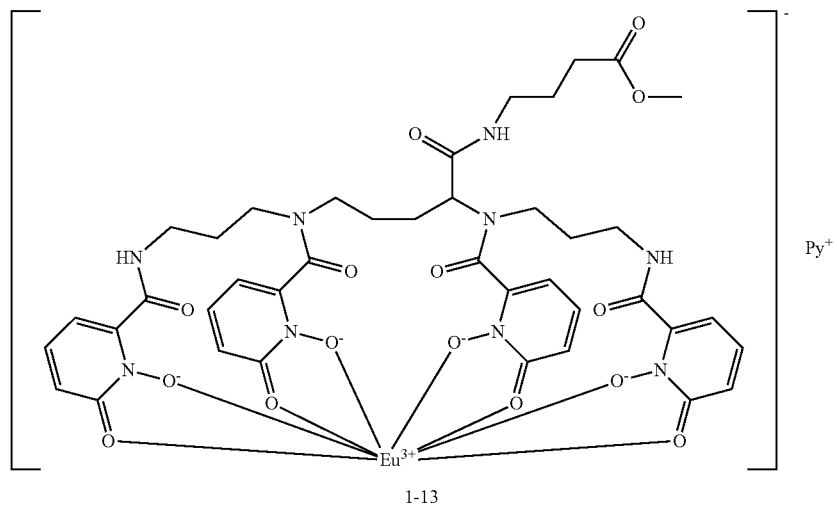
1-13

Methyl 4-aminobutanoate hydrochloride (1-2)

This is a known compound, it was prepared by following the literature protocol: Helena Fáková, Milan Pour, Jiří Kuneš and Petr Šenel, *Tetrahedron Letters* 46 (2005) 8137-8140.

Methyl 4-(5-(((benzyloxy)carbonyl)amino)-2-((tert-butoxycarbonyl)amino)-pentanamido)butanoate (ZBocOrnithineC4OMe, Compound 1-3)

Under nitrogen atmosphere, BocZ-Ornithine (Compound 1-1, 1.1 g, 3 mmol) was dissolved in 10 mL of anhydrous dimethylformamide. After the addition of 2.59 mL diisopropylethylamine (DIEA, 15 mmol), 744 mg of methyl 4-aminobutanoate hydrochloride (6 mmol) was added. Finally, the reaction was initiated by the addition of 2.39 g O-(benzotriazol-1-yl)-N,N,N',N'-tetramethyluronium tetrafluoroborate (TBTU, 7.5 mmol). The mixture was stirred overnight at room temperature. The reaction mixture was then evaporated under reduced pressure and the residue was purified by flash chromatography on silica gel using 3-7% methanol (MeOH) in dichloromethane (DCM), 72% yield. FTMS +pESI: calculated for $C_{23}H_{36}N_3O_7$ $[M+H]^+$, 466.2553, found, 466.2539.

$^1$H NMR (300 MHz, $CDCl_3$): δ=1.42 (s, 9H), 1.48-1.64 (s, br, 2H), 1.70-1.90, m 4H), 2.34 (t, 2H), 3.10-3.40 (m, 4H), 3.65 (s, 3H), 4.16 (s, br, 1H), 5.03 (s, 1H), 5.09 (s, 2H), 5.29 (s, br, 1H), 6.62 (s, br, 1H), 7.32 (m, 5H).
$^{13}$C NMR (75 MHz, $CDCl_3$): δ=24.4, 25.9, 28.1, 30.0, 31.2, 38.4, 39.8, 51.4, 53.3, 66.3, 79.5, 127.7, 127.8, 128.3, 136.5, 155.6 156.7, 162.4, 172.2, 173.5 ppm.

Methyl 4-(2-amino-5-((tert-butoxycarbonyl)amino) pentanamido)butanoate ($NH_2$BocOrniC4OMe Compound 1-4)

Compound 1-3 (0.93 g, 2 mmol) and 0.1 g of Pd/C catalyst (palladium, 10 wt. & on activated carbon (Aldrich)) were combined in methanol (25 mL). The mixture was hydrogenated (500 psi pressure, room temperature) overnight in a Parr bomb. After removing the catalyst by filtration, the filtrate was evaporated to dryness to provide $NH_2$BocOrniC4OMe, compound 1-4 as a pale yellow oil as product, yield 0.60 g (92%). FTMS +pESI: calculated for $C_{15}H_{30}N_3O_5$ $[M+H]^+$, 332.2185, found, 332.2177.

$^1$H NMR (300 MHz, $CDCl_3$): δ=1.26 (s, 9H), 1.40-1.7 (m, 6H), 2.20 (t, 2H), 2.73 (m, 2H), 3.09 (m, 2H), 3.51 (s, 3H), 4.03 (s, br, 1H), 6.02 (s, 1H), 7.86 (s, br, 3H).
$^{13}$C NMR (75 MHz, $CDCl_3$): δ=23.4, 24.3, 28.0, 30.9, 38.3, 49.4, 51.3, 52.9, 79.4, 155.9, 168.8, 172.3, 173.3, 177.6 ppm.

3-(Benzyloxycarbonylamino)propanal (1-5)

Step 1. Preparation of benzyl 3-hydroxypropylcarbamate

To a mixture of 3-aminopropan-1-ol (5.0 g, 67 mmol), $Na_2CO_3$ (8.8 g, 83 mmol) in tetrahydrofuran (THF, 40 mL) and $H_2O$ (130 mL) at 00° C. was added benzyl chloroformate (14.8 g, 87 mmol). The reaction mixture was stirred overnight at ambient temperature. THF was removed under reduced pressure and the aqueous phase was extracted with DCM (3×100 mL). The combined organic extracts were loaded onto a flash silica gel column, and eluted with 3-5% MeOH in DCM to afford benzyl 3-hydroxypropylcarbamate as a white solid (12.6 g, 90.5%).

1H NMR (400 MHz, $CDCl_3$): δ 7.35-7.27 (m, 5H), 5.27 (br.s, 1H), 5.09 (s, 2H), 3.71 (t, J=5.6 Hz, 2H), 3.32 (q, J=6 Hz, 2H), 1.74-1.69 (m, 2H).

Step 2. Preparation of 3-(Benzyloxycarbonylamino)propanal (1-5)

Benzyl 3-hydroxypropylcarbamate (8.37 g, 40 mmol) and 2,2,6,6-tetramethylpiperidine 1-oxyl (TEMPO, 0.19 g, 1.2 mmol) in dichloromethane (80 mL) were added to a solution of $NaIO_4$ (10.27 g, 48 mmol) and NaBr (0.41 g, 4.0 mmol) in water (100 mL). After stirring for 12 hrs at ambient temperature, the organic layer was separated, washed with 10% $Na_2S_2O_3$ and dried over $MgSO_4$. The solvent was removed in vacuo and the residue was recrystallized from $Et_2O$/n-hexane providing the aldehyde 1-5 (7.23 g, 87%) as a colorless solid. M.p. 52-54° C. $R_f$=0.36 (n-hexane/ethyl acetate 1:1). FTMS +pESI: calculated for $C_{11}H_{14}NO_3$ $[M+H]^+$, 208.0974, found, 208.0967.

$^1$H NMR (300 MHz, $CDCl_3$): δ=2.72 (t, J=5.7 Hz, 2H, CH2CH2CHO), 3.48 (dt, J=6.0, 6.0 Hz, 2H, CH2CH2CHO), 5.08 (s, 2H, OCH2Ph), 5.21 (s, 1H, NH), 7.27-7.40 (m, 5H, Ph), 9.78 (s, 1H, CHO).
$^{13}$C NMR (75 MHz, $CDCl_3$): δ=34.5, 44.0, 66.7, 128.0, 128.1, 128.5, 136.4, 156.3, 201.0 ppm.

Methyl 12-((tert-butoxycarbonyl)amino)-3,13-dioxo-1-phenyl-2-oxa-4,8,14-triazaoctadecan-18-oate (ZC3NHBocOrniC4OMe, Compound 1-6)

Compound 1-4 (1.66 g, 5 mmol) and 3-(benzyloxycarbonylamino)propanal 1-5 (0.41 g, 2 mmol) were mixed in THF (50 mL) at room temperature under $N_2$. The mixture was stirred for 3 hrs, then sodium triacetoxyborohydride (0.8 g, 4 mmol) was added and the mixture stirred at room temperature under a $N_2$ atmosphere for 24 hrs. A mixture of acetic acid and MeOH (1:1, 10 mL) was added to quench the reaction and the mixture was evaporated to dryness, the residue was taken into DCM and loaded onto a flash silica gel column. The appropriate fractions of a gradient elution (3-10% methanol in DCM) were collected and evaporated to dryness to provide compound 1-6 as a pale beige thick oil, yield: 0.44 g, 42% based on the aldehyde used. FTMS +pESI: calculated for $C_{26}H_{43}N_4O_7$ $[M+H]^+$, 523.3132, found, 523.3115.

$^1$H NMR (300 MHz, $CDCl_3$): δ=1.39 (s, 9H), 1.50 (m, 2H), 1.70 (m, 4H), 1.82 (m, 2H), 2.30 (t, 2H), 2.65 (m, 2H), 3.05 (s, br, 2H), 3.23 (m, 4H), 3.32 (s, br, 1H), 3.62 (s, 3H), 5.05 (s+s, 3H), 5.71 (s, br, 1H), 7.30 (s, 5H), 7.38 (s, 2H), 7.72 (s, 1H).
$^{13}$C NMR (75 MHz, $CDCl_3$): δ=21.9, 24.5, 25.8, 28.2, 28.7, 29.4, 31.1, 38.4, 39.5, 44.9, 51.5, 61.3, 66.4, 78.3, 127.8, 127.9, 128.3, 136.4, 156.2, 156.7, 162.4, 172.5, 173.4, 176.1 ppm.

ZC3Z-BocOrniC4OMe (Methyl 8-((benzyloxy)carbonyl)-12-((tert-butoxycarbonyl)amino)-3,13-dioxo-1-phenyl-2-oxa-4,8,14-triazaoctadecan-18-oate)), Compound 1-7)

A solution of compound 1-6 (1.05 g, 2 mmol) in DCM (30 mL) was mixed with 10% $Na_2CO_3$ solution (10 mL) cooling with an ice bath. To this vigorously stirring mixture a solution of benzyl chloroformate(0.43 g, 2.5 mmol) in DCM (10 mL) was added drop wise. The mixture was warmed to room temperature and stirred overnight when TLC indicated the reaction was complete. The volatiles were removed under vacuo, and the residue was loaded on a flash silica column. Elution with 2-6% methanol in DCM allows the separation of compound 1-7 (1.10 g, 85%) as a thick pale yellow oil. FTMS +pESI: calculated for $C_{34}H_{48}N_4NaO_9$ [M+Na]$^+$, 679.3319, found, 679.3296.

$^1$H NMR (300 MHz, CDCl$_3$): δ=1.39 (s, 9H), 1.72 (s, br, 6H), 1.87 (m, 2H), 2.24 (m, 4H), 3.07 (s, br, 2H), 3.16 (s, br, 2H), 3.28 (m, 2H), 3.63 (s, 3H), 4.41 (s, br, 1H), 5.03 (s, 2H), 5.10 (s, 2H), 5.43 (s, br, 1H), 6.86 (s, 1H), 7.29 (s, 10H).

$^{13}$C NMR (75 MHz, CDCl$_3$): δ=24.1, 25.7, 28.1, 29.3, 30.9, 38.2, 39.4, 41.8, 51.3, 53.2, 59.1, 66.0, 63.7, 78.6, 127.6, 127.7, 127.9, 128.1, 128.3, 135.8, 136.4, 155.9, 156.2, 156.7, 170.9, 173.2 ppm.

ZC3Z—NH$_2$-OrnC4OMe (Methyl 12-amino-8-((benzyloxy)carbonyl)-3,13-dioxo-1-phenyl-2-oxa-4,8,14-triazaoctadecan-18-oate), Compound 1-8)

Compound 1-7 (0.99 g, 1.5 mmol) and few drops of triisopropylsilane were dissolved in 25% trifluoroacetic acid (TFA) in DCM (10 mL) with stirring. After 3 hours, TLC revealed the reaction was complete. The volatile solvents were removed under reduced pressure, the residue was dissolved in DCM, and washed with saturated aqueous K$_2$CO$_3$ solution (5 mL). The organic phase was then passed through a plug of basic alumina; the product was then eluted with 7% MeOH in DCM. The combined DCM fractions were evaporated to dryness to provide compound 1-8 as a thick, pale yellow oil, yield 0.71 g (84%). FTMS +pESI: calculated for $C_{29}H_{41}N_4O_7$ [M+H]$^+$, 557.2975, found, 557.2958.

$^1$H NMR (300 MHz, CDCl$_3$): δ=1.20 (s, br, 2H), 1.59 (s, br, 6H), 1.76 (m, 2H), 2.11 (t, 2H), 2.46, (t, 2H), 3.03 (m, 4H), 3.16 (m, 2H), 3.45 (s, 3H), 4.29 (s, br, 1H), 4.90 (s, 2H), 4.97 (s, 2H), 5.70 (s, br, 1H), 7.25 (s, 10H).

$^{13}$C NMR (75 MHz, CDCl$_3$): δ=23.9, 25.6, 29.4, 30.6, 38.0, 41.0, 41.4, 51.0, 53.1, 58.8, 59.4, 65.7, 67.0, 126.1, 126.4, 127.3, 127.6, 127.8, 127.9, 135.6, 136.3, 156.0, 156.4, 170.6, 172.9 ppm.

Z3SpermC4OMe [Methyl 8-((benzyloxy)carbonyl)-12-((3-(((benzyloxy)carbonyl)amino)-propyl)amino)-3,13-dioxo-1-phenyl-2-oxa-4,8,14-triazaoctadecan-18-oate] (Compound 1-9)

Compound 1-8 (0.70 g, 1.25 mmol) and 3-(benzyloxycarbonylamino)propanal 1-5 (0.21 g, 1 mmol) were mixed in THF (10 mL) at room temperature under N$_2$. The mixture was stirred for 3 hrs, then sodium triacetoxyborohydride (0.4 g, 2 mmol) was added and the mixture stirred at room temperature under a N$_2$ atmosphere for 24 hrs. A mixture of acetic acid and MeOH (1:1, 10 mL) was added to quench the reaction, the mixture was evaporated to dryness, the residue dissolved in DCM, and loaded onto a flash silica gel column. The appropriate fractions of a gradient elution (3-10% methanol in DCM) were collected and evaporated to dryness to provide compound 1-9 as a pale beige thick oil, yield: 0.54 g, 72% based on the aldehyde used. FTMS +pESI: calculated for $C_{40}H_{54}N_5O_9$ [M+H]$^+$, 748.3922, found, 748.3902.

$^1$H NMR (300 MHz, CDCl$_3$): δ=1.39-2.00 (m, 12H), 2.16 (s, 2H), 2.68 (s, br, 4H), 2.80-3.40 (s, br, 8H), 3.50 (s, 3H), 4.38 (s, br, 1H), 4.96 (s, 4H), 5.02 (s, 2H), 5.84 (s, 1H), 6.36 (s, 1H), 7.29 (m, 15H), 8.99 (s, br, 2H).

$^{13}$C NMR (75 MHz, CDCl$_3$): δ=22.5, 23.2, 23.9, 25.7, 26.0, 29.3, 30.8, 37.2, 38.1, 38.3, 44.3, 46.4, 51.1, 65.9, 66.0, 67.2, 127.3, 127.5, 127.8, 128.0, 128.1, 135.7, 136.2, 136.3, 156.2, 156.6, 170.4, 173.1, 177.2 ppm.

SpermC4OMe (1-10)

Compound 1-9 (0.75 g, 1 mmol) and 0.1 g of Pd/C catalyst (palladium, 10 wt. % on activated carbon (Aldrich)) were combined in methanol (25 mL). The mixture was hydrogenated (500 psi pressure, room temperature) overnight in a Parr bomb. After removing the catalyst by filtration, and the filtrate was evaporated to dryness to leave pale yellow oil as the free amine, yield 0.29 g (84%). SpermC4OMe was used without further purification in the next step of the synthesis.

3,4,3-LI-1,2-HPBnC4OMe (1-11)

To a solution of the above amine (0.18 g, 0.5 mmol) in DCM (20 mL), DMAP (20 mg) and saturated aqueous K$_2$CO$_3$ solution (10 mL) were added. The mixture was cooled with an ice bath. A solution of 1,2-HOPOBn acid chloride prepared from 0.79 g 1,2-HOPOBn acid (3 mmol) in dry CH$_2$Cl$_2$ (10 mL) was added dropwise with vigorously stirring. The mixture was allowed to warm to room temperature overnight, when TLC indicated the reaction was complete. The organic phase was separated and the aqueous phase was extracted with DCM (3×10 mL). The combined organic extracts were dried with MgSO$_4$, and loaded on a flash silica column. Elution with 2-6% methanol in methylene chloride allowed the separation of compound 1-11 (0.42 g, 67% based on the amine) as a thick pale yellow oil. FTMS +pESI: calculated for $C_{68}H_{72}N_9O_{15}$ [M+H]$^+$, 1254.5148, found, 1254.5130.

3,4,3-LI-1,2-HOPO—C$_4$OMe [Methyl 4-(2,5-bis(1-hydroxy-N-(3-(1-hydroxy-6-oxo-1,6-dihydropyridine-2-carboxamido)propyl)-6-oxo-1,6-dihydropyridine-2-carboxamido)pentanamido)butanoate] (Compound 1-12)

Compound 1-11 (400 mg, 0.32 mmol) was dissolved in concentrated HCl (12 M)/glacial acetic acid (1:1, 20 mL), and was stirred at room temperature for 3 days. Filtration followed by removal of the solvent gave a beige residue, which was dissolved in a minimum amount of methanol and then mixed with diethyl ether while stirring. 3,4,3-1,2-HOPO—C$_4$OMe precipitated, and was collected by filtration and dried under vacuum at 80° C. affording a white powder as product (250 mg, 90%). FTMS –pESI: calculated for $C_{40}H_{46}N_9O_{15}$ [M]$^-$, 892.3113, found, 892.3111. Anal. for $C_{40}H_{47}N_9O_{15}$.2(HCl).2(H$_2$O), Calcd. (Found): C, 47.91 (47.92); H, 5.33 (5.18); N, 12.57 (12.46).

Eu$^{(III)}$ (3,4,3-LI-1,2-HOPO—C$_4$OMe) Complex (Compound 1-13)

A solution of europium chloride hexahydrate (37 mg, 0.1 mmol) in methanol (1 mL) was added to a solution of 3,4,3-LI-1,2-HOPO—C4OMe 1-12 (76 mg, 85 μmol) in methanol (5 mL) while stirring. The clear solution became turbid after 2 drops of dry pyridine were added. The mixture was refluxed for 6 hrs under nitrogen, during which time the metal complex deposited as a white precipitate. This solid was isolated by filtration, rinsed with cold methanol, and dried to give the pyridinium salt of compound 1-13 (63 mg, 66%) as a white solid. FTMS −pESI: calculated for $C_{40}H_{43}N_9O_{15}Eu$ [M]$^-$, 1042.2091, found, 1042.2077.

Anal. for $EuC_{40}H_{43}N_9O_{15}\cdot C_5H_6N\cdot 2H_2O$, Calcd. (Found): C, 46.72 (46.96); H, 4.52 (4.81); N, 12.11 (12.14).

The europium(III) complex of chelator 3,4,3-LI-1,2-HOPO—C4OMe was noted to be luminescent when viewed using a long wavelength (365 nm) UV lamp. Other metal complexes were prepared by combining one equivalent of 3,4,3-LI-1,2-HOPO—C4OMe with one equivalent of the metal salt in methanol using excess pyridine as a base as described above. The metal complexes were isolated by centrifugation as hydrated pyridinium salts. Samples were analyzed in methanol by mass spectrometry, with results reported below. Metal cation salts tested include thorium acetylacetonate, zirconium acetylacetonate, lutetium chloride hydrate (99.99+%), and yttrium chloride hydrate (99.99%).

Results:

1-12•Lu: FTMS −pESI: calculated for $C_{40}H_{43}N_9O_{15}Lu$ [M]$^-$, 1064.2286, found, 1064.2275.

1-12 •Th: FTMS +pESI: calculated for $C_{40}H_{43}N_9NaO_{15}Th$ [M+Na]$^+$, 1144.3157, found, 1144.3202.

1-12•Y: FTMS −pESI: calculated for $C_{40}H_{43}N_9O_{15}Y$ [M]$^-$, 978.1937, found, 978.1931.

1-12•Zr: FTMS +pESI: calculated for $C_{40}H_{43}N_9NaO_{15}Zr$ [M+Na]$^+$, 1002.1823, found, 1002.1843.

Example 2. Central Functionalized 5LIO-3,4,3-LI-1,2-HOPO

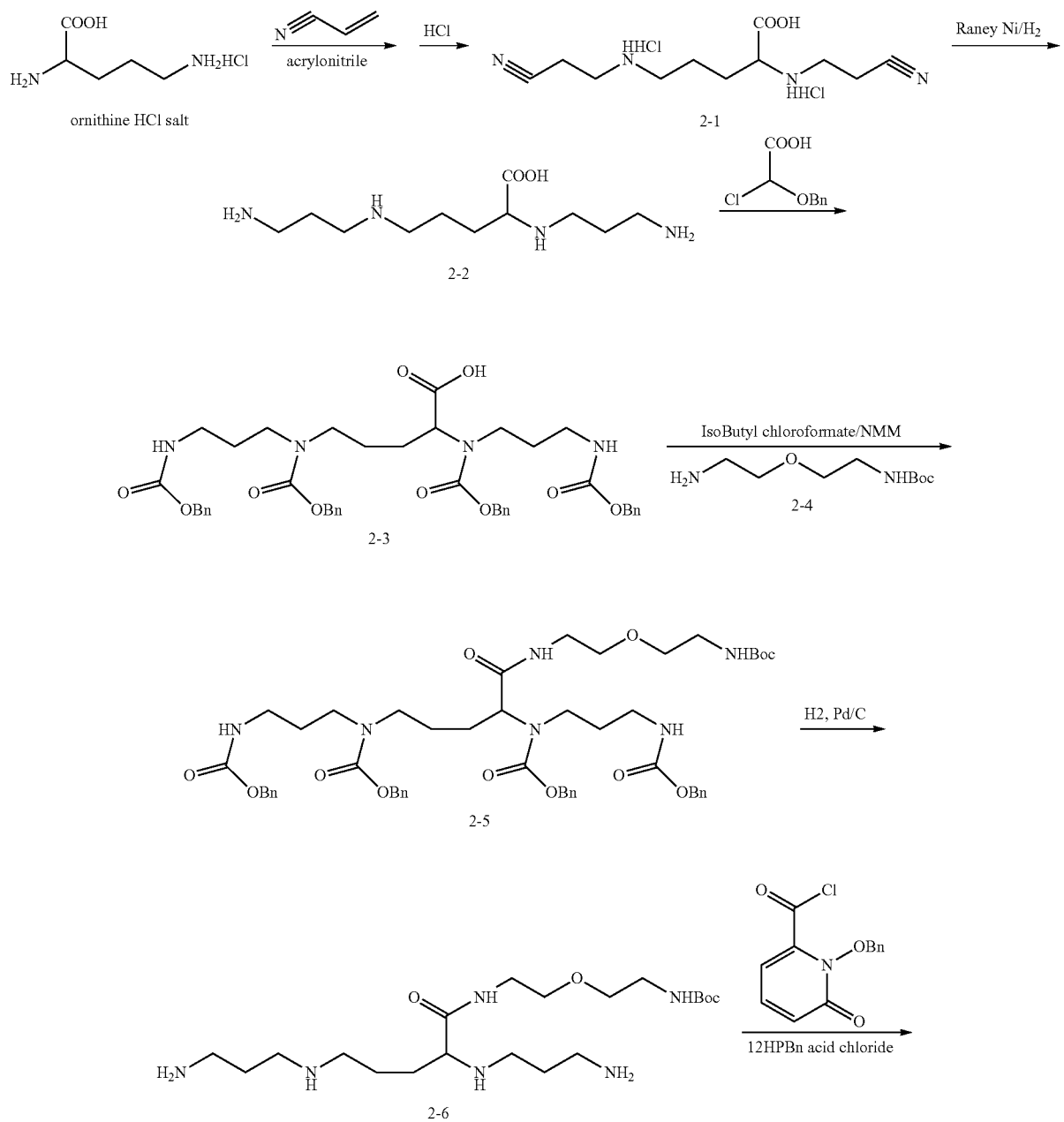

81
-continued
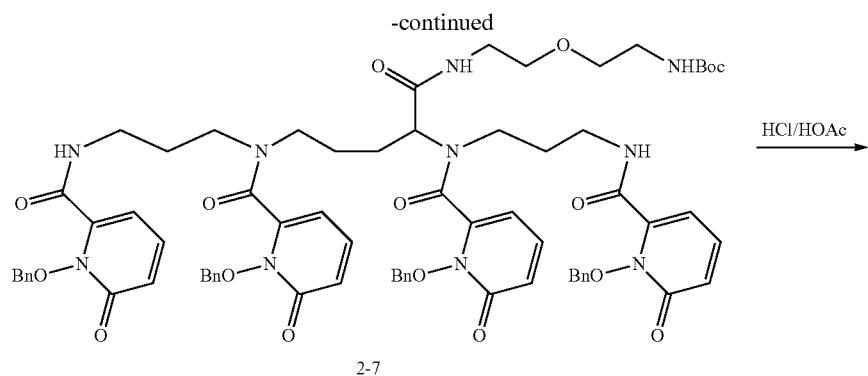
2-7
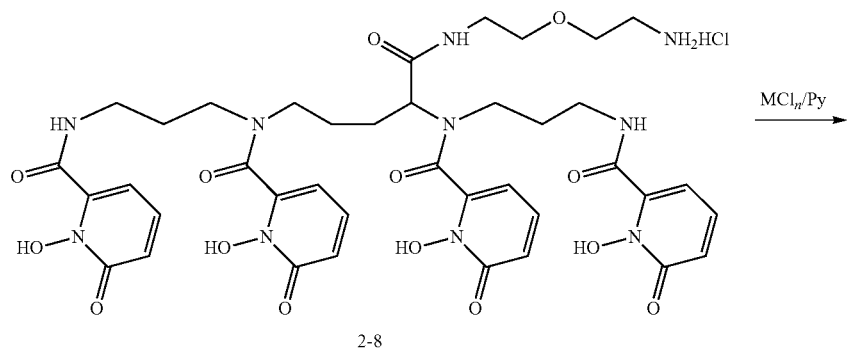
2-8
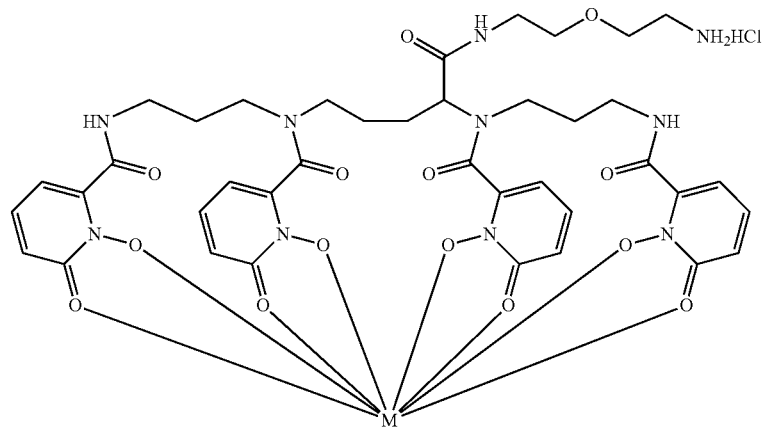
M = Th⁴⁺
= Zr⁴⁺
= Eu³⁺
= Dy³⁺
= Tb³⁺
= Lu³⁺
= Y³⁺

Synthesis

Compounds 2-1 and 2-2 are known; Behr, Jean Paul Journal of the Chemical Society, Chemical Communications (1989), (2), 101-3.

N$^\alpha$,N$^\delta$-Bis(2-cyanoethyl)ornithine (2-1)

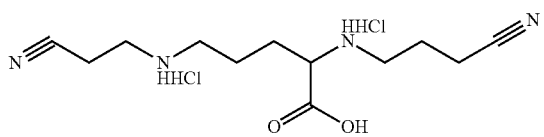

To a solution of L-ornithine HCl salt (16.86 g, 0.1 mol) in methanol (250 mL) was added a solution of NaOH (8 g, 0.2 mol) in methanol (100 mL). This mixture solution was stirred at room temperature. A solution of acrylonitrile (10.7 g, 0.2 mol) in dry methanol (20 mL) was added with stirring over 0.5 hour, the stirring was continued for 2 hrs, when TLC revealed that the reaction was complete. The reaction mixture was acidified slowly with conc. HCl (about 16 mL) to pH 4-5 while in an ice bath and the precipitate was filtered. (Note: Over-acidifying initiates the formation of the methyl ester of the product, and therefore should be avoided). The white precipitate appeared pure by TLC and NMR, but was contaminated by NaCl salt. It was used for next step of reaction without further purification. Raw yield 27 g.

Carboxy-Spermine, [N$^\alpha$,N$^\delta$-Bis(2-aminoethyl)ornithine] (2-2)

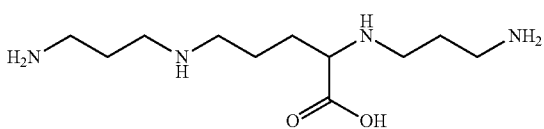 [SMILES: NCCCNCCCC(NCCCN)C(=O)O]

The above raw product of N$^\alpha$,N$^\delta$-Bis(2-cyanoethyl)ornithine (15 g) was dissolved in 1.4 M solution of NaOH in 95% ethanol (80 mL) with ice cooling, then 4 g of Raney Ni/water was added to this mixture. The mixture was hydrogenated in a Parr bomb at room temperature under 1000 psi hydrogen pressure for 24 h with stirring. The Raney Ni was removed by filtration over Celite on a fine porosity glass frit, the filtrate was evaporated resulting in a transparent thick oil which was used without further purification.

Carboxy-SpermineZ4 [N$^\alpha$,N$^\delta$-Bis(benzylcarbamol)-N$^\alpha$,N$^\delta$-Bis(2-benzylcarbamoylethyl)-ornithine] (2-3)

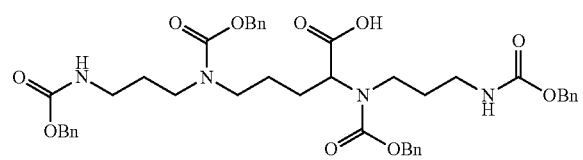 [SMILES: O=C(NCCCN(CCCC(C(=O)O)N(CCCNC(=O)OCc1ccccc1)C(=O)OCc1ccccc1)C(=O)OCc1ccccc1)OCc1ccccc1]

To an ice cooling solution of raw N$^\alpha$,N$^\delta$-Bis(2-aminoethyl)ornithine (5 g, assay calculated for 100% yield) in a mixture of THF (50 mL) and 12% K$_2$CO$_3$ aqueous solution (50 mL) was added a solution of benzyl chloroformate (17 g, 1.2 eq) in THF (50 mL) with vigorous stirring over a 2 hr period. Stirring was continued overnight, and most of the THF was removed under vacuum. The aqueous phase was washed with ethyl acetate (25 mL×2), and the organic washes were discarded. The aqueous phase was then acidified to pH 3 with 6N HCl, and the product was extracted with ethyl acetate (30×3 mL). The combined organic extracts were combined and evaporated to dryness. The residue was purified by gradient flash chromatography on silica gel using 5-10% MeOH/DCM as eluent to yield 6.5 g (41%) of the product as a white foam.

Boc5LIO-Spermine-Z4, (2-5)

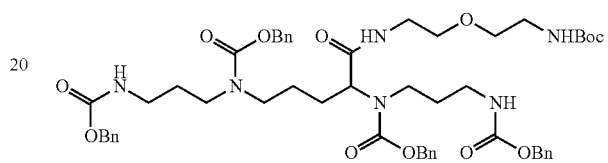

Compound 2-3 (7.9 g, 10 mmol) was dissolved in 30 mL of anhydrous THF and the solution was cooled to −20° C. under nitrogen. N-methyl morpholine (NMM, 1.2 mL, 11 mmol) was added, the solution was stirred for 10 min, iso-butyl chloroformate (1.37 mL, 10.5 mmol) was added to the cold solution via syringe slowly, and the solution was stirred at −10° C. for 45 min. The mixture was then cooled to −40° C. and a solution of Boc-5LIO-amine HCl salt (compound 2-4, 2.9 g, 12 mmol) in DMF (20 mL) was added dropwise to the above cold solution via a Teflon tube. The mixture was stirred at −40° C. for 20 min, allowed to warm to room temperature slowly, and the stirring was maintained for another 8 hrs. The reaction mixture was then evaporated to dryness, dissolved in DCM (50 mL), and washed with aqueous 10% citric acid (2×30 mL) and 5% KHCO$_3$ solution (2×30 mL) successively. The organic phase was loaded onto a flash silica gel column, and the product was separated by gradient elution with methanol in DCM to provide compound 2-5 as a semisolid material. Yield 7.8 g (80%). FTMS +pESI: calculated for C$_{52}$H$_{69}$N$_6$O$_{12}$ [M+H]$^+$, 969.4973, found, 969.4982.

Boc5LIO-Spermine (2-6)

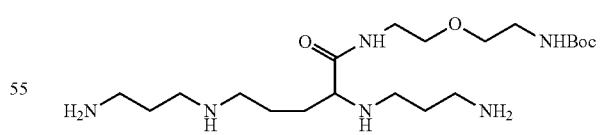

Compound 2-5 (0.97 g, 1 mmol) and 0.1 g of Pd/C catalyst (palladium, 10 wt. % on activated carbon (Aldrich)) were combined in methanol (25 mL). The mixture was hydrogenated (500 psi pressure, room temperature) overnight in a Parr bomb. After removing the catalyst by filtration, and the filtrate was evaporated to dryness to provide compound 2-6 as a pale yellow oil, yield 0.36 g (83%). (Note: The reductive deprotection can be performed in the methanol-acetic acid medium too. The reaction time in this case is much shorter, a few hours is enough.) FTMS +pESI: calculated for $C_{20}H_{45}N_6O_4$ [M+H]$^+$, 433.3502, found, 433.3492.

Boc-5LIO-Spermine-1,2-HOPOBn (2-7)

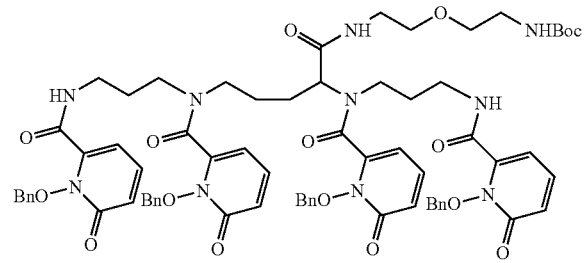 [SMILES: CC(C)(C)OC(=O)NCCOCCNC(=O)C(CCCN(CCCNC(=O)c1cccc(=O)n1OCc1ccccc1)C(=O)c1cccc(=O)n1OCc1ccccc1)N(CCCNC(=O)c1cccc(=O)n1OCc1ccccc1)C(=O)c1cccc(=O)n1OCc1ccccc1]

To a vigorously stirred suspension of the raw Boc5LIO-Spermine (compound 2-6, 0.43 g, 10 mmol) in DCM (30 mL) and an aqueous solution of $K_2CO_3$ (4M, 30 mL), cooled with an ice bath, was added slowly a solution of 1,2HOPOBn chloride (made from 1.5 gram of 1,2-HOPOBn acid, 6 mmol, 1.5 equiv.) in dry DCM (30 mL) over 30 min. After the addition was completed the ice bath was removed and the reaction was stirred overnight. The organic phase was separated, the solvent was evaporated, and the crude product was purified by flash silica gel column chromatography to afford compound 2-7 (910 mg, 68% yield) as white foam.

NH$_2$5LIO-Spermine-1,2-HOPO HCl Salt (2-8)

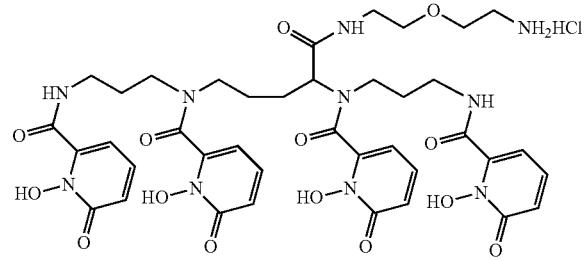

Boc5LIO-Spermine-1,2-HOPOBn (compound 2-7, 268 mg, 0.2 mmol) and triisopropylsilane (0.1 ml) were dissolved in a mixture of concentrated HCl (12 M) and glacial acetic acid (1:1, 20 mL). The mixture was stirred at room temperature for 3 days. The volatiles were removed under reduced pressure to leave a beige residue, which was dissolved in a minimum amount of methanol and precipitated by addition of isopropanol. The NH$_2$5LIO-Spermine-1,2-HOPO HCl salt precipitate was collected by filtration and dried under vacuum at 80° C. affording a beige powder as product (yield 140 mg, 76%). FTMS −pESI: calculated for $C_{39}H_{47}N_{10}O_{14}$ [M]$^-$, 879.3273, found, 879.3305.

Anal. for $C_{39}H_{48}N_{10}O_{14}$·HCl·CH$_3$OH·2H$_2$O, Calcd. (Found): C, 48.76 (48.99); H, 5.83 (6.04); N, 14.21 (14.26).

Preparation of Metal Complexes of NH$_2$5LIO-Spermine-1,2-HOPO 2-8

Metal complexes were prepared by combining one equivalent of the NH$_2$5LIO-Spermine-1,2-HOPO (compound 2-8) with one equivalent of the metal chloride or acetylacetonate salt in methanol using excess pyridine as a base. The metal complexes were isolated by centrifugation as hydrated pyridinium salts. Samples were analyzed in methanol by mass spectrometry, with results reported below. The europium(III) complex of chelator 2-8 was noted to be luminescent when viewed using a long wavelength (365 nm) UV lamp. Metal cation salts tested include europium(III) chloride hexahydrate (99.99%), terbium chloride hexahydrate (99.9%), thorium acetylacetonate, zirconium acetylacetonate, lutetium chloride hydrate (99.99+%), yttrium chloride hydrate (99.99%), and dysprosium chloride hydrate (99.99%).

Results:

2-8•Eu: FTMS −pESI: calculated for $C_{39}H_{44}N_{10}O_{14}$Eu [M]$^-$, 1029.2251, found, 1029.2270.

2-8•Th: FTMS +pESI: calculated for $C_{39}H_{45}N_{10}O_{14}$Th [M+H]$^+$, 1109.3497, found, 1109.3465.

2-8•Dy: FTMS +pESI: calculated for $C_{39}H_{46}N_{10}O_{14}$Dy [M+2H]$^+$, 1042.2487, found, 1042.2492.

2-8•Tb: FTMS +pESI: calculated for $C_{39}H_{46}N_{10}O_{14}$Tb [M+2H]$^+$, 1037.2448, found, 1037.2432.

2-8 •Lu: FTMS +pESI: calculated for $C_{39}H_{46}N_{10}O_{14}$Lu [M+2H]$^+$, 1053.2603, found, 1053.2584.

2-8 •Y: FTMS +pESI: calculated for $C_{39}H_{46}N_{10}O_{14}$Y [M+2H]$^+$, 967.2253, found, 967.2238.

2-8 •Zr: FTMS +pESI: calculated for $C_{39}H_{45}N_{10}O_{14}$Zr [M+H]$^+$, 967.2158, found, 967.2174.

Anal. for EuC$_{39}$H$_{44}$N$_{10}$O$_{14}$HCl·C$_5$H$_6$N·4H$_2$O, Calcd. (Found): C, 43.41 (43.67); H, 4.88 (4.76); N, 12.66 (12.75).

Example 3: Synthesis of 5LIO-Spermine-Me-3,2-HOPO

Scheme 2-2

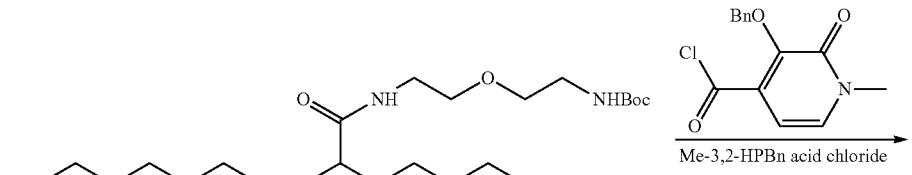

2-6

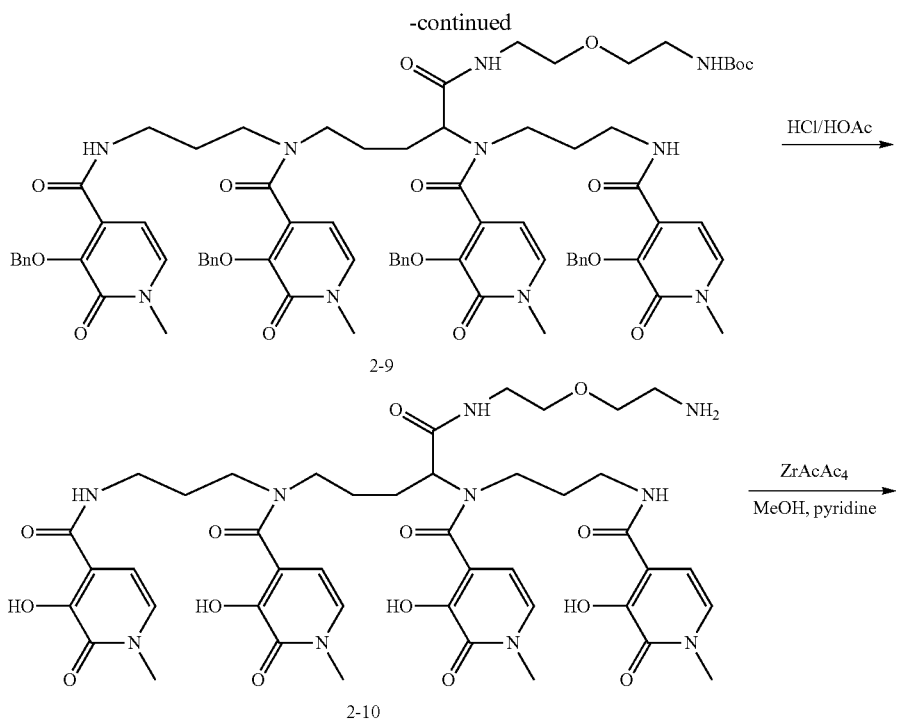

2-9

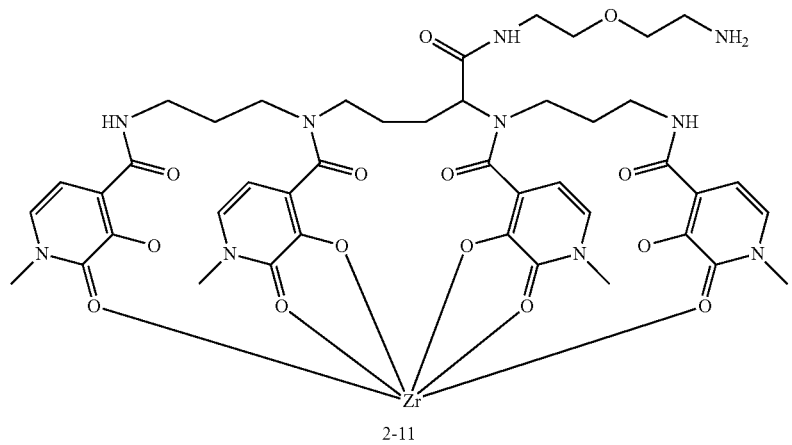

2-10

2-11

Boc-5LIO-Spermine-Me-3,2-HOPOBn (2-9)

This compound was prepare according the same procedure as Boc-5LIO-Spermine-1,2-HOPOBn, except Me-3,2-HOPOBn acid chloride was used instead of 1,2-HOPOBn acid chloride. White foam was obtained as product, yield 65%. FTMS +pESI: calculated for $C_{76}H_{89}N_{10}O_{16}$ [M+H]$^+$, 1397.6458, found, 1397.6464.

NH2-5LIO-Spermine-Me-3,2-HOPO (2-10)

This compound was prepare according the same procedure as NH2-5LIO-Spermine-1,2-HOPO, except Boc-5LIO-Spermine-Me-3,2-HOPOBn was used instead of Boc-5LIO-Spermine-1,2-HOPOBn. Compound 2-10 was obtained as a white foam, yield 65%. FTMS −pESI: calculated for $C_{43}H_{55}N_{10}O_{14}$ [M]$^-$, 935.3899, found, 935.3908.

Anal. for $C_{43}H_{56}N_{10}O_{14}$·HCl·$CH_3OH$·$2H_2O$, Calcd. (Found): C, 50.74 (50.60); H, 6.29 (6.55); N, 13.45 (13.31).

Zirconium(IV) Complex with NH2-5LIO-Spermine-Me-3,2-HOPO (2-11)

The zirconium complex was prepared by combining NH$_2$5LIO-Spermine-Me-3,2-HOPO (compound 2-10) with one molar equivalent of zirconium acetylacetonate in methanol using excess pyridine as a base. The metal complex was precipitated with ethyl ether and isolated by centrifugation. The resulting solid was washed with isopropyl alcohol and dried. A sample was analyzed by mass spectrometry by dissolving in 10% dimethylsulfoxide in methanol. 2-11: FTMS +pESI: calculated for $C_{43}H_{53}N_{10}O_{14}Zr$ [M+H]$^+$, 1023.2784, found, 1023.2798.

Example 4. Central Functionalized Spermine with Pendent Amino Group
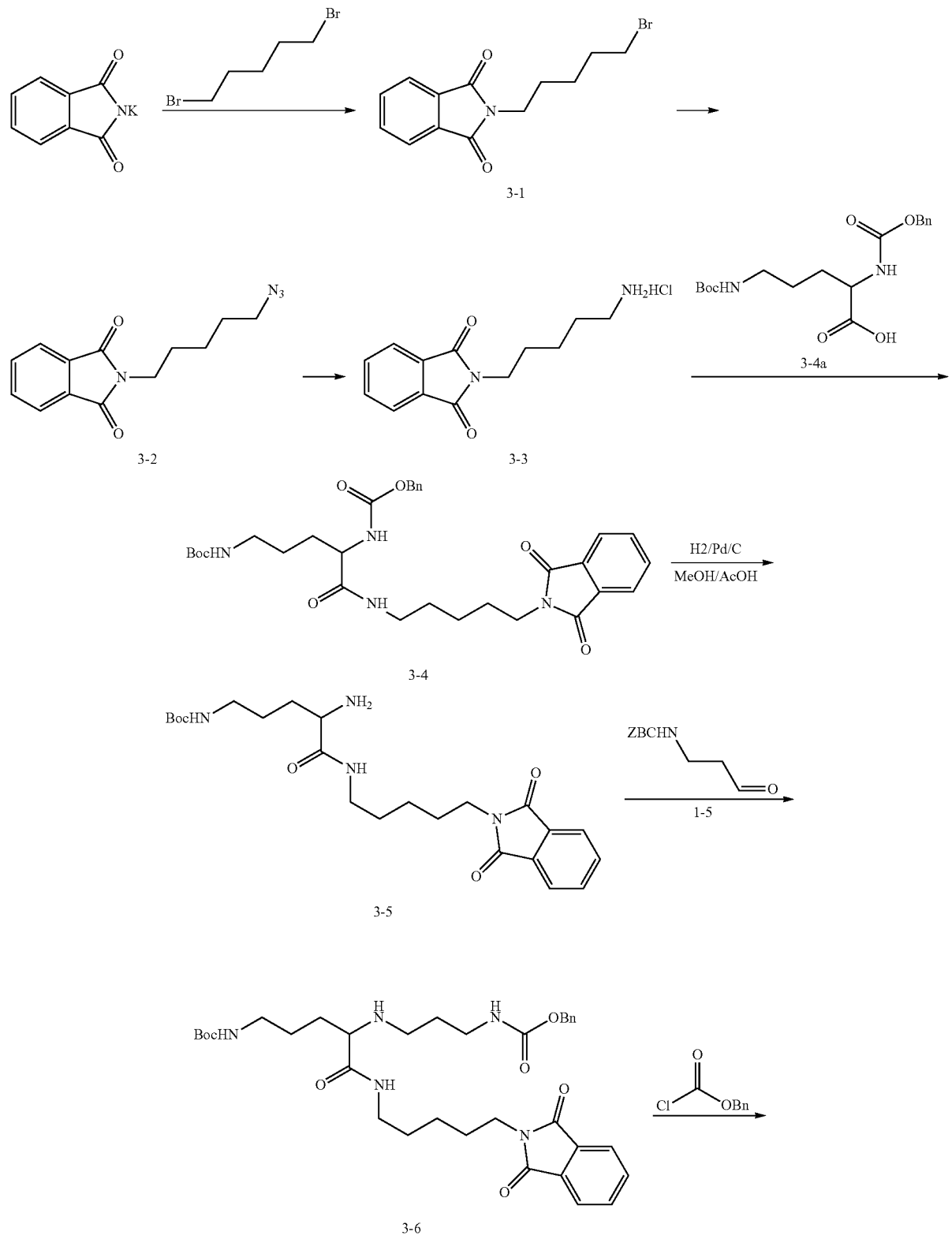
Scheme 3

-continued
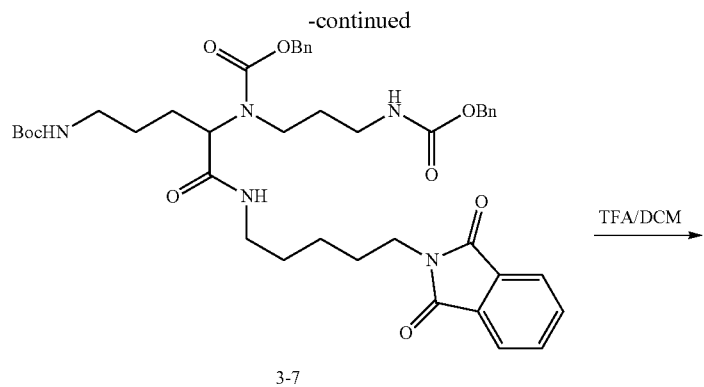
3-7
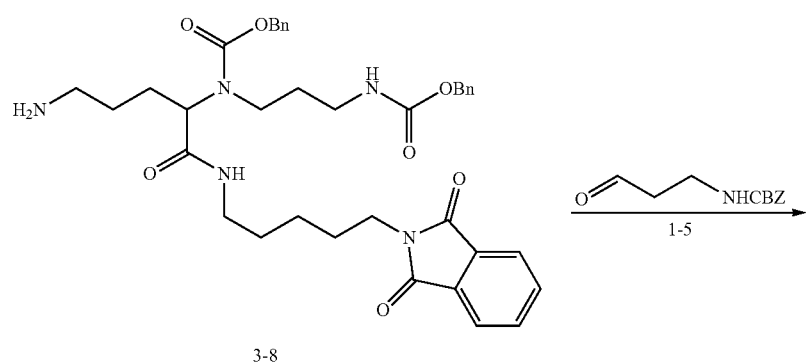
3-8
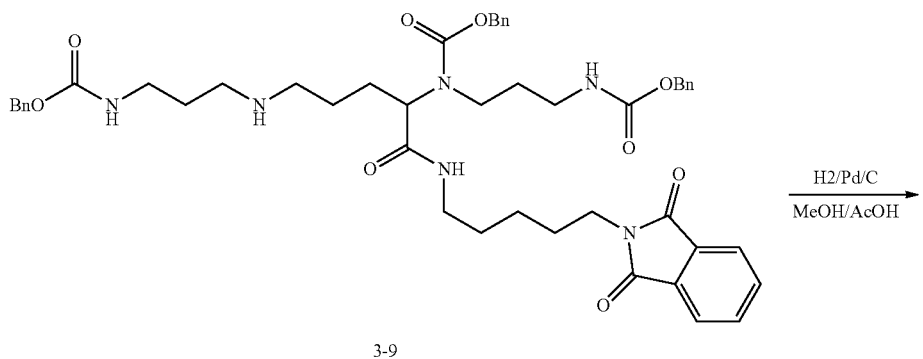
3-9
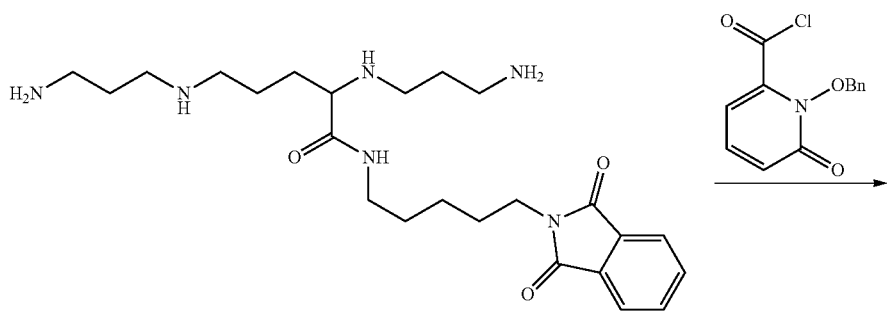
3-10

-continued

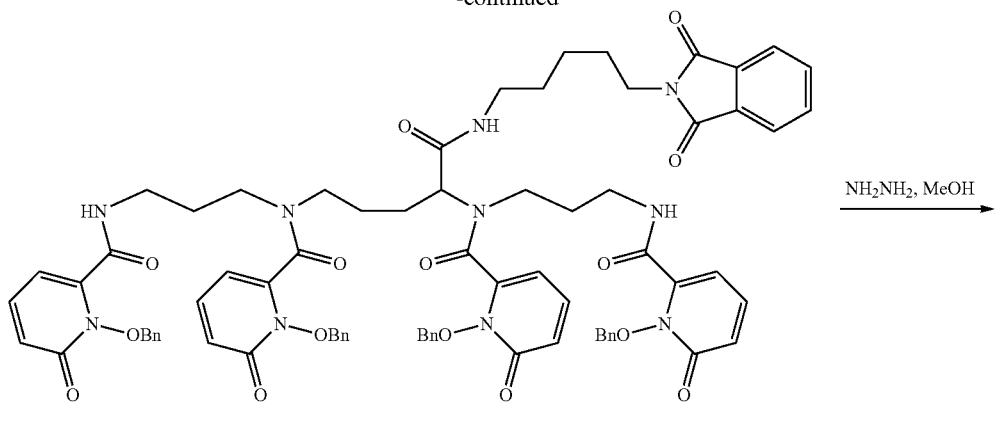

3-11

NH₂NH₂, MeOH

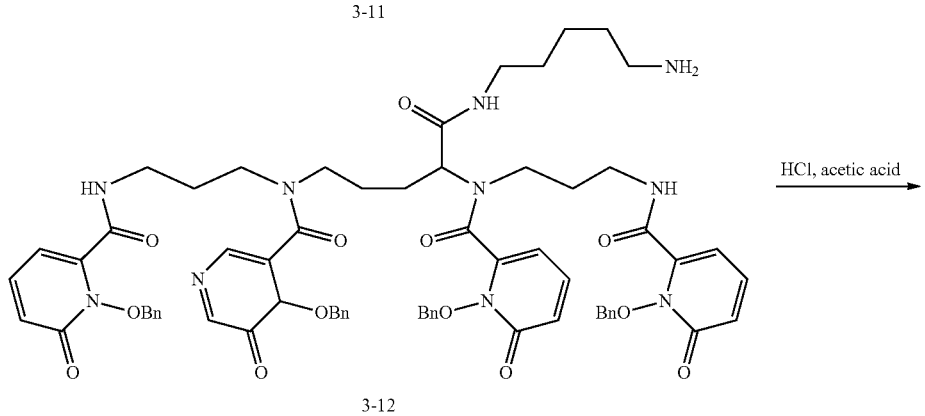

3-12

HCl, acetic acid

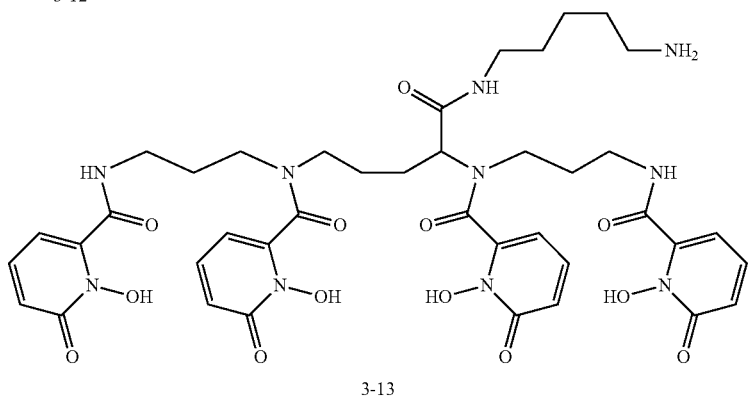

3-13

N-[5-(Bromo)pentyl]phthalimide (3-1)

This is a known compound; Blatt, A. H.; Gross, Norma; J. Amer. Chem. Soc. 1953, 75, 1245-7.

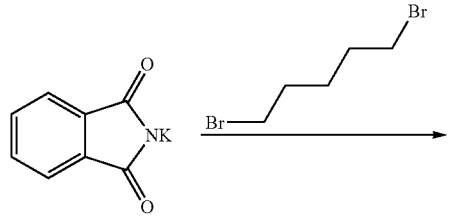

-continued

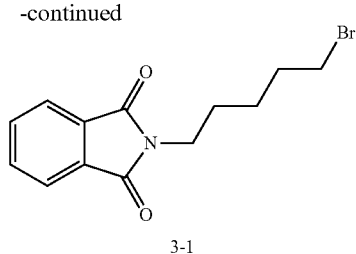

3-1

To a solution of 1,3-dibromopropane (30.3 g, 150.1 mmol) in acetone (150.0 mL) was added potassium phthalimide (9.3 g, 50.2 mmol). The resulting mixture was refluxed for 10 hrs, and then cooled to room temperature. After filtering the precipitated potassium bromide, the filtrate was concentrated under reduced pressure to viscous

N-(5-Azidopentyl) phthalimide (3-2)

This is a know compound. Lee, Lac V.; Mitchell, Michael L.; Huang, Shih-Jung; Fokin, Valery V.; Sharpless, K. Barry; Wong, Chi-Huey; J. Amer. Chem. Soc. 2003, 125(32), 9588-9589.

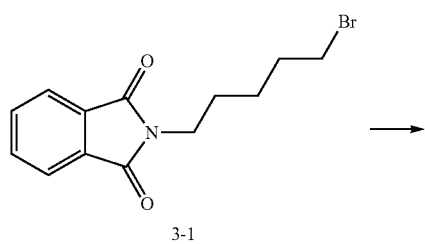

3-1

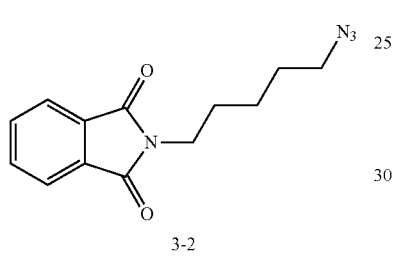

3-2

Compound 3-1 (5.0 g, 17 mmol) was dissolved in dimethylformamide (DMF, 30 mL), and sodium azide (1.4 g, 1.3 eq.) was added. The reaction mixture was allowed to stir overnight, whereupon it was concentrated in vacuo to yield a white residue. The residue was dissolved in DCM, filtered through a silica gel plug, and solvent removed to afford N-[5-(azido)butyl]phthalimide (4.0 g, 91%) as a colorless thick oil.

$^1$H NMR (300 MHz, CDCl$_3$): δ=1.30-1.44 (m, 2H), 1.50-1.75 (m, 4H), 3.21 (t, J=7.5 Hz, 2H), 3.63 (t, J=7.5 Hz, 2H), 7.60-7.70 (m, 2H), 7.75-7.80 (m, 2H).

$^{13}$C NMR (75 MHz CDCl$_3$): δ=23.8, 27.9, 28.2, 37.4, 51.0, 123.0, 131.9, 133.7, 168.2.

N-(5-Aminopentyl) phthalimide HCl Salt (3-3)

This is a know compound. Reinhardt, Gerd; Journal of Applied Biochemistry 1980, 2(6), 495-509.

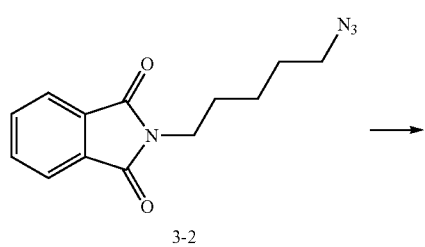

3-2

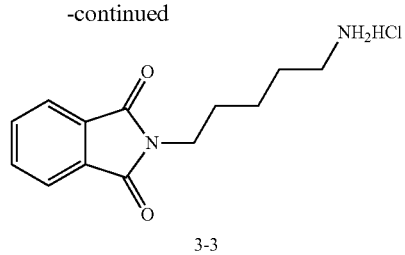

3-3

N-[5-(Azido)butyl]phthalimide (4.0 g, 15.5 mmol) was dissolved in methanol (50 mL) and glacial acetic acid (2 g). Palladium on carbon (10%, 400 mg) was added, and the suspension was hydrogenated at 500 psi for 12 hr. The reaction mixture was filtered, acidified to pH 4, and the filtrate was concentrated in vacuo to yield compound 3-3 as an amorphous white solid (3.8 g, 92%).

$^1$H NMR (300 MHz, CDCl$_3$): δ=1.30-1.44 (m, 2H), 1.60-1.75 (m, 4H), 2.88 (t, J=7.5 Hz, 2H), 3.62 (t, J=7.5 Hz, 2H), 7.75 (m, 4H).

$^{13}$C NMR (75 MHz CDCl$_3$): δ=24.8, 28.1, 29.2, 38.5, 40.7, 124.2, 133.4, 135.5, 169.9.

PhthalC5-Z-Boc-Ornithine (3-4)

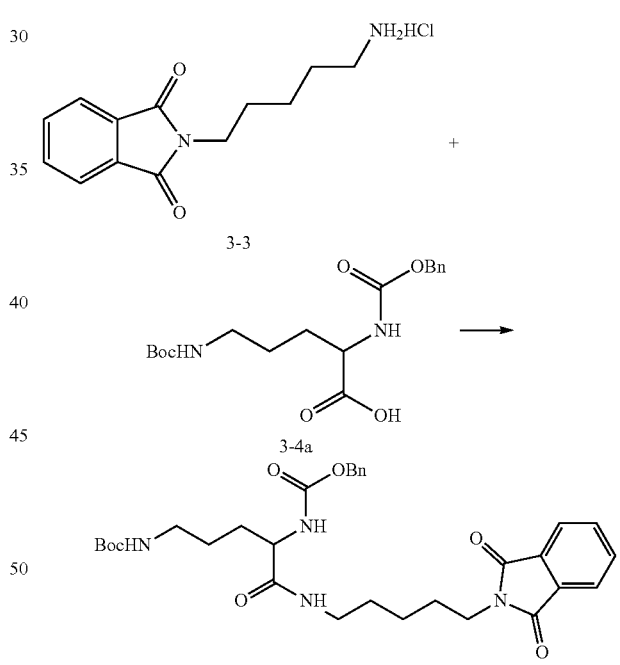

Compound 3-4a (7.3 g, 20 mmol) was dissolved in anhydrous THF (40 mL) and the solution was cooled to −20° C. under nitrogen. N-methyl morpholine (NMM, 2.4 mL, 22 mmol) was added and the solution was stirred for 10 min. iso-Butyl chloroformate (2.8 mL, 21 mmol) was added to the cold solution via syringe slowly and the solution was stirred at −10° C. for 45 min. The mixture was then cooled to −40° C. and a solution of N-(5-aminopentyl)phthalimide HCl salt (compound 3-3, 5.9 g, 22 mmol) and NMM (2.4 mL, 22 mmol) in DMF (20 mL) was added dropwise via a Teflon tube. The mixture was stirred at −40° C. for 20 min and then allowed to warm to room temperature slowly, and stirred for another 8 hr. The reaction mixture was evaporated to dryness, and the residue dissolved in DCM (50 mL). This was washed with aqueous 10% citric acid (2×30 mL) and 5% KHCO₃ solution (2×30 mL) successively. The organic phase was concentrated and purified by flash silica gel chromatography using a gradient of methanol in DCM to provide compound 3-4 as a semisolid material (9.9 g, 85%).

PhthalC5-N$^\varepsilon$-Boc-Ornithine HOAc Salt (3-5)

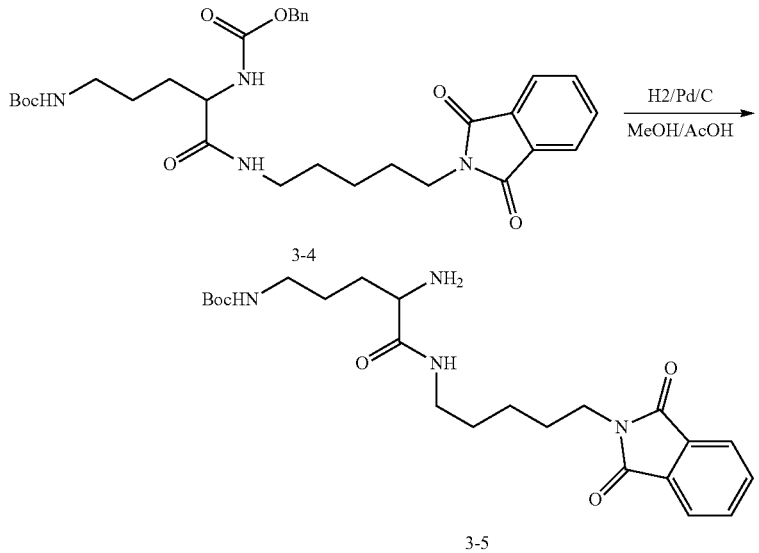

Compound 3-4 (5.8 g, 10 mmol) and Pd/C catalyst (0.6 g, 10 wt. % palladium on activated carbon (Aldrich)) were combined in methanol (40 mL) and glacial acetic acid (1 mL). The mixture was hydrogenated (500 psi pressure, room temperature) overnight in a Parr bomb. After removing the catalyst by filtration, the filtrate was evaporated to dryness to provide compound 3-5 as pale yellow oil (4.65 g, 92%).

PhthalC5-ZC3-N$^\varepsilon$-Ornithine

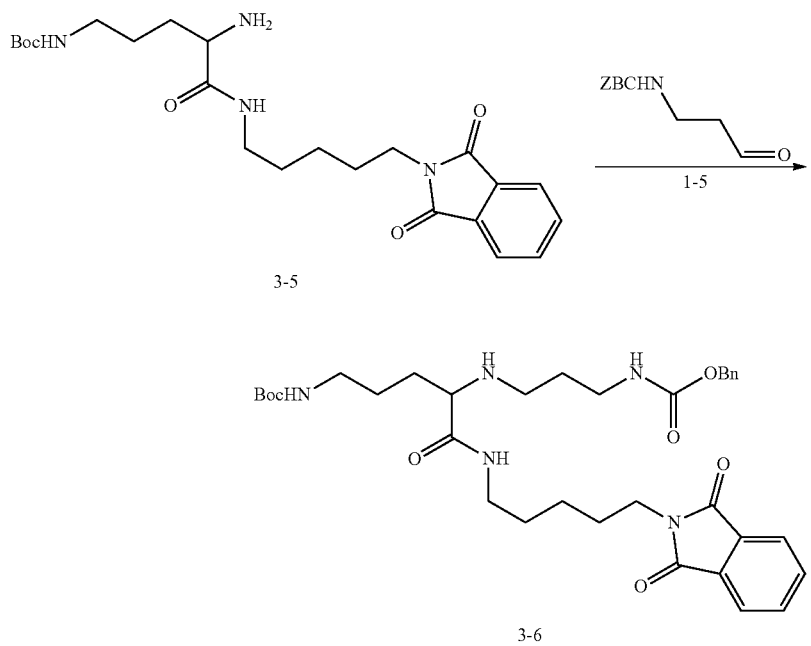

Compound 3-5 (2.5 g, 5 mmol) and CBz-propylaldehyde (compound 1-5, 1.1 g, 5.3 mmol) were mixed in THF (20 mL) at room temperature under $N_2$. After 3 hrs, sodium triacetoxyborohydride (2.1 g, 10 mmol) was added and the mixture stirred at room temperature under a $N_2$ atmosphere for 24 h. A mixture of acetic acid and MeOH (1:1, 20 mL) was added to quench the reaction and the mixture was evaporated to dryness. The residue was dissolved in DCM and loaded onto a flash silica gel column. The appropriate fractions of a gradient elution were combined and evaporated to dryness to provide compound 3-6 as a thick oil (1.8 g, 56%).

PhthalC5-Z2C3-$N^\varepsilon$-Ornithine

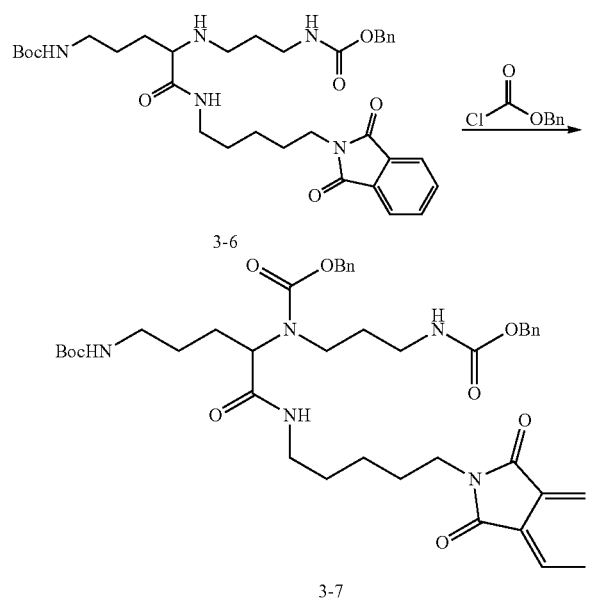

A solution of compound 3-6 (2.6 g, 4 mmol) in DCM (30 mL) was mixed with 20% $Na_2CO_3$ solution (10 mL) while cooling with an ice bath. To this vigorously stirred mixture a solution of benzylchloroformate (0.86 g, 5 mmol) in DCM (20 mL) was added dropwise. The mixture was warmed to room temperature and stirred overnight when TLC indicated the reaction was complete. The volatiles were removed in vacuo, and the residue was purified by flash silica gel chromatography using 2-6% methanol in DCM to provide compound 3-7 (2.6 g, 85%) as thick pale yellow oil.

PhthalC5-Z2-Spermidine (3-8)

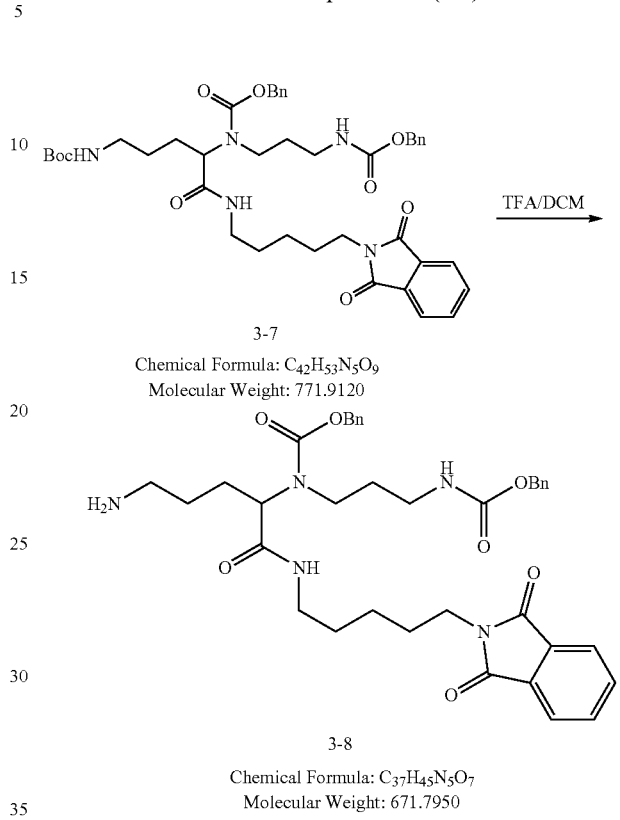

Compound 3-7 (1.54 g, 2 mmol) and few drops of triisopropylsilane were dissolved in 25% TFA in DCM (15 mL) with stirring. After 3 hours, TLC revealed the reaction was complete. The volatiles were removed under reduced pressure and the residue was dissolved in DCM and washed with saturated aqueous $K_2CO_3$ solution (10 mL). The organic phase was then purified by chromatography on basic alumina, using 7% MeOH in DCM as eluent. Fractions containing product were combined and solvent removed under reduced pressure to provide compound 3-8 as thick beige colored oil (1. g, 81%).

PhthalC5-Z3-Spermine (3-9)

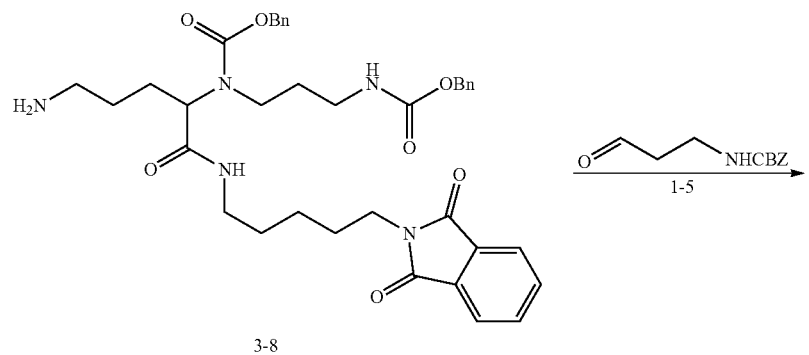

-continued

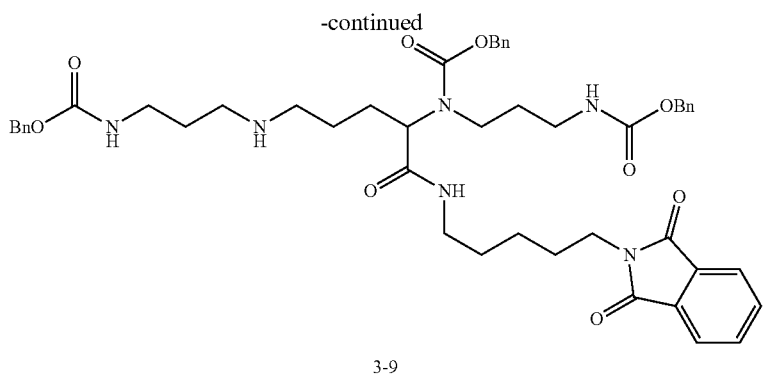

3-9

Compound 3-8 (0.84 g, 1.25 mmol) and compound 1-5 (0.27 g, 1.3 mmol) were mixed in THF (10 mL) at room temperature under $N_2$. The mixture was stirred for 3 hrs, sodium triacetoxyborohydride (0.4 g, 2 mmol) was added, and the mixture stirred at room temperature under a $N_2$ atmosphere for 24 h. A mixture of acetic acid and MeOH (1:1, 10 mL) was added to quench the reaction and the mixture was evaporated to dryness. The residue was dissolved in DCM and purified by flash silica gel chromatography using 3-10% methanol in DCM as eluent. Fractions containing product were collected and evaporated to dryness to provide compound 3-9 as pale beige thick oil (0.76 g, 71%).

PhthalC5-Spermine (3-10)

Compound 3-9 and Pd/C catalyst (10 wt. % palladium on activated carbon (Aldrich)) are combined in methanol. The mixture is hydrogenated (500 psi pressure, room temperature) overnight in a Parr bomb. After removing the catalyst by filtration, the filtrate is evaporated to dryness to provide compound 3-10.

PhthalC5-Spermine-1,2-HOPOBn (3-11)

To a vigorously stirred suspension of the raw PhthalC5-Spermine (compound 3-10) in DCM and an aqueous solution of $K_2CO_3$, cooled with an ice bath, is added slowly a solution of 1,2HOPOBn chloride in dry DCM. After the addition is complete the ice bath is removed and the reaction is stirred overnight. The organic phase is separated, the solvent is evaporated, and the crude product is purified by flash silica gel column chromatography to afford compound 3-11.

$NH_2$C5-Spermine-1,2-HOPOBn (3-12)

To a stirred suspension of PhthalC5-Spermine-1,2-HOPOBn (compound 3-11) in MeOH is added hydrazine hydrate. The solution is heated at reflux for one hour, allowed to cool, the solvent is evaporated, and the crude product is purified by flash silica gel column chromatography to afford compound 3-12.

$NH_2$C5-Spermine-1,2-HOPO (3-13)

$NH_2$C5-Spermine-1,2-HOPOBn (compound 3-12) and triisopropylsilane are dissolved in a mixture of concentrated HCl (12 M) and glacial acetic acid (1:1). The mixture is stirred at room temperature for 3 days. The volatiles are removed under reduced pressure, and the residue is dissolved in a minimum amount of methanol and precipitated by addition of isopropyl alcohol. The resulting precipitate is collected by filtration and dried under vacuum to provide compound 3-13 as the hydrochloride salt.

Example 5. Side-Functionalized 3,4,3-LI-1,2-HOPO with Amino Group

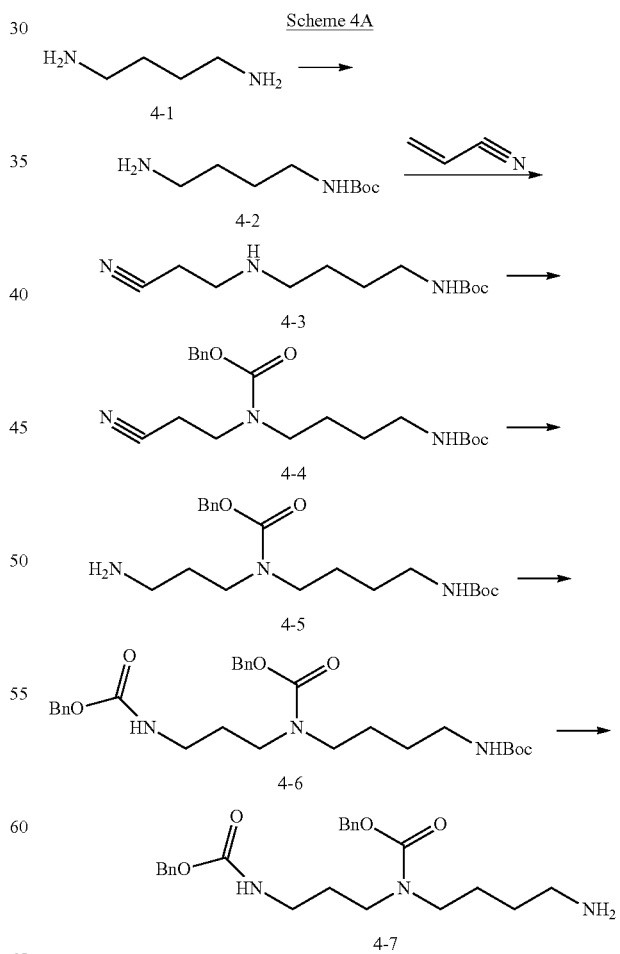

Scheme 4B
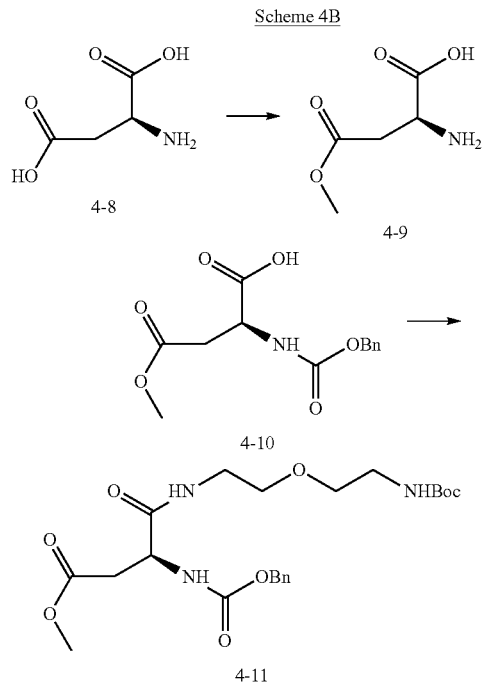
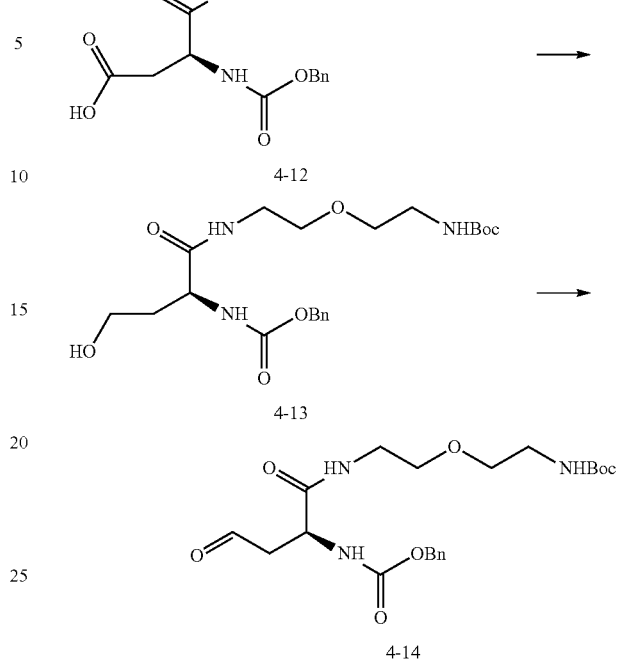
Scheme 4C
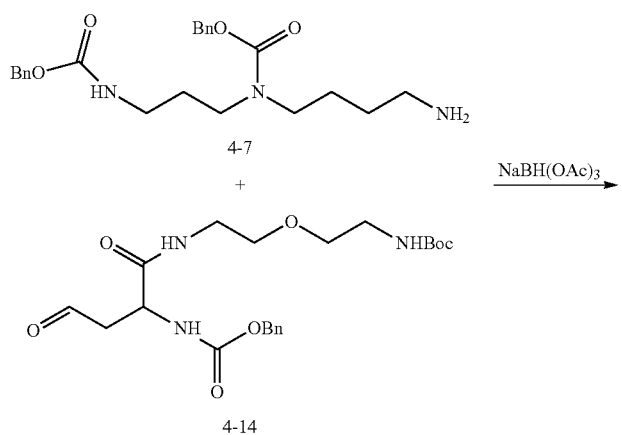
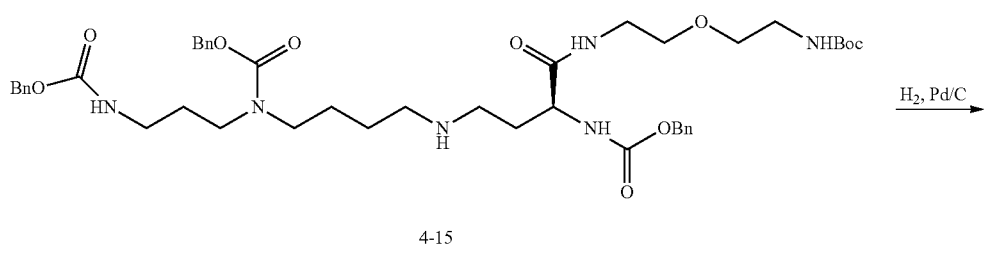

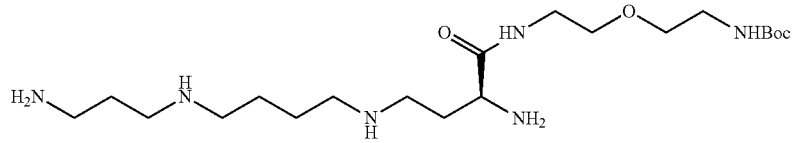
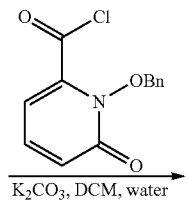

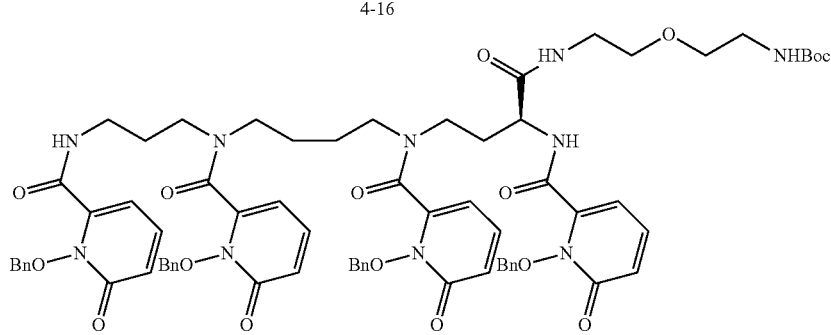

Synthesis of 4-7 (Scheme 4 Part A)

MonoBoc4LI-amine (4-2)

This is a known compound. Ryszard Andruszkiewicz, Michał Radowski, and Zbigniew Czajgucki; Synthetic Communications, 2005, 35: 1085-1094.

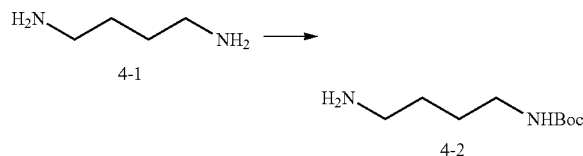

Sodium hydroxide solution (28%, 23 mL) was added to 1,4-butanediamine (20 g, compound 4-1) in a 500 mL round bottom flask. After the butanediamine was completely dissolved, di-tert-butylpyrocarbonate [(Boc)₂O, 200 mL, 12.5% ethanolic solution] was added dropwise to the reaction solution at room temperature with stirring. After the reaction was completed, the reaction solution was concentrated by rotary evaporation to remove ethanol, and extracted with DCM (6×50 mL). The organic layers were combined, neutralized with 2N HCl to pH 5 and washed with water (2×50 mL) and saturated salt water (50 mL) successively to remove the residual butanediamine. The organic phase was then washed with saturated aqueous K₂CO₃ solution and purified by chromatography using a strongly basic alumina column and MeOH/DCM as eluents. After concentration, compound 4-2 was obtained as a colorless oil-like substance (12.8 g, 60%).

tert-Butyl (4-((2-cyanoethyl)amino)butyl)carbamate (4-3)

This is a known compound. Ryszard Andruszkiewicz, Michał Radowski, and Zbigniew Czajgucki; Synthetic Communications, 2005, 35: 1085-1094.

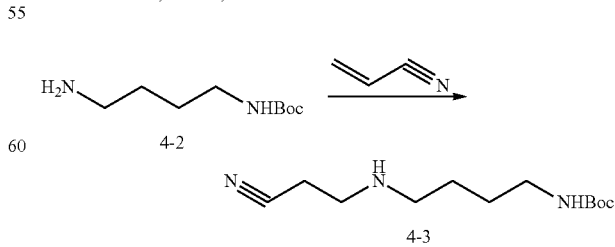

Compound 4-2 (13 g) was dissolved in methanol (60 mL), and added dropwise to a solution of acrylonitrile (6 mL) and methanol (20 mL) at room temperature with stirring and monitored via TLC. After the reaction was judged to be complete, the reaction solution was concentrated by rotary evaporation, and compound 4-3 was obtained as a colorless oil-like substance (15.8 g, 95%).

Benzyl (4-((tert-butoxycarbonyl)amino)butyl)(2-cyanoethyl)carbamate (4-4)

This is a known compound. Ryszard Andruszkiewicz, Michał Radowski, and Zbigniew Czajgucki; Synthetic Communications, 2005, 35: 1085-1094.

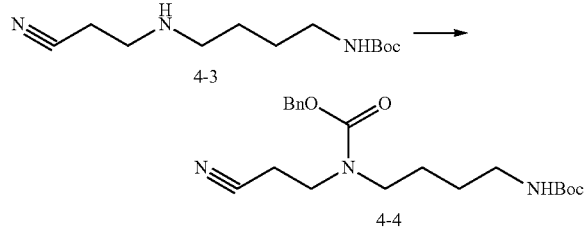

To a solution of compound 4-3 (15 g) in THF (80 mL) and triethylamine (13 mL) in a 250 mL round bottom flask was added dropwise a solution of benzylchloroformate (10.5 mL) and THF (30 mL) at room temperature with stirring at room temperature. After the reaction was judged to be complete using TLC, the volatiles were removed, the residue was dissolved in ethyl acetate (100 mL) and washed sequentially with 1 mol/L HCl solution (3×30 mL), water, and saturated salt water. The solution was dried with anhydrous sodium sulfate and purified by flash silica gel chromatography. Fractions containing product were combined and solvent removed under reduced pressure. The residual oil was triturated with petroleum ether. The white precipitate that formed was separated by filtration, and washed with petroleum ether. After air drying, compound 4-4 was obtained as a white solid (20 g, 85%).

Benzyl (3-aminopropyl)(4-((tert-butoxycarbonyl)amino)butyl)carbamate (4-5)

This is a known compound. Ryszard Andruszkiewicz, Michał Radowski, and Zbigniew Czajgucki; Synthetic Communications, 2005, 35: 1085-1094.

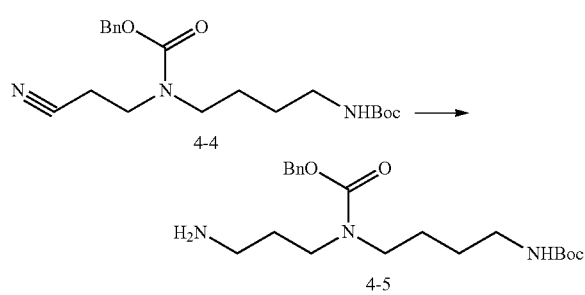

A solution of compound 4-4 (15 g) in methanol saturated with ammonia (120 mL) was placed into a Parr bomb, and Raney nickel (4.5 g) was added. The bomb was charged with hydrogen (1000 psi) and heated in a 50° C. oil bath for 24 h. The reaction solution was filtered thru Celite® in a glass fritted funnel. After concentration, compound 4-5 was obtained as light blue oil (13.6 g, 92%).

Benzyl (3-(((benzyloxy)carbonyl)amino)propyl)(4-((tert-butoxycarbonyl)amino)butyl)-carbamate (4-6)

This is a known compound. Ryszard Andruszkiewicz, Michał Radowski, and Zbigniew Czajgucki; Synthetic Communications, 2005, 35: 1085-1094.

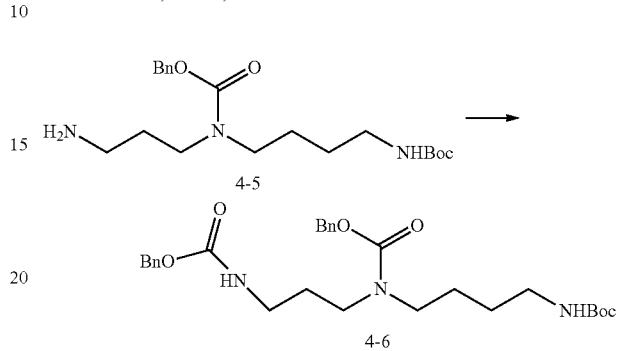

A mixture of compound 4-5 (13 g) in 20% $K_2CO_3$ aqueous solution (30 mL) and DCM (30 mL) a 125 ml long neck round bottom flask was cooled in an ice bath. A solution of benzyl chloroformate (10.5 mL) in DCM (30 mL) was added dropwise with vigorous. After the reaction was judged to be complete by TLC, the organic phase was separated and loaded onto a flash silica column. Compound 4-6 was isolated following gradient elution as a white solid, in 85% yield.

Benzyl (4-aminobutyl)(3-(((benzyloxy)carbonyl)amino)propyl)carbamate (4-7)

This is a known compound, Almeida, M. Lurdes S.; Grehn, Leif, Ragnarsson, Ulf; Acta Chemica Scandinavica 1989, 43(10), 990-4.

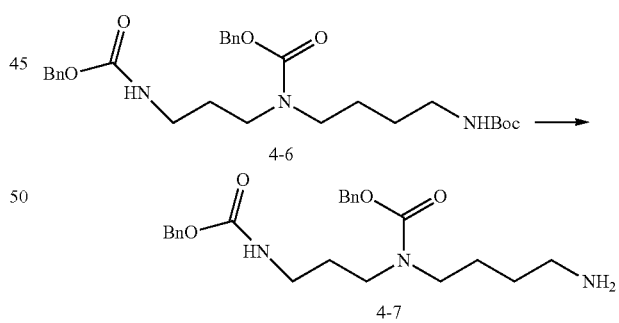

Compound 4-6 (5.2 g, 10 mmol) and few drops of triisopropylsilane were dissolved in 25% TFA in DCM (20 mL) with stirring. After 3 hours, the reaction was judged to be complete using TLC. The volatiles were removed under reduced pressure, the residue was dissolved in DCM, and washed with saturated aqueous $K_2CO_3$ solution (10 mL). The organic phase was then applied to a plug of basic alumina; the compound was then eluted with 7% MeOH in DCM. The combined DCM fractions were evaporated to dryness to provide compound 4-7 as thick beige colored oil (3.5 g, 83%).

Synthesis of Compound 4-14 (Scheme 4 Part B)

L-Aspartic Acid β-methyl ester hydrochloride (4-9)

This is a known compound. Martin, J. H.; Hausmann, W. K. *J. Amer. Chem. Soc.* 1960, 82, 2079.

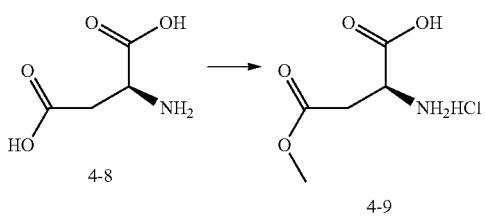

A suspension of L-aspartic acid (compound 4-8, 10.0 g, 75.1 mmol) in 50 mL methanol was treated with thionyl chloride (8.94 g, 75.1 mmol) at 0° C. The reaction mixture was stirred at 0° C. for 30 min, then at ambient temperature for 2 hrs. The resulting clear solution was diluted with diethyl ether (200 mL) with rapid stirring. A white precipitate formed which was collected by vacuum filtration, washed with diethyl ether and dried to yield compound 4-9 (10.7 g, 78%).

Z-Aspartic Acid-β-methyl ester (4-10)

This is a known compound. Goodman, Murray; Boardman, Franklin; J. Amer. Chem. Soc. 1963, 85, 2483-90.

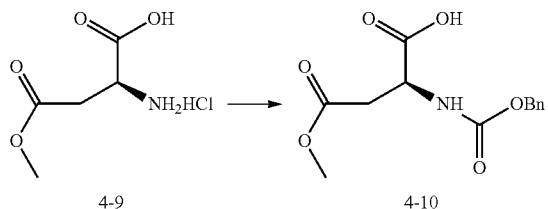

The crude compound 4-9 (9.8 g, 53 mmol) was dissolved in water (115 mL) and dioxane (53 mL), and cooled to 0° C. Na$_2$CO$_3$ (5.6 g, 53 mmol) was added, followed by benzyl chloroformate (9.1 g, 53.4 mmol) in dioxane (63 mL) dropwise over 3 h. The reaction mixture was stirred at ambient temperature overnight. The solution was washed with ethyl acetate (3×50 mL). The aqueous layer was acidified to pH 2 with 6 M HCl. The product was extracted with ethyl acetate (2×50 mL). The combined organic extracts were washed with brine (50 mL), dried over Na$_2$SO$_4$ and the solvent was evaporated under reduced pressure. The crude compound was passed through a short pad of silica gel using ethyl acetate and concentrated to provide compound 4-10 as a semi-solid (78%).

$^1$H NMR (300 MHz, CDCl$_3$): δ 7.89 (s, 1H, OH), 7.39-7.24 (m, 5H, H(Ph)), 5.96 (br d, J=9.0 Hz, 1H, NH), 5.10 (s, 2H, CH$_2$-Ph), 4.72-4.59 (m, 1H, CHN), 3.64 (s, 3H, OCH$_3$), 3.02 (dd, J=17.3, 4.56 Hz, 1H, CH$_2$—CO), 2.85 (dd, J=17.3, 4.56 Hz, 1H, CH$_2$—CO); $^{13}$C NMR (75 MHz, CDCl$_3$): δ 174.0, 171.5, 156.1, 135.9, 128.4, 128.1, 128.0, 67.2, 52.0, 50.1, 36.2.

Methyl (S)-13-(((benzyloxy)carbonyl)amino)-2,2-dimethyl-4,12-dioxo-3,8-dioxa-5,11-diazapentadecan-15-oate (4-11)

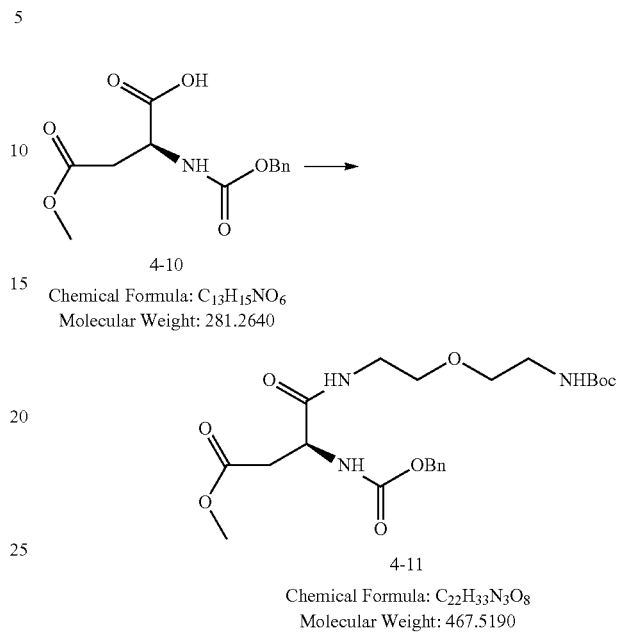

4-10
Chemical Formula: C$_{13}$H$_{15}$NO$_6$
Molecular Weight: 281.2640

4-11
Chemical Formula: C$_{22}$H$_{33}$N$_3$O$_8$
Molecular Weight: 467.5190

Compound 4-10 (7.9 g, 28 mmol) was dissolved in anhydrous THF (60 mL) and the solution was cooled to −20° C. under nitrogen. N-methyl morpholine (NMM, 3.4 mL, 31 mmol) was added and the solution was then stirred for 10 min. iso-Butyl chloroformate (3.7 mL, 29 mmol) was added to the cold solution via syringe slowly and the solution was stirred at −10° C. for 45 min. The mixture was cooled to −40° C. and a solution of Boc-5LIO-amine HCl salt (compound 2-4, 6.9 g, 29 mmol) and NMM (3.2 mL) in DMF (40 mL) was added dropwise via a Teflon tube. The mixture was stirred at −40° C. for 20 min and then allowed to warm to room temperature slowly, and stirred for another 8 hr. The reaction mixture was then evaporated to dryness, and dissolved in DCM (50 mL), and washed with aqueous 10% citric acid (2×30 mL) and 5% KHCO$_3$ solution (2×30 mL) successively. The organic phase was applied to a flash silica column and purified by gradient elution using methanol in DCM to provide compound 4-11 as a semisolid material (10.5 g, 81%).

(S)-13-(((Benzyloxy)carbonyl)amino)-2,2-dimethyl-4,12-dioxo-3,8-dioxa-5,11-diazapenta-, decan-15-oic acid (4-12)

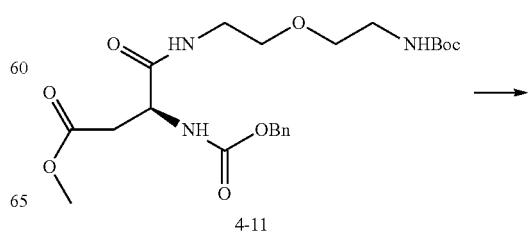

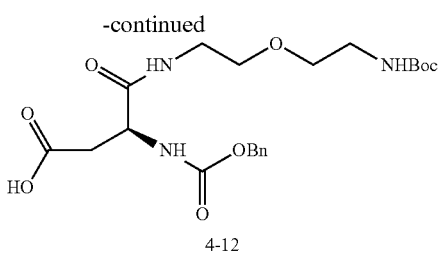

4-12

To a cold solution of compound 4-11 (4.7 g, 10 mmol) in methanol (30 mL) cooled in an ice bath was added aqueous NaOH solution (1 N, 12 mL). The solution was stirred under $N_2$ until TLC indicated that the reaction was complete. The methanol was removed under reduced pressure. The remaining solution was acidified with 0.2 N HCl to pH 5. The reaction mixture was evaporated to dryness. The residue was dissolved in dry DCM, and insoluble inorganic salts were removed by filtration. The filtrate was then evaporated to dryness to provide compound 4-12 as a white foam (90%).

Boc-5LIO—$N^\alpha$—Z-Aspartinol (4-13)

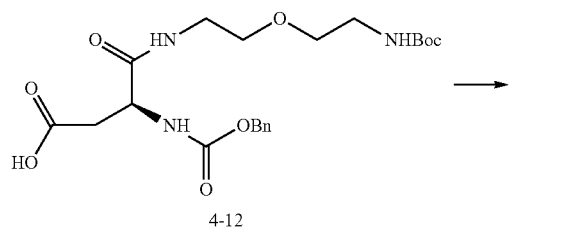

To a cold (−15° C.) solution of compound 4-12 (2.25 g, 4.8 mmol) in THF (20 mL) were successively added N-methyl morpholine (0.55 mL, 5 mmol) and isobutyl chloroformate (0.67 mL, 4.9 mmol). After 5 min., the precipitated N-methyl morpholine hydrochloride salt was removed by filtration, washed with THF (5×2 mL) and the filtrate and washings were combined in a 1 liter flask cooled with an ice-salt bath. A solution of sodium borohydride (1 g) in water (10 mL) was added via a Teflon cannula, producing a strong evolution of gas. The reaction mixture was stirred for 4 hours, and evaporated to dryness. The residue was extracted with DCM three times and the combined organic extracts were applied to a flash silica gel column that was eluted using MeOH in DCM to provide compound 4-13 as thick oil (80%).

Boc-5LIO—$N^\alpha$—Z-Aspartinal (4-14)

Boc-5LIO—$N^\alpha$—Z-aspartinol (4-13) and 2,2,6,6-tetramethylpiperidine 1-oxyl (TEMPO) in dichloromethane are added to a solution of $NaIO_4$ and NaBr in water. After stirring for 12 hrs at ambient temperature, the organic layer is separated, washed with 10% $Na_2S_2O_3$ and dried over $MgSO_4$. The solvent is removed in vacuo and the residue is recrystallized from $Et_2O$/n-hexane providing the aldehyde 4-14.

Boc5LIO-Spermine-Z4 (4-15)

Compound 4-7 and compound 4-14 are mixed in THF at room temperature under $N_2$. The mixture is stirred for 3 hrs, then sodium triacetoxyborohydride is added and the mixture stirred at room temperature under a $N_2$ atmosphere for 24 hrs. A mixture of acetic acid and MeOH (1:1) is added to quench the reaction, the mixture is evaporated to dryness, the residue dissolved in DCM, and loaded onto a flash silica gel column. The appropriate fractions of a gradient elution (3-10% methanol in DCM) are collected and evaporated to dryness to provide compound 4-15.

Boc5LIO-Spermine (4-16)

Compound 4-15 and Pd/C catalyst (palladium, 10 wt. % on activated carbon (Aldrich)) are combined in methanol. The mixture is hydrogenated (500 psi pressure, room temperature) overnight in a Parr bomb. After removing the catalyst by filtration, the filtrate is evaporated to dryness to provide compound 4-16.

Boc-5LIO-Spermine-1,2-HOPOBn (4-17)

To a vigorously stirred suspension of compound 4-16 in DCM and an aqueous solution of $K_2CO_3$, cooled with an ice bath, is added slowly a solution of 1,2HOPOBn chloride (made from 1,2-HOPOBn acid) in dry DCM over 30 min. After the addition is complete the ice bath is removed and the reaction is stirred overnight. The organic phase is separated, the solvent is evaporated, and the crude product is purified by flash silica gel column chromatography to afford compound 4-17.

5LIO-Spermine-1,2-HOPO (4-18)

Boc5LIO-Spermine-1,2-HOPOBn (compound 4-17) and triisopropylsilane are dissolved in a mixture of concentrated HCl (12 M) and glacial acetic acid (1:1). The mixture is stirred at room temperature for 3 days. The volatiles are removed under reduced pressure and the residue is dissolved in a minimum amount of methanol and precipitated by addition of isopropyl alcohol. The precipitate is collected by filtration and dried under vacuum to provide compound 4-18.

Example 6: Synthesis of an Octacoordinating Spermine Bi-Functional 1,2-HOPO Chelator with Methoxy Substituted 6-Position

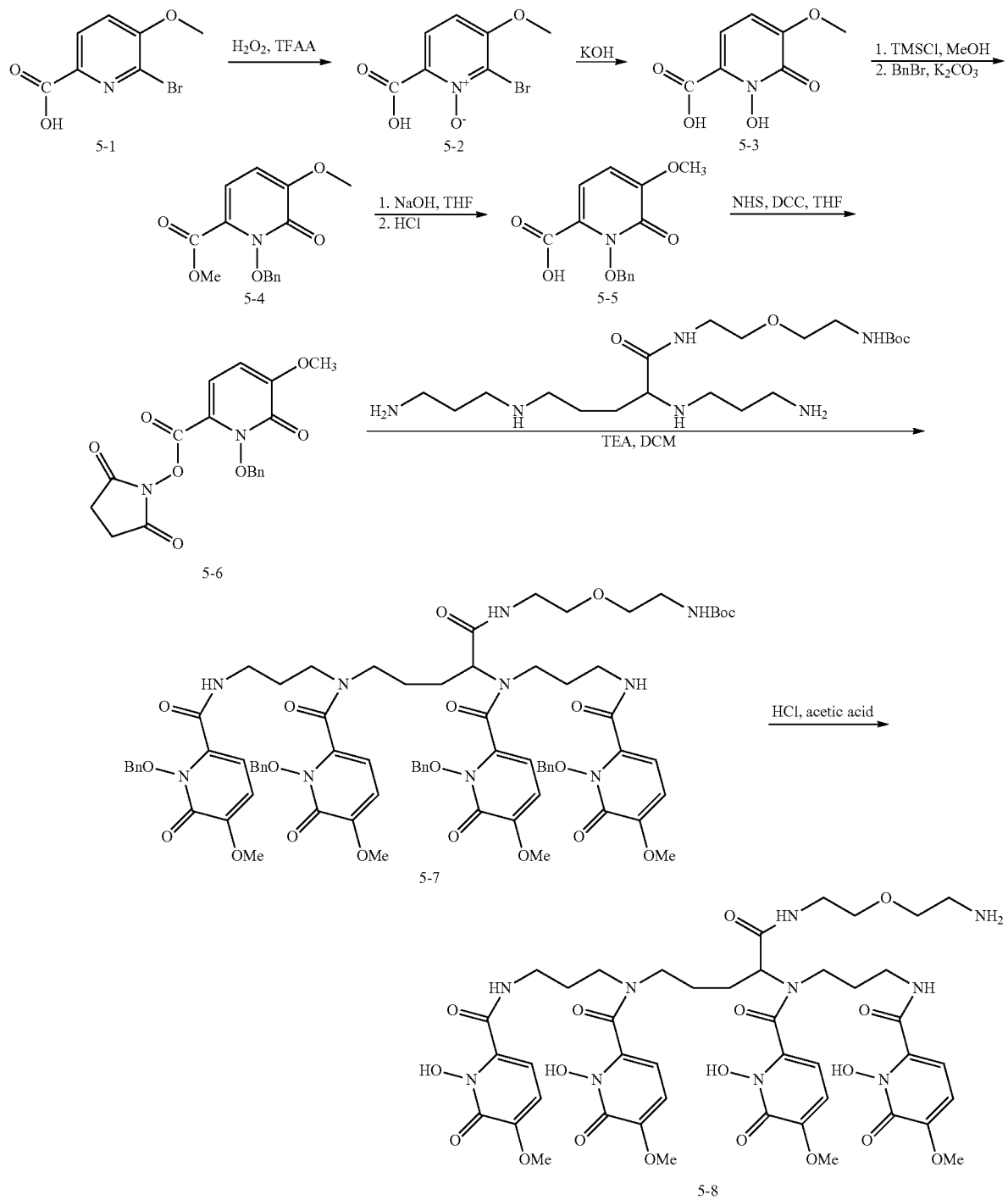

2-Bromo-3-methoxy-6-carboxypyridine-N-oxide 5-2. 2-Bromo-3-methoxy-6-pyridinecarboxylic acid 5-1 was prepared as previously described (Kelly, T. R. and Lang, F. *J. Org. Chem.*, 1996, 61, 4623-4633). Compound 5-1 (1.000 g, 4.31 mmol) was dissolved in trifluoroacetic acid (24 mL) under inert atmosphere. Hydrogen peroxide, 30% aqueous solution (2.686 mL, 23.7 mmol) was added and the solution was heated to 80° C. for 12.5 hr. After cooling, water (6 mL) was added and solvents were removed under reduced pressure. Additional water (10 mL) was added, the resulting suspension was triturated for 1 hr, whereupon the solids were filtered using a fritted funnel, washed with water (3×5 mL) and dried in vacuo to provide 2-bromo-3-methoxy-6-carboxypyridine-N-oxide 5-2 (0.827 g, 79.5%). $^1$H NMR (300 MHz, DMSO-d6): δ=8.26 (d, 1H, ArH), 7.57 (d, 1H, ArH), 4.04 (s, 3H, OCH$_3$). $^{13}$C NMR (400 MHz, D20/NaOD): δ=167.5, 155.3, 142.0, 125.6, 121.6, 57.5.

1-Hydroxy-2-oxo-3-methoxy-6-pyridinecarboxylic acid 5-3. Compound 5-2 (800 mg, 3.23 mmol) was dissolved in 15% aqueous potassium hydroxide (13 mL) under inert atmosphere. The solution was heated to 80° C. for 44 hr. After cooling, the solution was filtered to remove solid contaminants, washing with water (5 mL). Concentrated hydrochloric acid (2.5 mL) was added to the filtrate, and the resulting suspension was triturated for 3 hr. The solids were filtered using a fritted funnel, washed with water (2×5 mL) and dried in vacuo to provide 1-hydroxy-2-oxo-3-methoxy-6-pyridinecarboxylic acid 5-3 (482 mg, 80.7%). TH NMR (300 MHz, DMSO-d6): δ=6.75 (d, 1H, ArH), 6.69 (d, 1H, ArH), 3.68 (s, 3H, OCH$_3$). $^{13}$C NMR (400 MHz, D2O, NaOD): δ=170.5, 156.2, 147.3, 139.7, 111.1, 103.0, 56.2.

1-Benzyloxy-2-oxo-3-methoxy-6-pyridinecarboxylic acid methyl ester 5-4. Compound 5-3 (300 mg, 1.62 mmol) was suspended in methanol (6 mL) under inert atmosphere. Chlorotrimethylsilane (2.06 mL, 16.2 mmol) was added, and the suspension was stirred for 51 hr. Solvents were removed under reduced pressure, potassium carbonate (671 mg, 4.86 mmol) was added, and the residue was dried in vacuo overnight. The mixture was suspended in anhydrous acetonitrile (9 mL), benzyl bromide (385 µL, 3.24 mmol) was added, and the suspension was heated at reflux for 4.5 hr. After cooling, solvents were removed under reduced pressure, the residue was dissolved in dichloromethane (10 mL), and washed with water (5 mL). The aqueous layer was washed with dichloromethane (2×5 mL), the combined dichloromethane extracts were concentrated under reduced pressure, and the product was purified by silica gel chromatography using 1 to 2% methanol in dichloromethane as eluent. Purified product was dried in vacuo to provide 1-benzyloxy-2-oxo-3-methoxy-6-pyridinecarboxylic acid methyl ester 5-4 (373 mg, 79.6%). $^1$H NMR (300 MHz, CDCl$_3$): δ=7.58 (m, 2H, ArH), 7.38 (m, 3H, ArH), 6.70 (d, 1H, ArH), 6.54 (d, 1H, ArH), 5.37 (s, 2H, CH2Ph), 3.89 (s, 3H, OCH3), 3.80 (s, 3H, OCH3). $^{13}$C NMR (300 MHz, CDCl$_3$): δ=160.5, 155.1, 154.7, 134.1, 130.5, 129.5, 129.4, 128.8, 109.5, 109.4, 78.7, 56.7, 53.1.

1-Benzyloxy-2-oxo-3-methoxy-6-pyridinecarboxylic acid 5-5. Compound 5-4 (373 mg, 1.29 mmol) was dissolved in tetrahydrofuran (6 mL) and deionized water (1 mL). Sodium hydroxide (1M, 1.934 mL, 1.934 mmol) was added and the solution was allowed to stir for 2 hours. Tetrahydrofuran was removed under reduced pressure and water (8 mL) was added. Hydrochloric acid (6 M, 322 µL) was added to form a precipitate that was extracted with 20% tetrahydrofuran in dichloromethane (2×10 mL). The combined organic extracts were washed with water (5 mL) and solvents were removed under reduced pressure. The resultant product was dried in vacuo to provide 1-benzyloxy-2-oxo-3-methoxy-6-pyridinecarboxylic acid 5-5 (354 mg, 99.7%). $^1$H NMR (300 MHz, MeOD): δ=7.46 (m, 2H, ArH), 7.27 (m, 3H, ArH), 6.81 (s, 2H, ArH), 5.25 (s, 2H, CH2Ph), 3.80 (s, 3H, OCH3). $^{13}$C NMR (400 MHz, MeOD): δ=162.6, 157.1, 155.1, 135.4, 131.4, 131.2, 130.3, 129.6, 112.3, 111.5, 79.8, 57.3.

1-Benzyloxy-2-oxo-3-methoxy-6-pyridinecarboxylic acid is converted to the N-hydroxysuccinimide ester derivative 5-6 using dicyclohexylcarbodiimide. Reaction with spermine amine prepared as described above provides the protected intermediate 5-7. Protective groups are removed using hydrochloric acid in acetic acid to provide the octa-coordinating 1,2-HOPO bi-functional chelator 5-8.

Example 7: Synthesis of an Octacoordinating Spermine Bi-Functional 1,2-HOPO Based Chelator with Amine Reactive Isothiocyanate Derivatized Linker

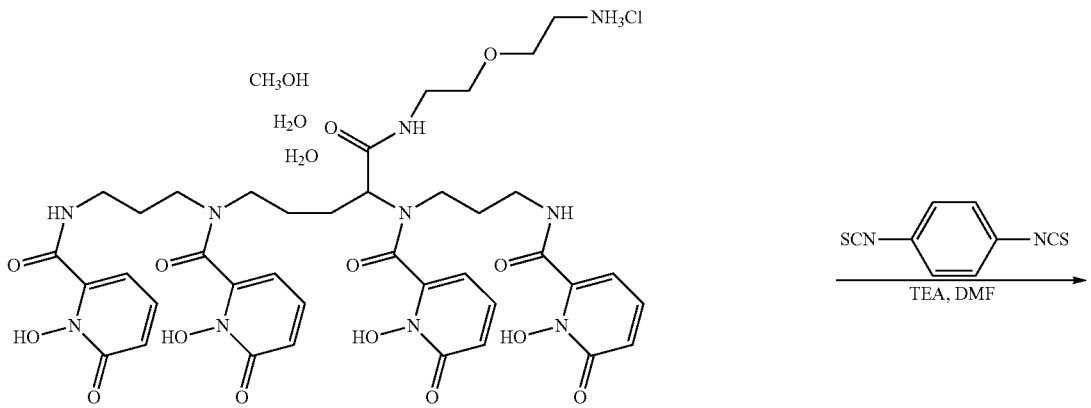

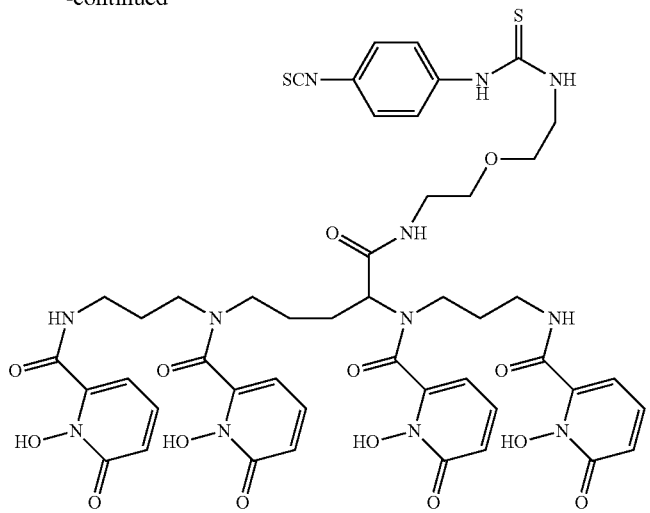

6-1

Octacoordinating Bifunctional Chelator, 4-Isothiocyanatophenylthiourea Derivative 6-1

Octacoordinating chelator 2-8 (5.51 mg, 5.59 µmol) was dissolved in dimethylformamide (50 µL) and triethylamine (11.3 µL). The solution was transferred to a microcentrifuge tube containing 1,4-phenyldiisothiocyanate (11.8 mg, 61.4 µmol) in dimethylformamide (150 µL) and mixed at 1000 rpm under inert atmosphere for 70 minutes. The solution was divided between two microtubes, and ether (ca. 1.8 mL per tube) was added. After 1 hr, the resulting suspension was centrifuged at 12,000 rpm for 3 minutes, decanted, the pellets were washed with ether (ca. 1.5 mL) and allowed to air dry. The pellets were dissolved in dimethylformamide (20 µL) and methanol (300 µL) and precipitated and washed with ether as described above. The pellets were dried in vacuo to provide 4-isothiocyanatophenylthiourea derivative 6-1 (3.91 mg, 65.2%). FTMS-pESI: calculated for $C_{47}H_{51}N_{12}O_{14}S_2$ $[M-H]^-$, 1071.3095, found, 1071.3146.

Example 8: Synthesis of Bifunctional Spermine Based MOE-TAM Chelators

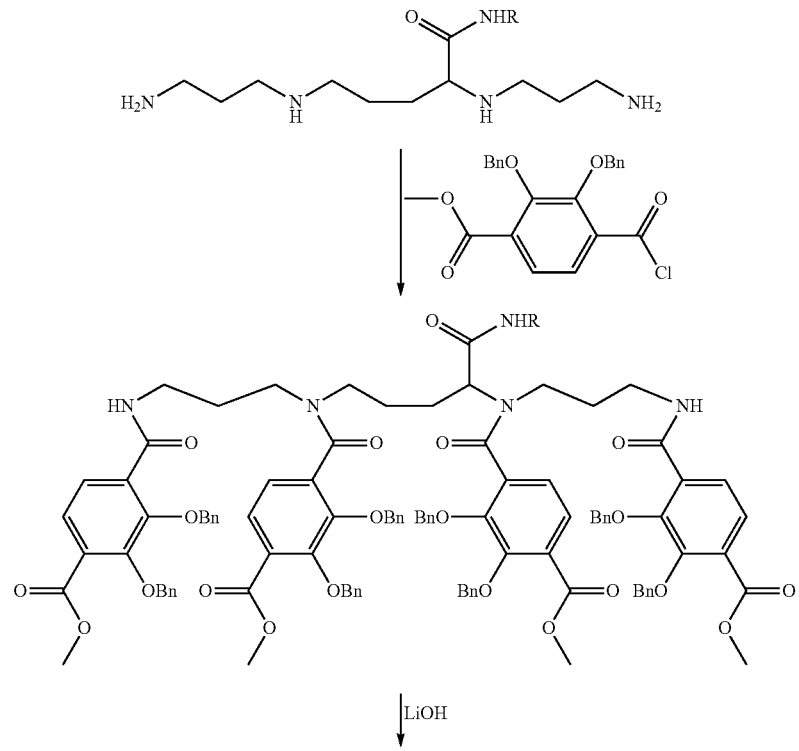

-continued
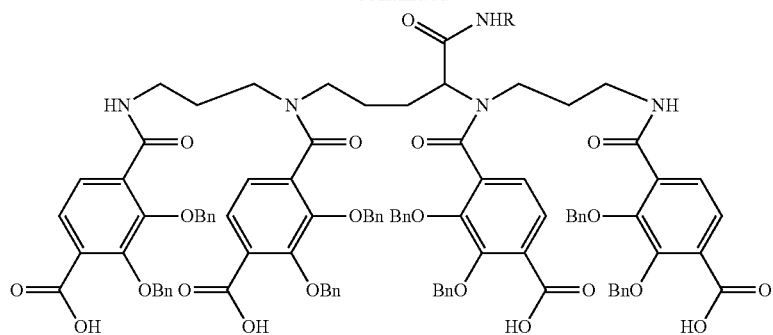
1. HATU, activation
2. H₂N–CH₂CH₂–OCH₃
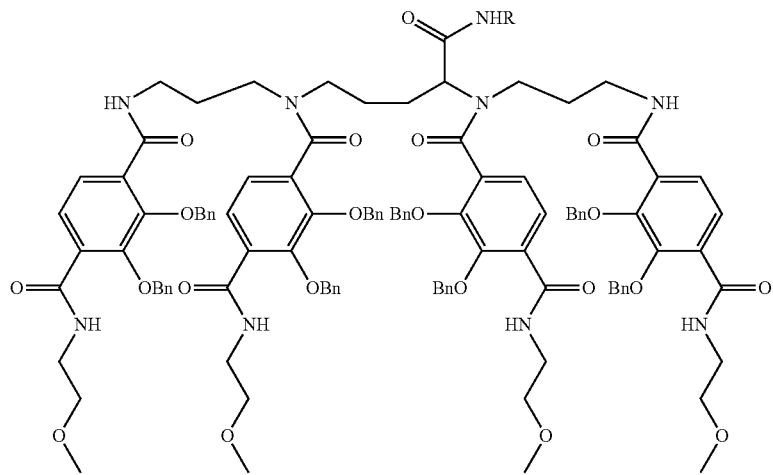
HCl/HOAC
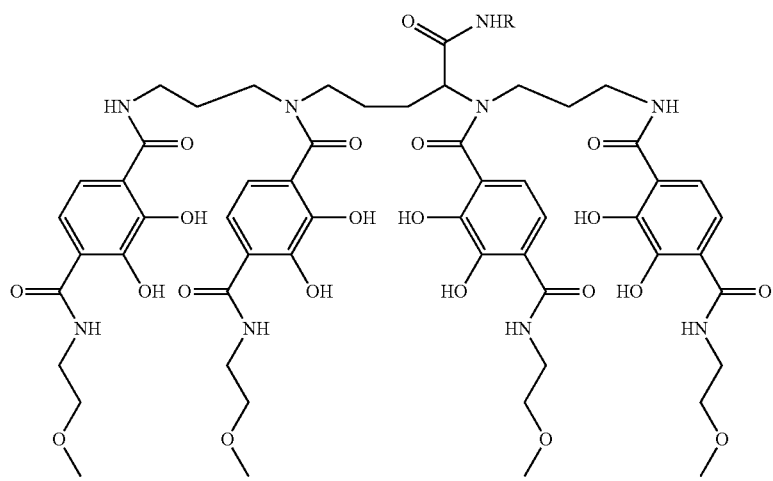

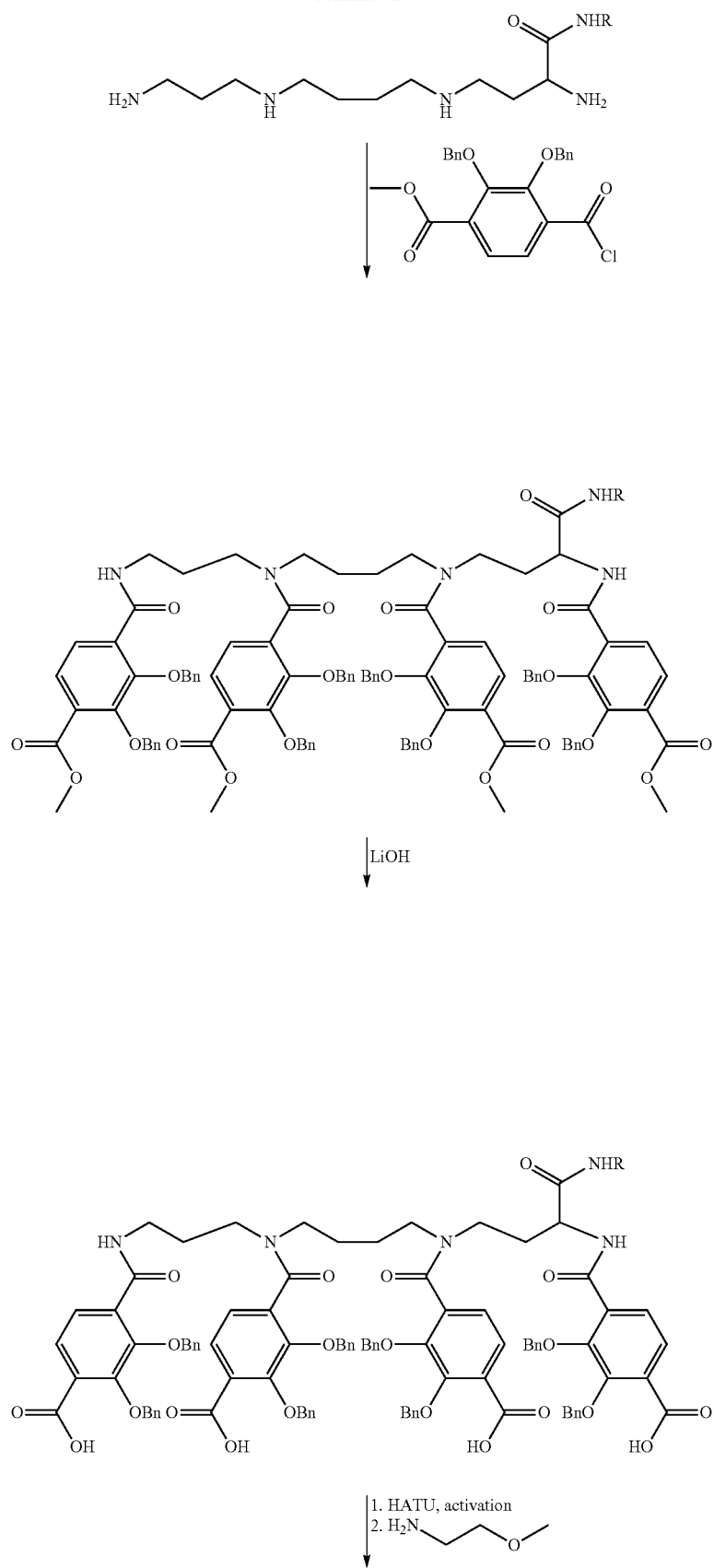

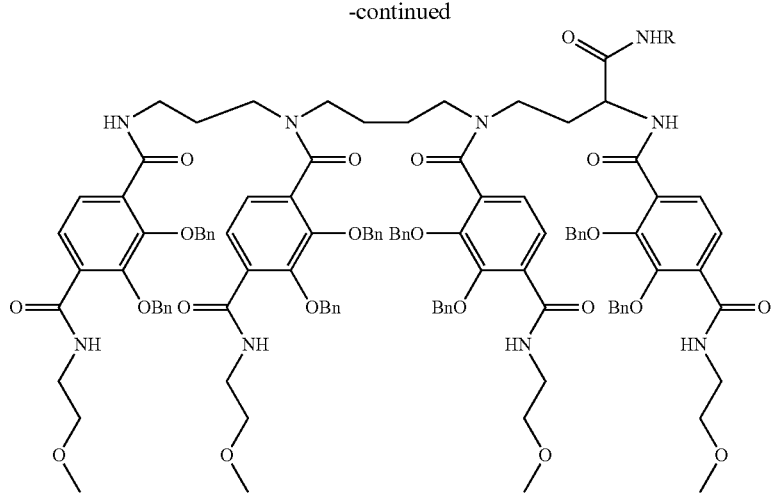
HCl/HOAC
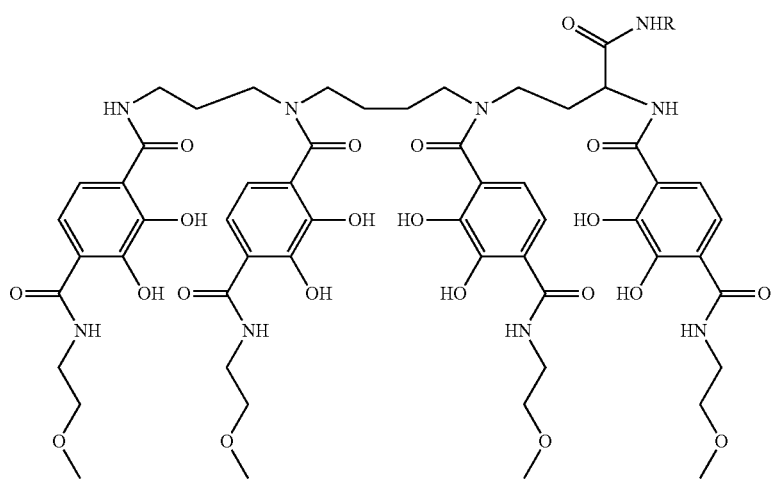
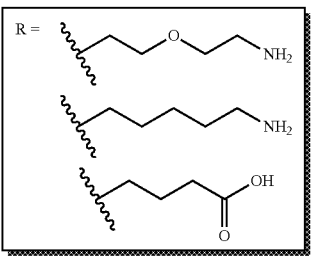

125
Example 9: Synthesis of Bifunctional Spermine Based MOE-IAM Chelators
126
-continued
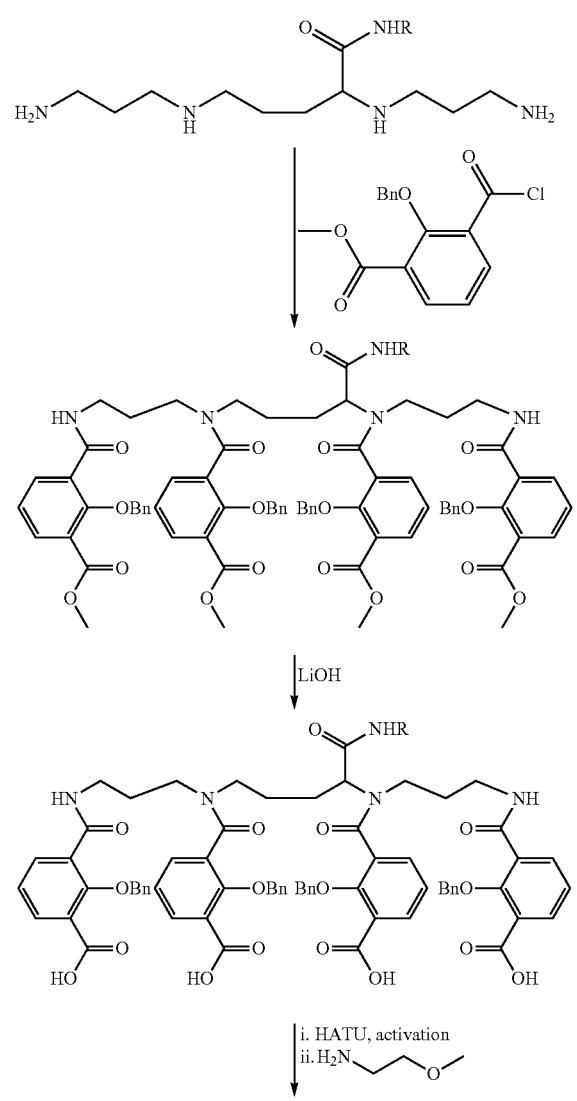
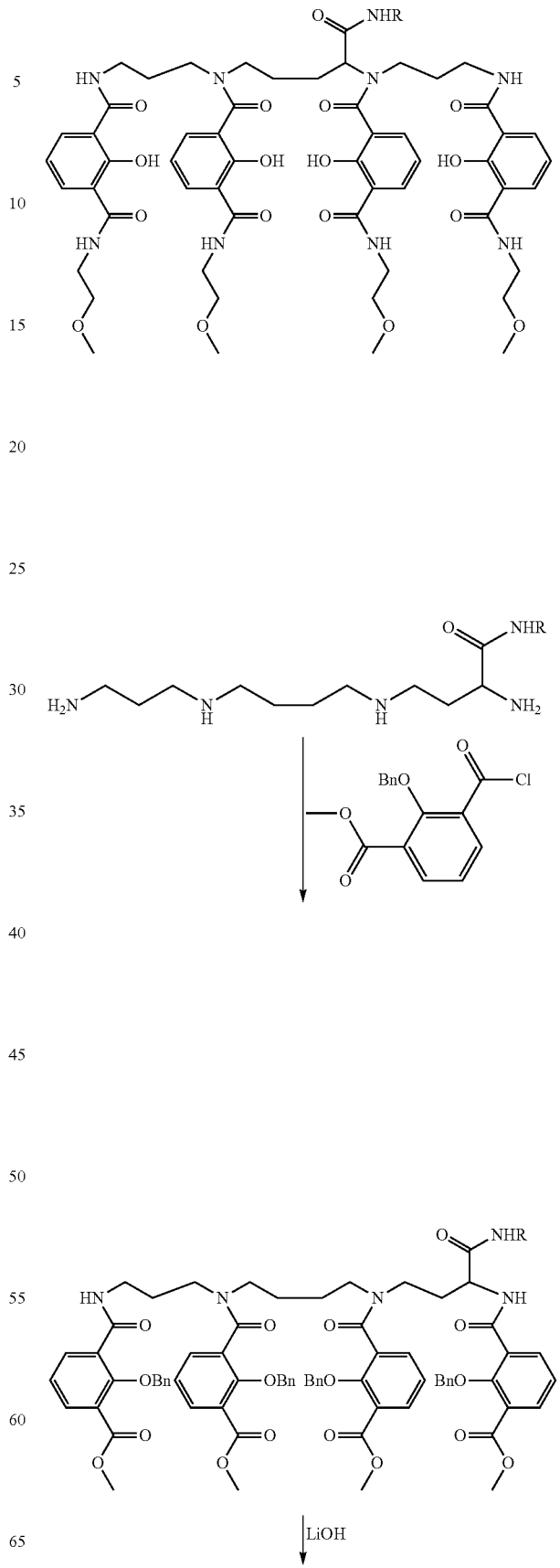

127
-continued
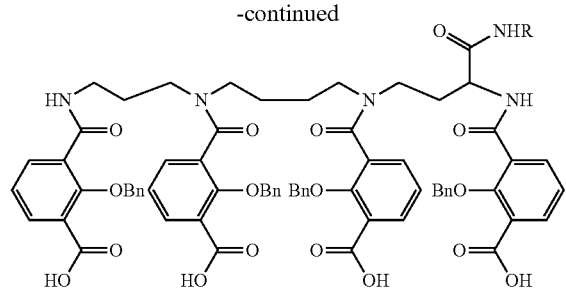
i. HATU, activation
ii. H$_2$N─CH$_2$CH$_2$─OCH$_3$
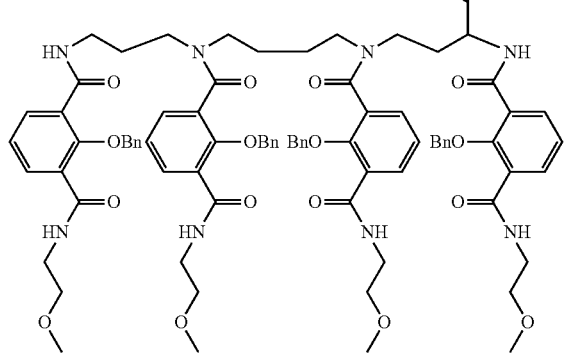
HCl/HOAC
128
-continued
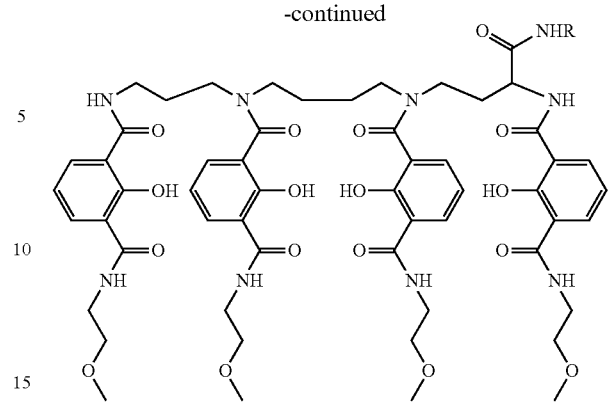
R = 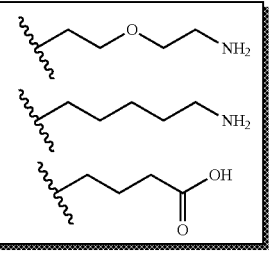
Example 10: Synthesis of Bifunctional Spermine Based MOE-12HOPO Chelators
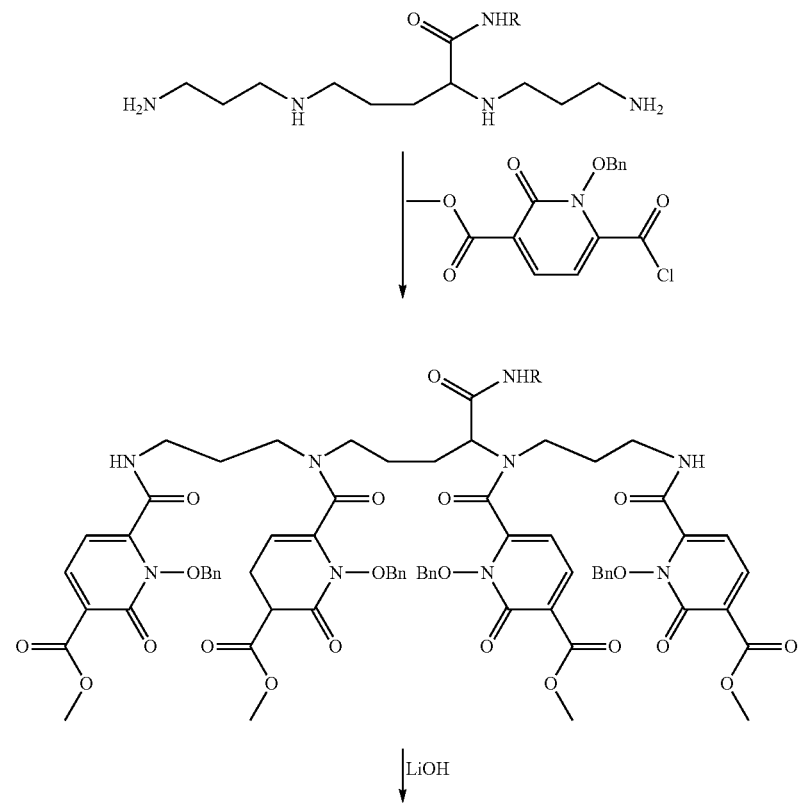
LiOH -continued
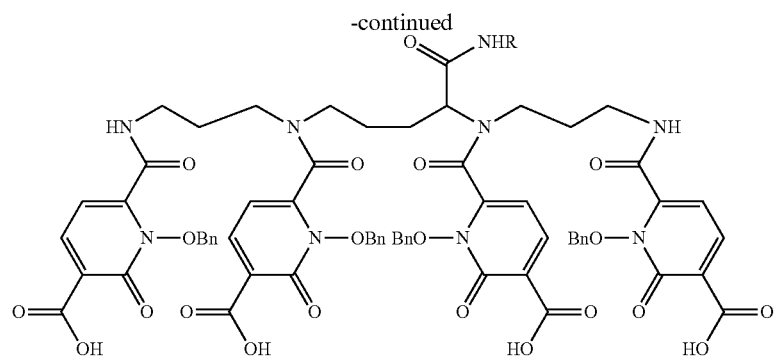
i. HATU, activation
ii. H₂N-CH₂CH₂-OCH₃
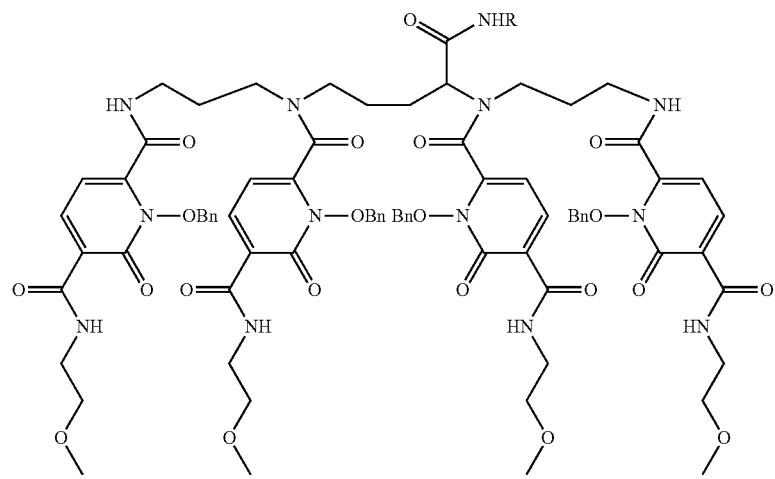
HCl/HOAC
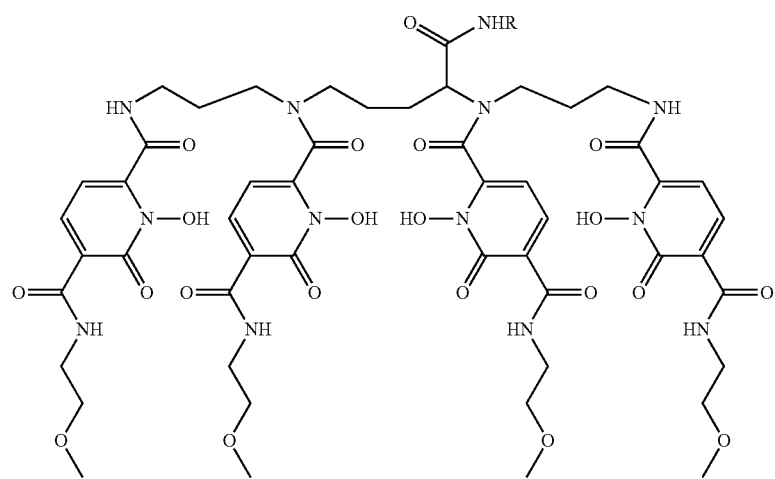

-continued
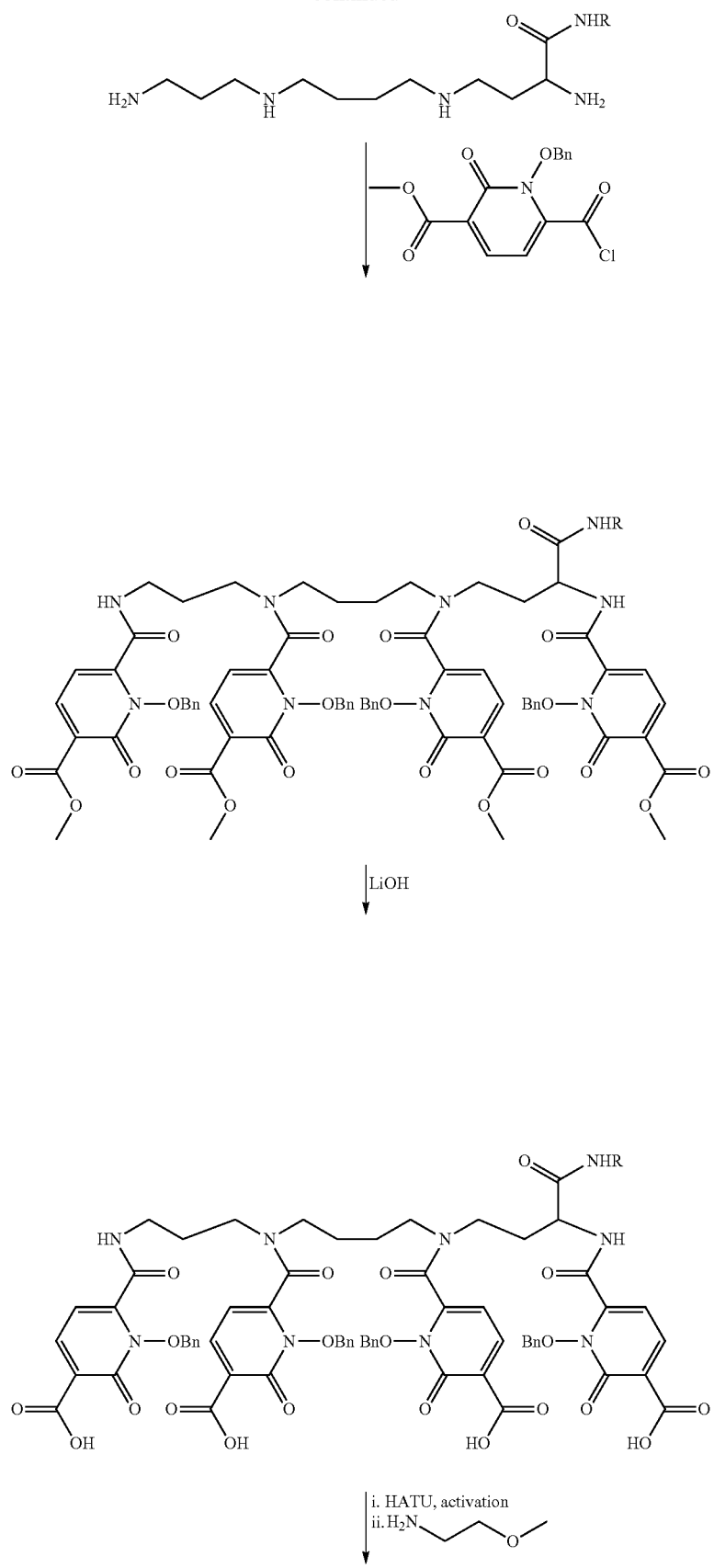

-continued
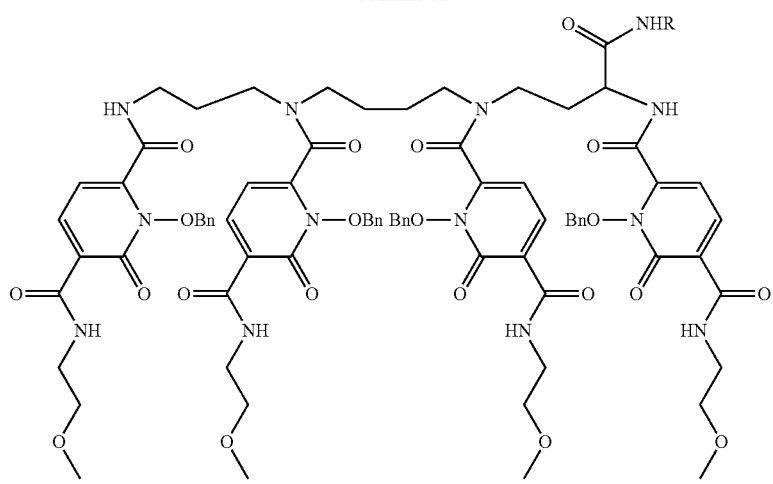
↓ HCl/HOAC
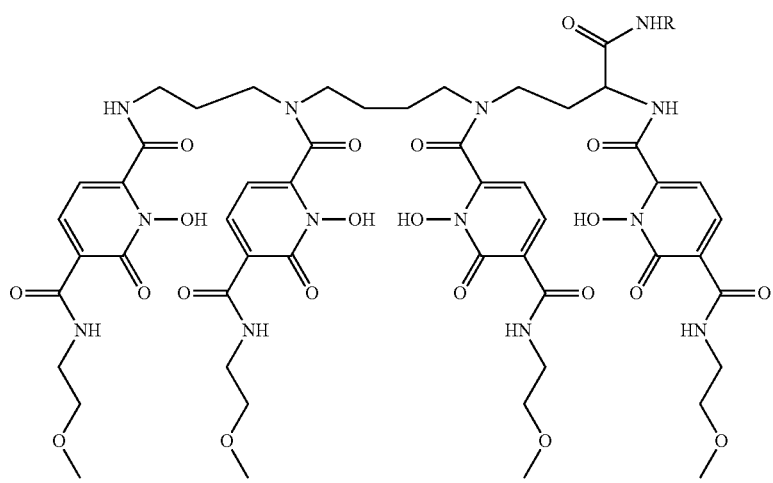
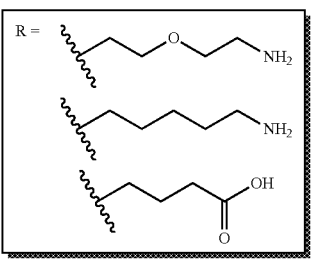

Example 11: Synthesis of Bifunctional Spermine Based MOE-6-Me-32HOPO Chelators
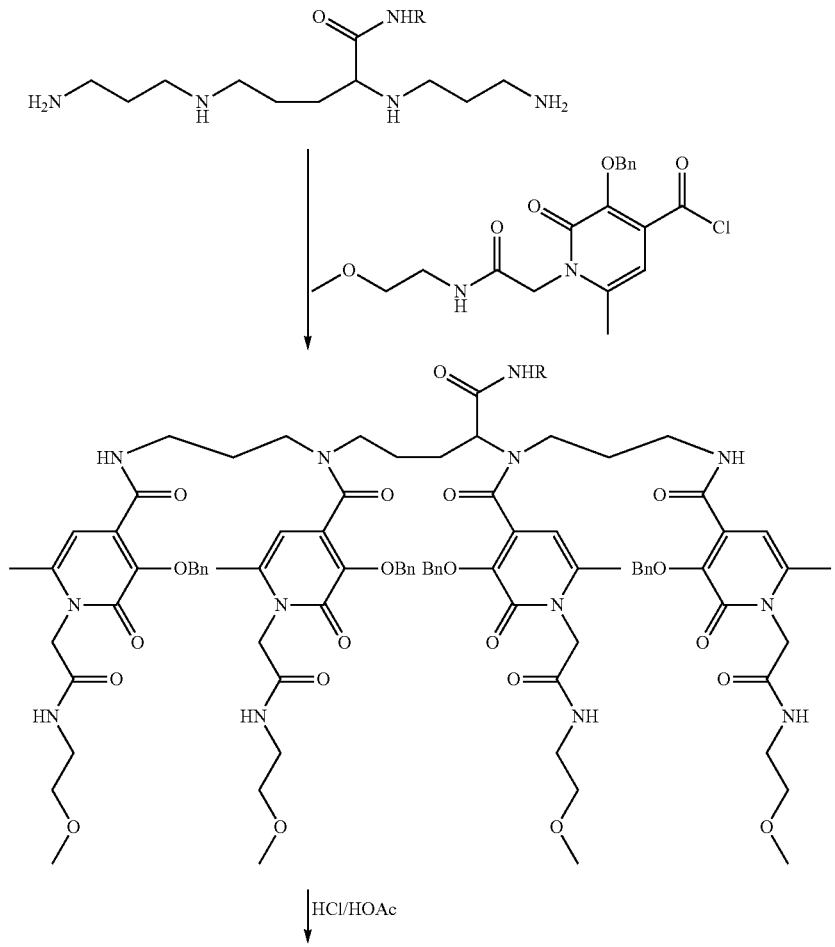
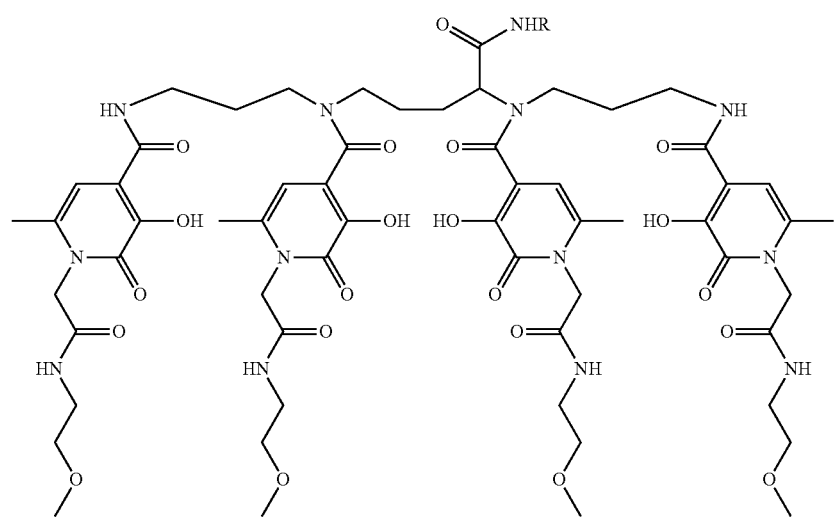
Central-functionalized 3,4,3-Li-6-Me-3,2-HOPODA (VIA)

-continued
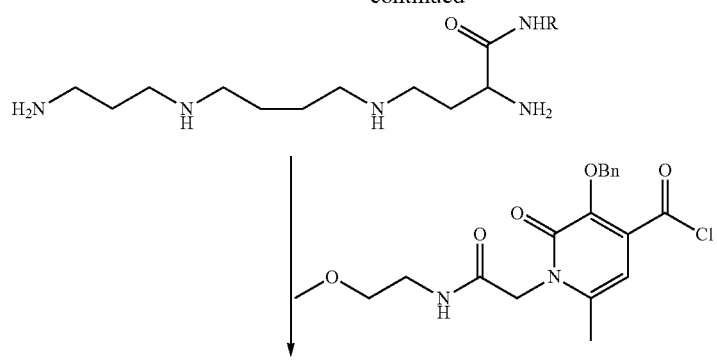
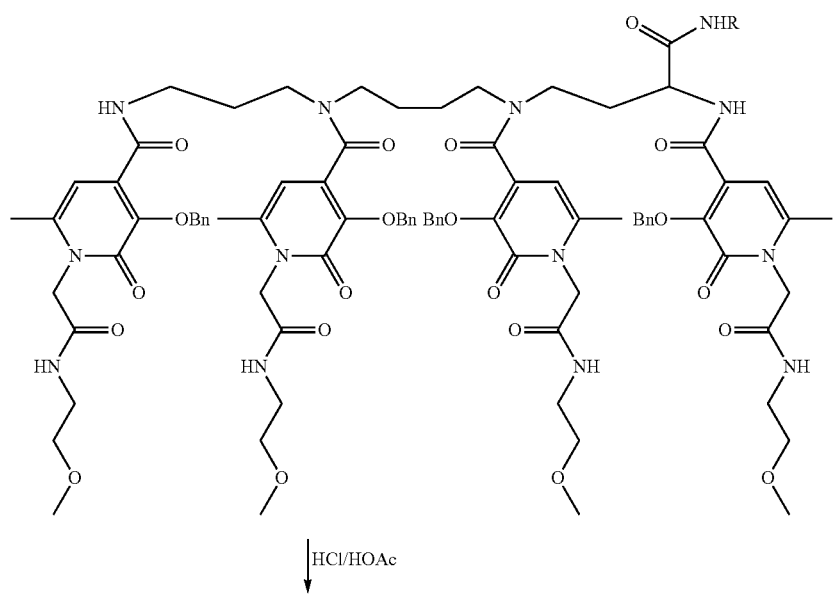
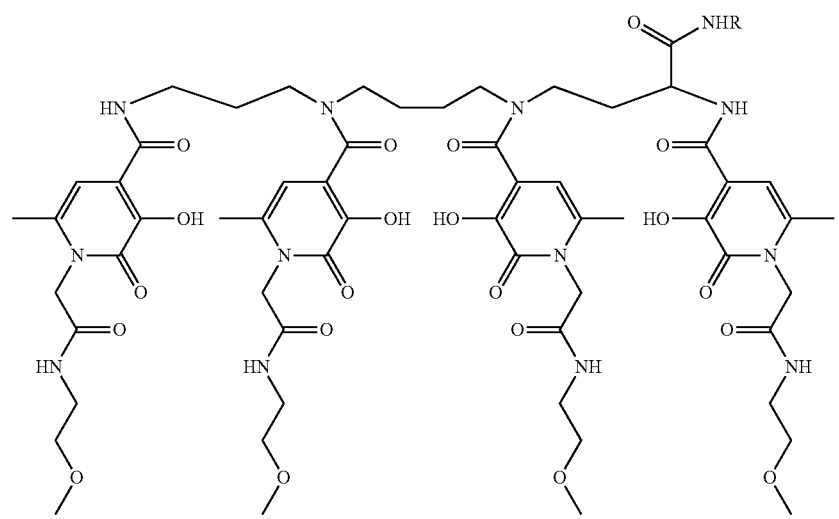
Side-functionalized 3,4,3-Li-6-Me-3,2-HOPODA (VIB)

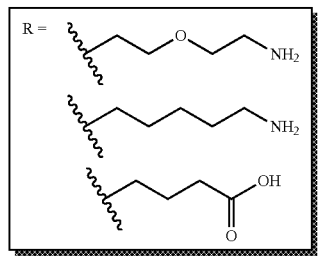

Example 12: 5LIO-Spermine-1,2-HOPO—NH2(Eu) Luminescent Bifunctional Chelate

Molar Extinction Coefficient of 5LIO-Spermine-1,2-HOPO—NH2 (2-8)

A solution of 1.20 mg (±0.01 mg) of the 5LIO-spermine-1,2-HOPO—NH2 ligand (from CHN analysis, fit as L.HCl.CH3OH.2H2O=985.39 g·mol$^{-1}$) in 50 mL 0.1 M TRIS buffer (pH 7.4) was prepared. The resulting absorption spectrum in a 1 cm cuvette is shown in FIG. 1.

This corresponds to $1.218 \times 10^{-6}$ moles of ligand in 50 mL and $c = 2.436 \times 10^{-5}$ M.

$A = \epsilon c l$, at $\lambda$max, A=0.42853 at 327 nm.

Calculated extinction coefficient of 5LIO-spermine-1,2-HOPO—NH$_2$ ligand based on CHN:

$\epsilon \sim 17,595$ M$^{-1}$ cm$^{-1}$ (±500 M$^{-1}$ cm$^{-1}$) at 327 nm; at $\lambda_{280nm}$, A=0.13722

Hence, the corresponding extinction coefficient of ~5655 M$^{-1}$ cm$^{-1}$ (±75 M$^{-1}$ cm$^{-1}$) at 280 nm. This yields a $\epsilon 280/\epsilon 327$ ratio of $17595/5655 = 3.11$ for protein labelling.

Molar Extinction Coefficient of [Eu(5LIO-spermine-1,2-HOPO—NH2)] (2-8-Eu)

Figures 2A, 2B:
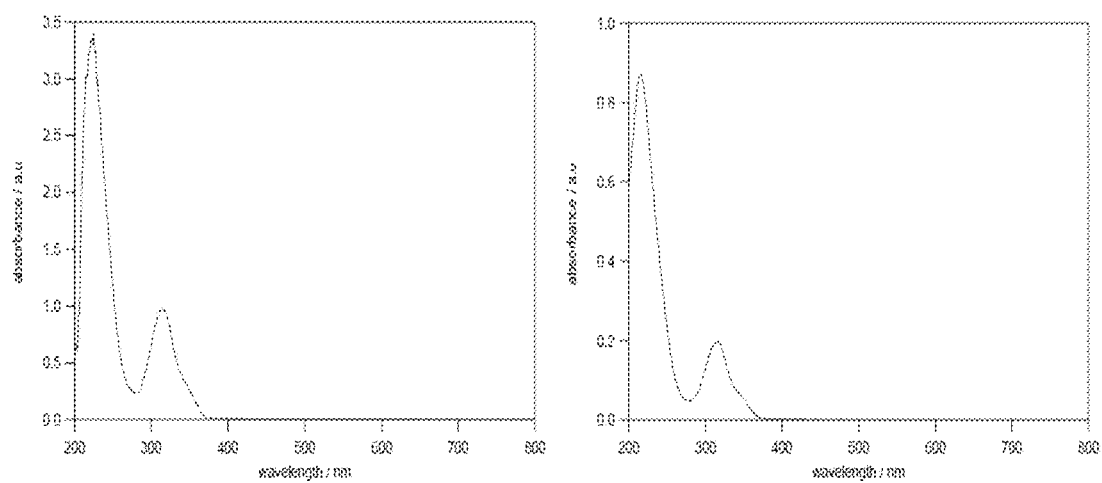
FIG. 2A-FIG. 2B shows Molar Extinction Coefficient of [Eu(5LIO-spermine-1,2-HOPO—NH2)] (2-8-Eu) as outlined in Example 12.

A solution of 3.01 mg (±0.01 mg) of the [Eu(5LIO-spermine-1,2-HOPO—NH2)] complex (from CHN analysis, fit as EuL.HCl.pyH.4H2O=1217.42 g·mol$^{-1}$) in 50 mL 0.1 M TRIS buffer (pH 7.4) was prepared. The resulting absorption spectra in 1 cm (and 2 mm) cuvettes are shown in FIG. 2A-FIG. 2B.

This corresponds to $2.472 \times 10^{-6}$ moles of ligand in 50 mL and $c = 4.945 \times 10^{-5}$ M.

$A = \epsilon c l$; at $\lambda$max, A=0.96915 at 315 nm.

Hence, calc'd extinction coefficient of [Eu(5LIO-spermine-1,2-HOPO—NH$_2$)] complex based on CHN:

$\epsilon \sim 19,600$ M$^{-1}$ cm$^{-1}$ (±500 M$^{-1}$ cm$^{-1}$) at 315 nm. At $\lambda_{280nm}$, A=0.23666

Hence, the corresponding extinction coefficient of ~4785 M$^{-1}$ cm$^{-1}$ (±75 M$^{-1}$ cm$^{-1}$) at 280 nm. This yields a $\epsilon 280/\epsilon 327$ ratio of $19600/4785 = 4.10$ for protein labelling.

Emission Spectrum of [Eu(5LIO-spermine-1,2-HOPO—NH2)] Complex (2-8-Eu)

Figure 3:
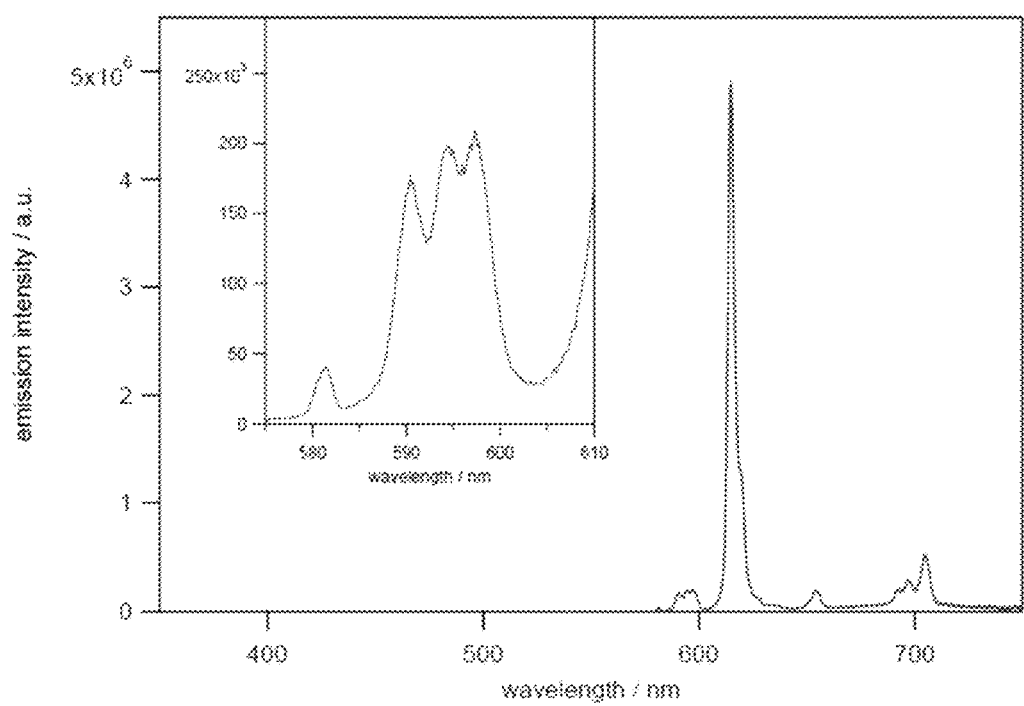
FIG. 3 shows Emission spectrum of [Eu(5LIO-spermine-1,2-HOPO—NH2)] complex (2-8-Eu) as outlined in Example 12.

The emission spectrum ($\lambda_{ex}$=316 nm) for a $9.890 \times 10^{-6}$ M solution (Abs~0.2) of the [Eu(5LIO-spermine-1,2-HOPO—NH2)] complex in 0.1 M TRIS buffer (pH 7.4) is shown in FIG. 3.

The spectrum confirms the presence of only a single emitting species in solution, evidenced by only a single $^5D0 \rightarrow ^7F0$ peak at ~581 nm. The spectrum is also typical for the Eu(III) cation in a low symmetry coordination environment, with 3 observed peaks for the $^5D0 \rightarrow ^7F1$ transition at 590-597 nm (see inset). The $^5D0 \rightarrow ^7F2$ peak is observed as a sharp intense peak at ~615 nm.

Luminescence Lifetime of [Eu(5LIO-spermine-1,2-HOPO—NH2)] Complex (2-8-Eu)

Figure 4:
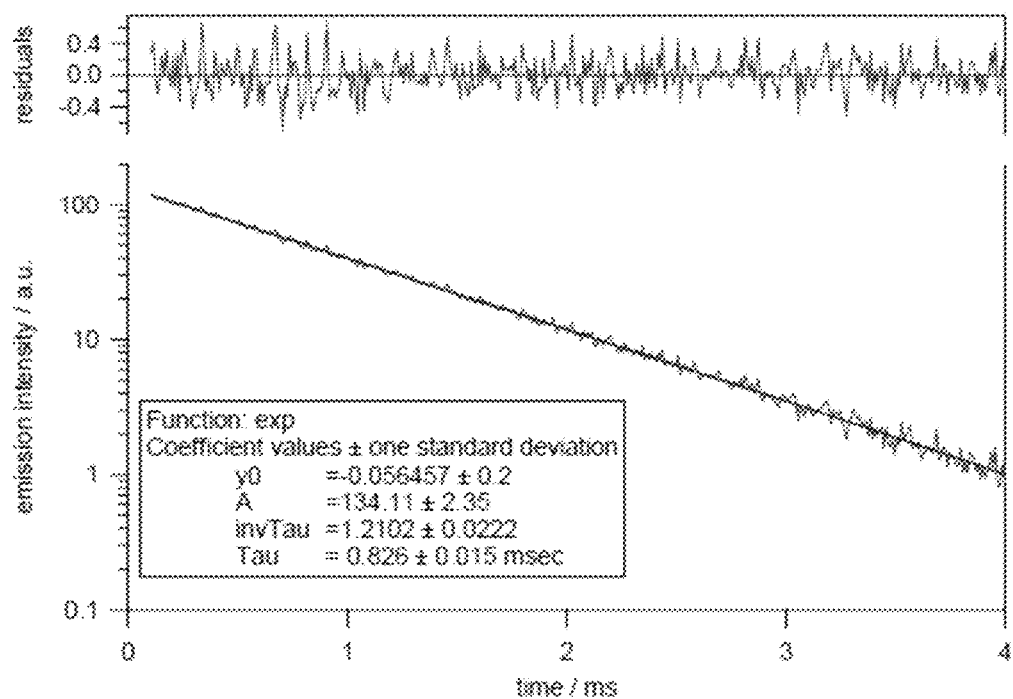
FIG. 4 shows Luminescence lifetime of [Eu(5LIO-spermine-1,2-HOPO—NH2)] complex (2-8-Eu) as outlined in Example 12.

The luminescence decay spectrum for a $9.890 \times 10^{-6}$ M solution (Abs~0.2) of the [Eu(5LIO-spermine-1,2-HOPO—NH$_2$)] complex in 0.1 M TRIS buffer (pH 7.4) is shown in FIG. 4.

The best fitting of the data to a mono-exponential lifetime gives a lifetime value of 0.83±0.02 msec and reduced chi squared value ($\chi^2$) of 1.052. Given the relatively long lifetime compared to other 1,2-HOPO derivatives (eg [Eu(H2,2-1,2-HOPO)] $\tau \sim 0.48$ msec, q=1, [Eu(5LIN-1,2-HOPO)2] $\tau \sim 0.728$ ms, q=0), the current complex is likely non hydrated (q=0) species.

Quantum Yield Determination for [Eu(5LIO-spermine-1,2-HOPO—NH2)] Complex (2-8-Eu)

Figure 5A:
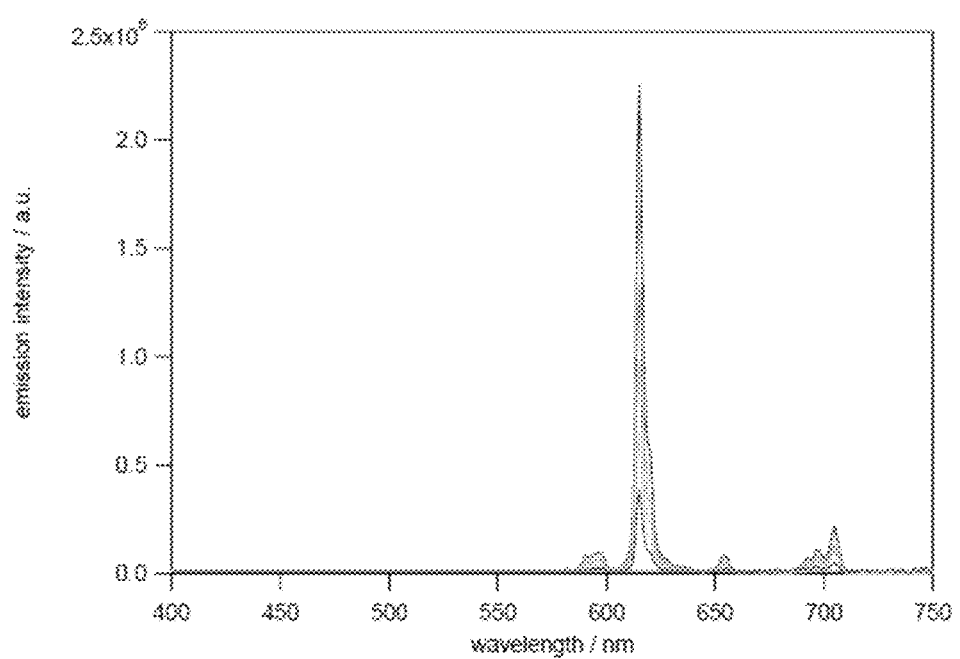
FIG. 5A-FIG. 5B shows Quantum Yield Determination for [Eu(5LIO-spermine-1,2-HOPO—NH2)] complex (2-8-Eu) as outlined in Example 12.
Figure 5B:
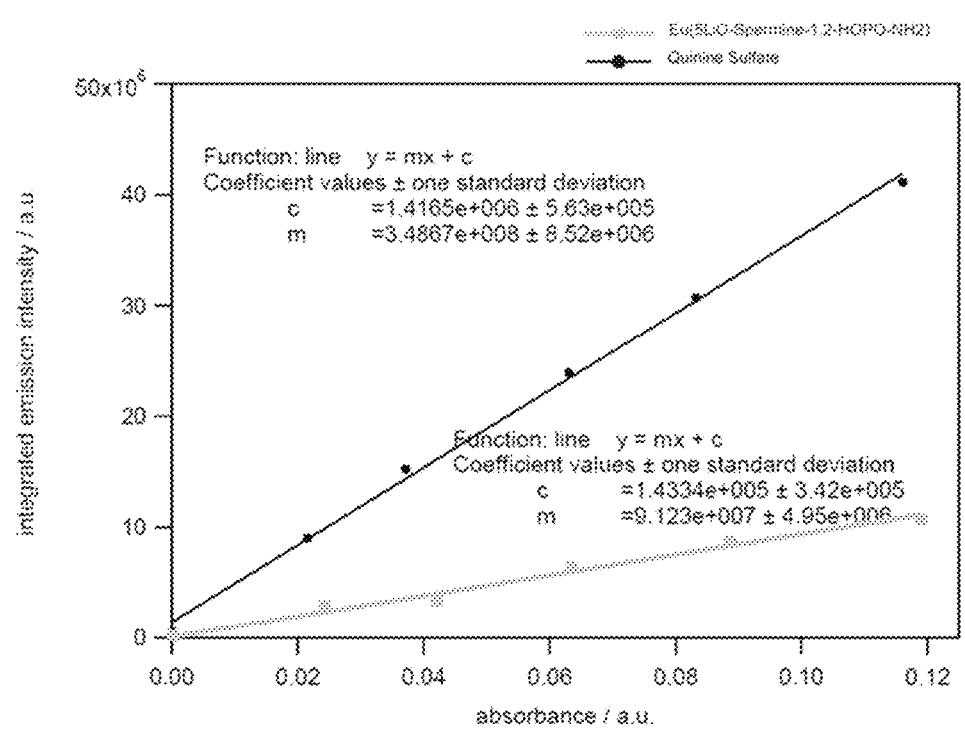

The luminescence quantum yield of the [Eu(5LIO-spermine-1,2-HOPO—NH2)] complex in 0.1 M TRIS (pH 7.4) was determined versus Quinine Sulfate in 0.5 M H2SO4 as a reference ($\Phi_{ref}$=0.546). The emission spectra for the Eu(III) complex are shown in FIG. 5A-FIG. 5B.

Corresponding quantum yield calculation:

$\varphi x = 9.123 \times 10^7 / 3.4867 \times 10^8 \times 0.546$ $= 0.1429$ $\sim 14.3\%$ (2.1%)

The obtained value is consistent with luminescence lifetime measurements suggesting the lack of any inner sphere water molecules (i.e. q=0).

Example 13: Synthesis of an Octacoordinating Spermine Bi-Functional 1,2-HOPO Europium Complex with Amine Reactive N-Hydroxysuccinimide Derivatized Linker

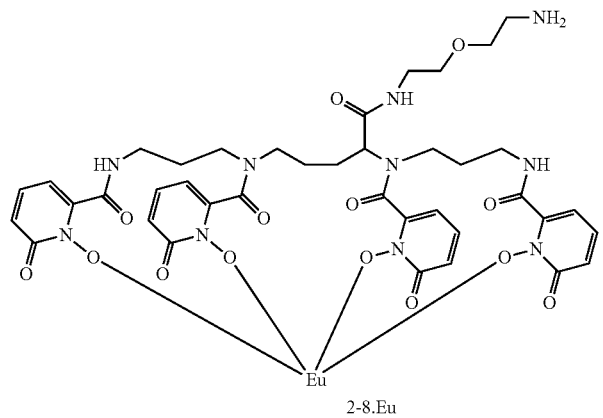

2-8.Eu

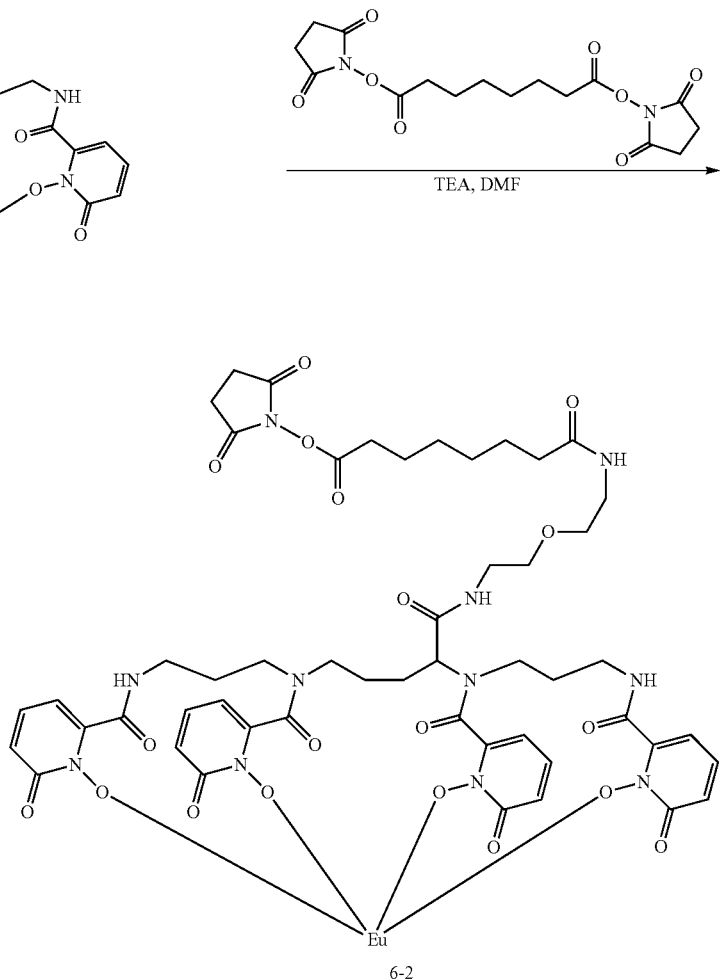

6-2

Octacoordinating Bifunctional Chelator, N-Hydroxysuccinimide Derivative 6-2

Europium complex 2-8.Eu (11.9 mg, 11.6 µmol) was partially dissolved in dimethylformamide (400 µL) and triethylamine (16.1 µL). To this suspension was transferred a solution of disuccinimidyl subarate (42.6 mg, 116 µmol) in dimethylformamide (200 µL). The resulting suspension was mixed at 1000 rpm under inert atmosphere for one hour. The suspension was centrifuged at 12,000 rpm for 1 minute, the supernatant was divided between three microtubes, and ether (ca. 1.8 mL per tube) was added. After 1 hr, the resulting suspension was centrifuged at 12,000 rpm for 3 minutes and the ether removed. The pellets were washed with ether (ca. 1.5 mL), centrifuged, the ether was removed, and the pellets were dried in vacuo. The pellets were washed with isopropyl alcohol (1500 µL), the denser precipitate was allowed to settle, and the lighter precipitate (excess disuccinimidyl subarate) and isopropyl alcohol wash were removed and discarded. This wash was repeated once. The resulting precipitate was washed with ether (1 mL/tube), centrifuged for 3 minutes, the ether removed, and the pellets dried in vacuo to provide N-hydroxysuccinimide derivative 6-2 (10.9 mg, 73.4%). FTMS-pESI: calculated for $C_{51}H_{59}N_{11}O_{19}Eu$ [M–H]⁻, 1280.3193, found, 1280.3198.

Example 14: Synthesis of an Octacoordinating Spermine Bi-Functional 1,2-HOPO Europium Complex Protein Conjugates To a solution of streptavidin (Prozyme SA-10, 18.2 µM, 1 mL) in 100 mM sodium bicarbonate buffer, pH 9, in an O-ring type microcentrifuge tube was added a solution of europium complex 6-2 (1.1 mg, 0.84 µmol dissolved in 167 µL dimethylformamide for 5 mM final concentration, 36.4 µL for 10 molar equivalents). The resulting solution was mixed at 800 rpm for two hours. The contents of the microtube were applied to a 10 mL Penefsky size exclusion column containing Sephadex G50 Fine equilibrated in 50 mM Tris, pH 7.6, 150 mM NaCl. The tube was centrifuged at ca. 700 rpm for 3 minutes and the eluent containing 6-2-SAv (SAv=streptavidin) collected. The concentration of protein was measured by UV-vis spectrometry using extinction coefficients for streptavidin at 280 nm of 3.2 mL/mg, and 4,782 and 19,600 $M^{-1}$ $cm^{-1}$ for the europium complex at 280 nm and 315 nm, respectively. The resulting solution was found to be 0.66 mg/mL protein in ca. 1 mL buffer. The degree of labeling was calculated to be 4.3 chelators per protein, using a molecular weight of 55,000 g/mol for streptavidin. A solution of IgG antibody (13.3 μM, 1 mL, Thermo-Fisher 31154) was conjugated with europium complex 6-2 using the same procedure, to yield a solution of 1.57 mg/mL of antibody conjugate 6-2-IgG (IgG=immunoglobulin G) in ca. 1 mL of buffer, assuming an extinction coefficient of 1.4 mL/mg at 280 nm. The degree of labeling was calculated to be 5.1 using a molecular weight of 150,000 g/mol for the IgG antibody. Diluted solutions of each conjugate were observed to fluoresce red when viewed using a long wave UV lamp, demonstrating presence of the europium(III) complex.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A compound having a structure selected from:

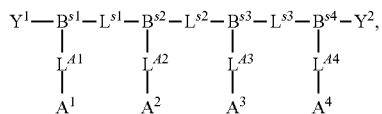

wherein
Y$^1$ and Y$^2$ are independently selected from H, substituted or unsubstituted alkyl, and substituted or unsubstituted heteroalkyl;
B$^{s1}$, B$^{s2}$, B$^{s3}$, and B$^{s4}$, are independently selected from N, CR$^s$, B, SiR$^s$, and P;
wherein R$^s$ is selected from H and unsubstituted C$_1$-C$_3$ alkyl;
L$^{A1}$, L$^{A2}$, L$^{A3}$, and L$^{A4}$, are independently selected from a bond, —C(O)—, substituted or unsubstituted alkyl, and substituted or unsubstituted heteroalkyl;
L$^{s1}$ and L$^{s3}$ are each independently selected from substituted or unsubstituted C$_2$, C$_3$, and C$_4$ alkyl; and
L$^{s2}$ is selected from substituted or unsubstituted C$_3$, C$_4$, and C$_5$ alkyl;
wherein at least one of L$^{s1}$, L$^{s2}$, and L$^{s3}$ is substituted with said linker; and
A$^1$, A$^2$, A$^3$, and A$^4$, are chelating moieties having a structure independently selected from

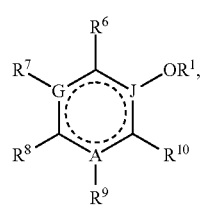

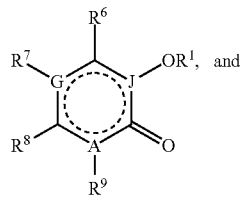

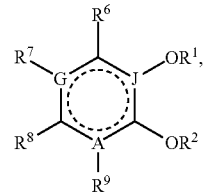

wherein
A and G are independently selected from carbon, nitrogen and oxygen;
J is selected from carbon and nitrogen;
each R$^1$ and R$^2$ is independently selected from H, and a single negative charge;
each R$^6$, R$^7$, R$^8$, and R$^9$ is independently selected from a bond to L$^{A1}$, L$^{A2}$, L$^{A3}$, L$^{A4}$, alkanediyl attached to L$^{A1}$, L$^{A2}$, L$^{A3}$, and L$^{A4}$ H, substituted or unsubstituted alkyl, substituted or unsubstituted heteroalkyl, halogen, CN, —CF$_3$, —C(O)R$^{17}$, —SO$_2$NR$^{17}$R$^{18}$, —NR$^{17}$R$^{18}$, —OR$^{17}$, —S(O)$_2$R$^{17}$, —COOR$^{17}$, —S(O)$_2$OR$^{17}$, —OC(O)R$^{17}$, —C(O)NR$^{17}$R$^{18}$, —(CH$_2$)$_m$C(O)NR$^{17}$R$^{18}$, —O(CH$_2$)$_m$C(O)NR$^{17}$R$^{18}$, —NR$^{17}$C(O)R$^{18}$, —NR$^{17}$SO$_{2R}^{18}$, and —NO$_2$,
wherein
at least two of R$^6$, R$^7$, R$^8$, and R$^9$ are optionally joined to form a ring system selected from substituted or unsubstituted cycloalkyl, substituted or unsubstituted heterocycloalkyl, substituted or unsubstituted aryl and substituted or unsubstituted heteroaryl;
m is an integer selected from 1, 2, 3, 4, 5, and 6;
R$^{17}$ and R$^{18}$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and
R$^{17}$ and R$^{18}$, together with the atoms to which they are attached, are optionally joined to form a 5-, 6- or 7-membered ring;
when A is oxygen, R$^9$ is not present; and
when G is oxygen, R$^7$ is not present;
A$^1$ is attached to L$^{A1}$ through a member selected from R$^6$, R$^7$, R$^8$, R$^9$ and R$^{10}$;
A$^2$ is attached to L$^{A2}$ through a member selected from R$^6$, R$^7$, R$^8$, R$^9$ and R$^{10}$;
A$^3$ is attached to L$^{A3}$ through a member selected from R$^6$, R$^7$, R$^8$, R$^9$ and R$^{10}$; and
A$^4$ is attached to L$^{A4}$ through a member selected from R$^6$, R$^7$, R$^8$, R$^9$ and R$^{10}$;
wherein said compound comprises a linker.

2. The compound according to claim 1, wherein when $A^1$ has a structure according to formula (I), $A^1$ is attached to $L^{A1}$ through $R^6$ or $R^{10}$;

when $A^1$ has a structure according to formula (II) or (III), $A^1$ is attached to $L^{A1}$ through $R^6$ or $R^9$;

when $A^2$ has a structure according to formula (I), $A^2$ is attached to $L^{A2}$ through $R^6$ or $R^{10}$;

when $A^2$ has a structure according to formula (II) or (III), $A^2$ is attached to $L^{A2}$ through $R^6$ or $R^9$;

when $A^3$ has a structure according to formula (I), $A^3$ is attached to $L^{A3}$ through $R^6$ or $R^{10}$;

when $A^3$ has a structure according to formula (II) or (III), $A^3$ is attached to $L^{A3}$ through $R^6$ or $R^9$;

when $A^4$ has a structure according to formula (I), $A^4$ is attached to $L^{A4}$ through $R^6$ or $R^{10}$; and when $A^4$ has a structure according to formula (II) or (III), $A^4$ is attached to $L^{A4}$ through $R^6$ or $R^9$.

3. The compound according to claim 1, wherein $A^1$, $A^2$, $A^3$, and $A^4$ are each independently selected from:

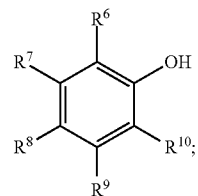
(1)

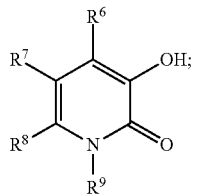
(2a)

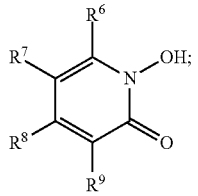
(2b)

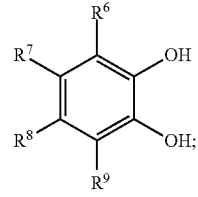
(3)

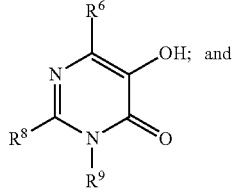
(4)

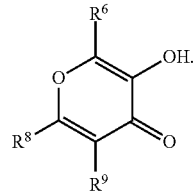
(5)

4. The compound according to claim 3, wherein when $A^1$ has a structure according to formula (1), $A^1$ is attached to $L^{A1}$ through $R^6$ or $R^9$;

when $A^1$ has a structure according to formula (2a), (2b), (3), (4) or (5), $A^1$ is attached to $L^{A1}$ through $R^6$ or $R^9$;

when $A^2$ has a structure according to formula (1), $A^2$ is attached to $L^{A2}$ through $R^6$ or $R^9$;

when $A^2$ has a structure according to formula (2a), (2b), (3), (4) or (5), $A^2$ is attached to $L^{A2}$ through $R^6$ or $R^9$;

when $A^3$ has a structure according to formula (1), $A^3$ is attached to $L^{A3}$ through $R^6$ or $R^9$;

when $A^3$ has a structure according to formula (2a), (2b), (3), (4) or (5), $A^3$ is attached to $L^{A3}$ through $R^6$ or $R^9$;

when $A^4$ has a structure according to formula (1), $A^4$ is attached to $L^{A4}$ through $R^6$ or $R^{10}$; and when $A^4$ has a structure according to formula (2a), (2b), (3), (4) or (5), $A^4$ is attached to $L^{A4}$ through $R^6$ or $R^9$.

5. The compound according to claim 1, wherein $A^1$, $A^2$, $A^3$, and $A^4$ are each independently selected from:

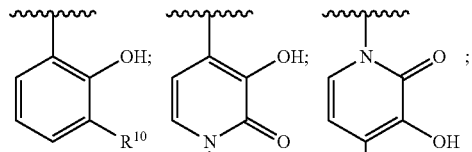

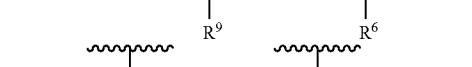

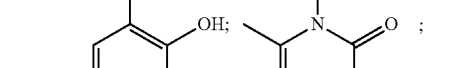

6. The compound according to claim 1, wherein $B^{s1}$, $B^{s2}$, $B^{s3}$, and $B^{s4}$ are each N.

7. The compound according to claim 1, wherein $L^{A1}$, $L^{A2}$, $L^{A3}$, and $L^{A4}$ are independently selected from a bond, —C(O)—, —(CH$_2$)$_a$C(O)—, and —O(CH$_2$)$_a$C(O)—; wherein a is an integer selected from 1, 2, 3, 4, 5, and 6.

8. The compound according to claim 1, wherein $L^{A1}$, $L^{A2}$, $L^{A3}$, and $L^{A4}$ are the same.

9. The compound according to claim 1, wherein $L^{A1}$, $L^{A2}$, $L^{A3}$, and $L^{A4}$ are each —C(O)—.

10. The compound according to claim 1, wherein $Y^1$ and $Y^2$ are each H.

11. The compound according to claim 1, having the structure

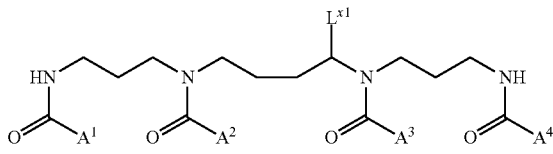

wherein $L^{x1}$ is said linker.

12. The compound according to claim 1, having the structure

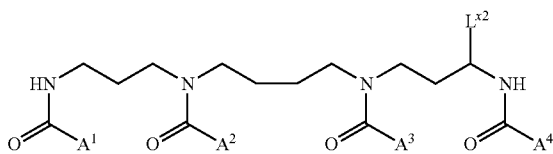

wherein $L^{x2}$ is said linker.

13. The compound according to claim 1, having the structure

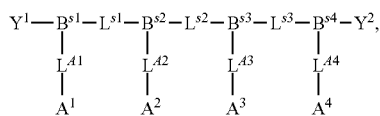

wherein
 Y$^1$ is substituted alkyl comprising said linker;
 Y$^2$ is H;
 B$^{s1}$, B$^{s2}$, B$^{s3}$, and B$^{s4}$ are N;
 L$^{s1}$, L$^{s2}$, and L$^{s3}$ are each independently selected from unsubstituted $C_3$-$C_4$ alkyl;
 L$^{A1}$, L$^{A2}$, L$^{A3}$, and L$^{A4}$ are —C(O)—; and
 A$^1$, A$^2$, A$^3$, and A$^4$ are chelating moieties having the structure

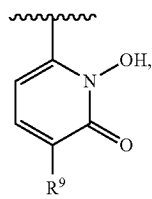

wherein R$^9$ is H.

14. The compound according to claim 1, wherein said linker has the structure -L$^{11}$-X,
 wherein L$^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and
 X is selected from a reactive functional group, a protected functional group, and a targeting moiety.

15. The compound according to claim 1, wherein said linker has the structure:

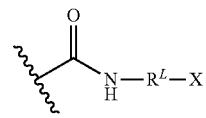

wherein R$^L$ is selected from substituted or unsubstituted alkyl, and substituted or unsubstituted heteroalkyl; and
 X is selected from a reactive functional group, a protected functional group, and a targeting moiety.

16. The compound according to claim 1, wherein said linker has a structure selected from:

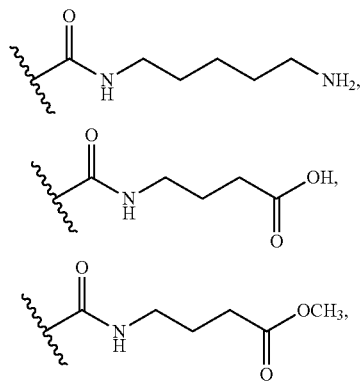

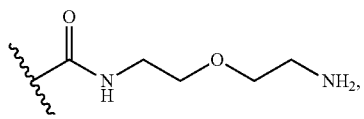

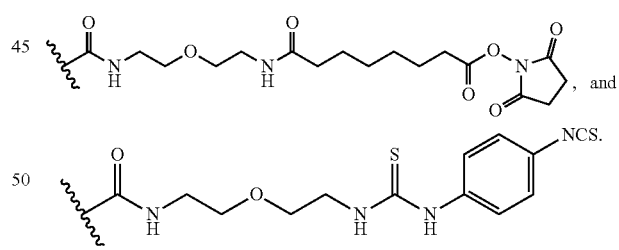

17. The compound according to claim 1, wherein, R$^6$, or R$^9$ of each chelating moiety comprises a member selected from substituted or unsubstituted alkyl, substituted or unsubstituted heteroalkyl, halogen, CN, —CF$_3$, —C(O)R$^{17}$, —SO$_2$NR$^{17}$R$^{18}$, —NR$^{17}$R$^{18}$, —OR$^{17}$, —S(O)$_2$R$^{17}$, —COOR$^{17}$, —S(O)$_2$OR$^{17}$, —OC(O)R$^{17}$, —C(O)NR$^{17}$R$^{18}$, —(CH$_2$)$_m$C(O)NR$^{17}$R$^{18}$, —O(CH$_2$)$_m$C(O)NR$^{17}$R$^{18}$, —NR$^{17}$C(O)R$^8$, —NR$^{17}$SO$_2$R$^{18}$, and —NO$_2$.

18. The compound according to claim 17, wherein R$^6$, or R$^9$ of each chelating moiety is selected from substituted or unsubstituted alkoxyalkyl and a substituted or unsubstituted polyether.

19. The compound according to claim 1, having a structure selected from:

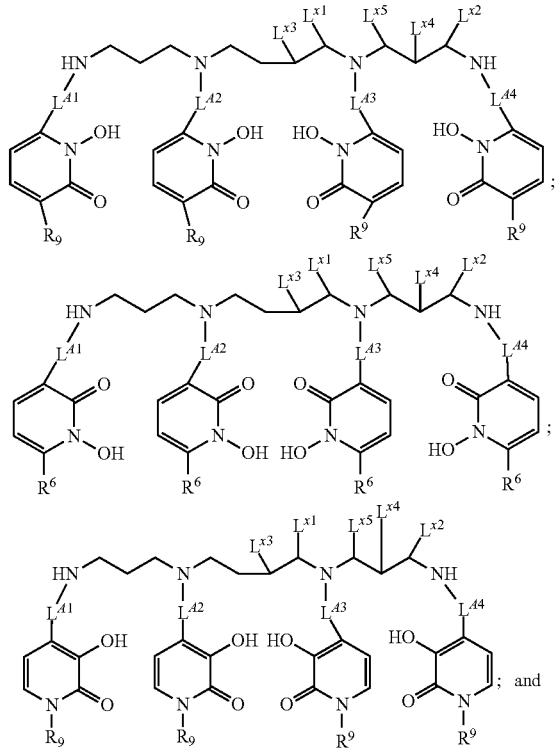

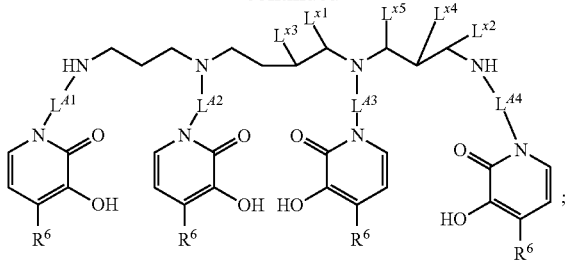

wherein $L^{x1}$, $L^{x2}$, $L^{x3}$, $L^{x4}$, and $L^{x5}$ are independently selected from H and a linker, with the proviso that at least one of $L^{x1}$, $L^{2}$, $L^{x3}$, $L^{x4}$, and $L^{x5}$ is said linker; and each $R^6$ and $R^9$ comprises a member selected from substituted or unsubstituted alkyl, substituted or unsubstituted heteroalkyl, halogen, CN, —$CF_3$, —$C(O)R^{17}$, —$SO_2NR^{17}R^{18}$, —$NR^{17}R^{18}$, —$OR^{17}$, —$S(O)_2R^{17}$, —$COOR^{17}$, —$S(O)_2OR^{17}$, —$OC(O)R^{17}$, —$C(O)NR^{17}R^{18}$, —$(CH_2)_mC(O)NR^{17}R^{18}$, —$O(CH_2)_mC(O)NR^{17}R^{18}$, —$NR^{17}C(O)R^{18}$, —$NR^{17}SO_2R^{18}$, and —$NO_2$.

20. The compound according to claim 1, having a structure selected from:

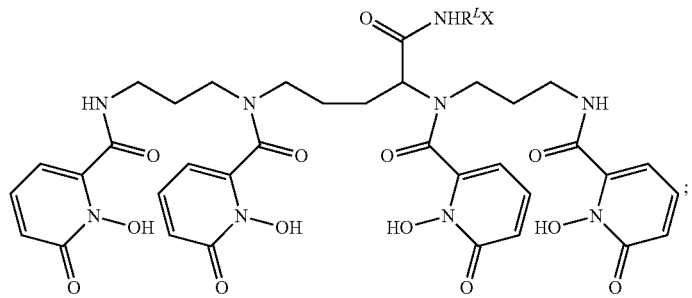

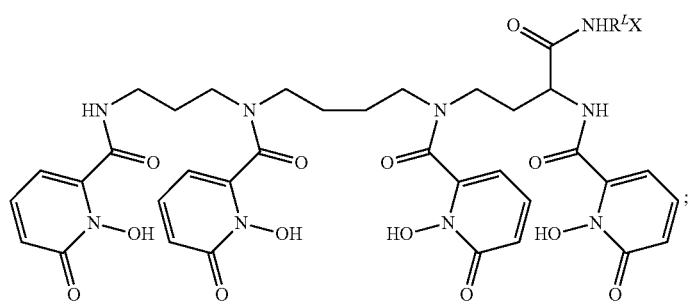

-continued
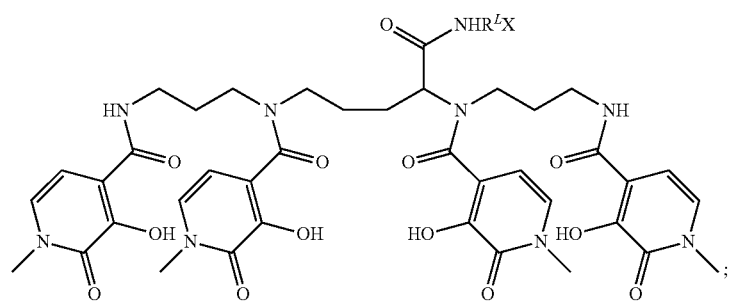
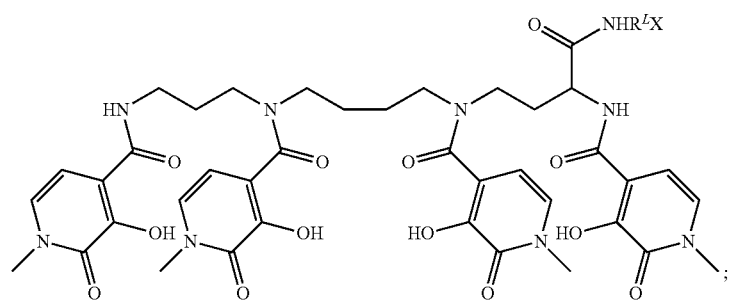
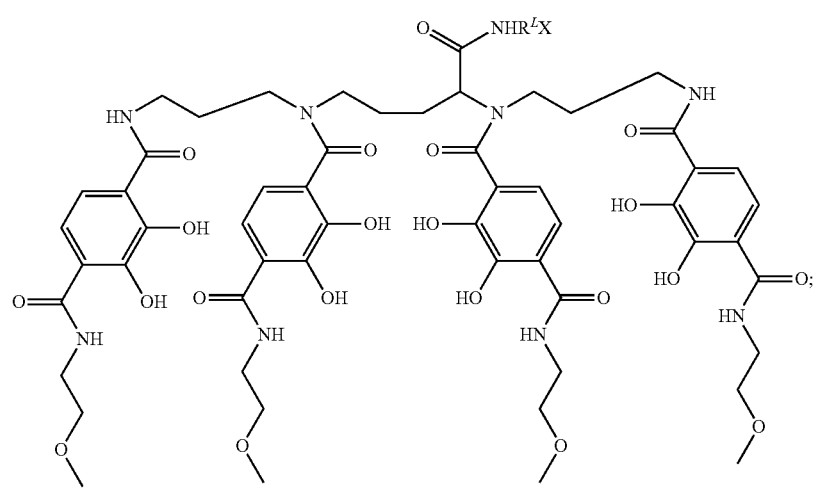
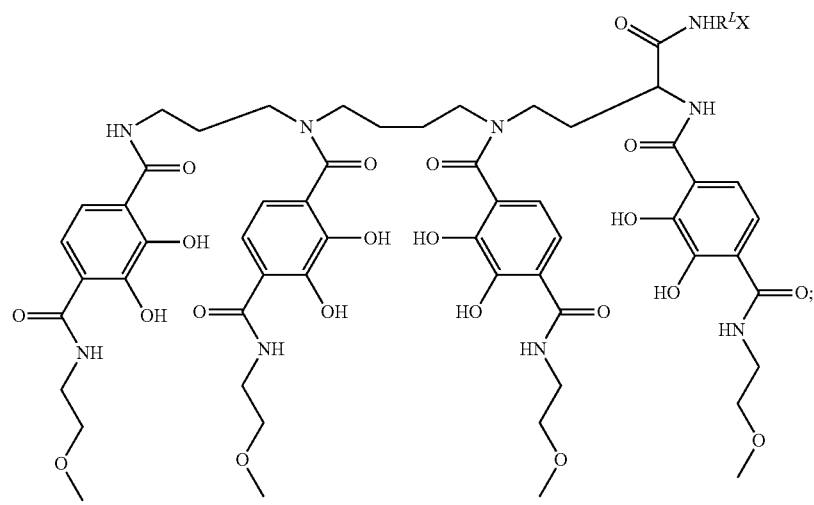

-continued
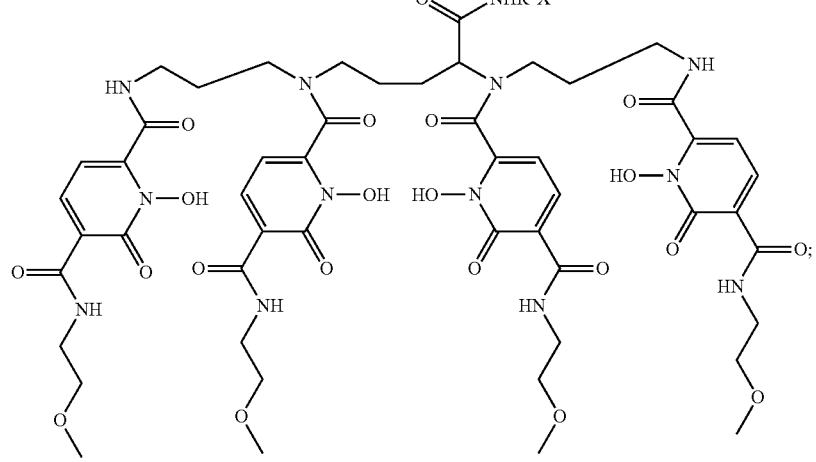
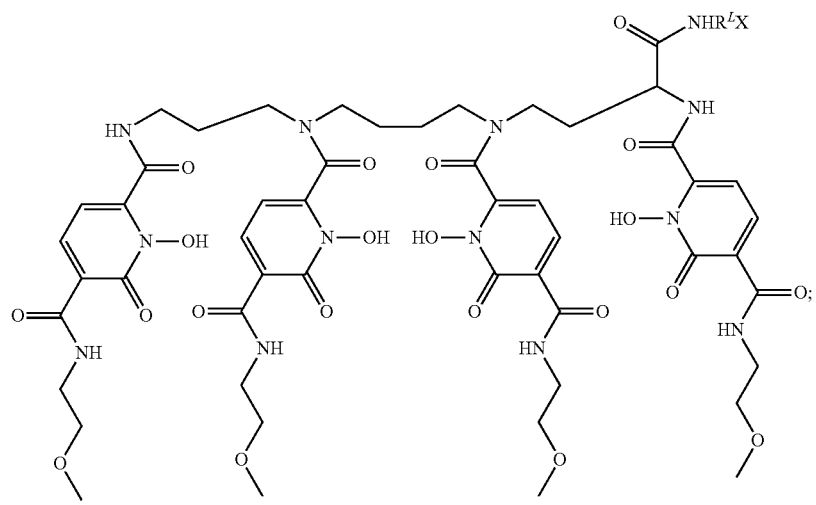
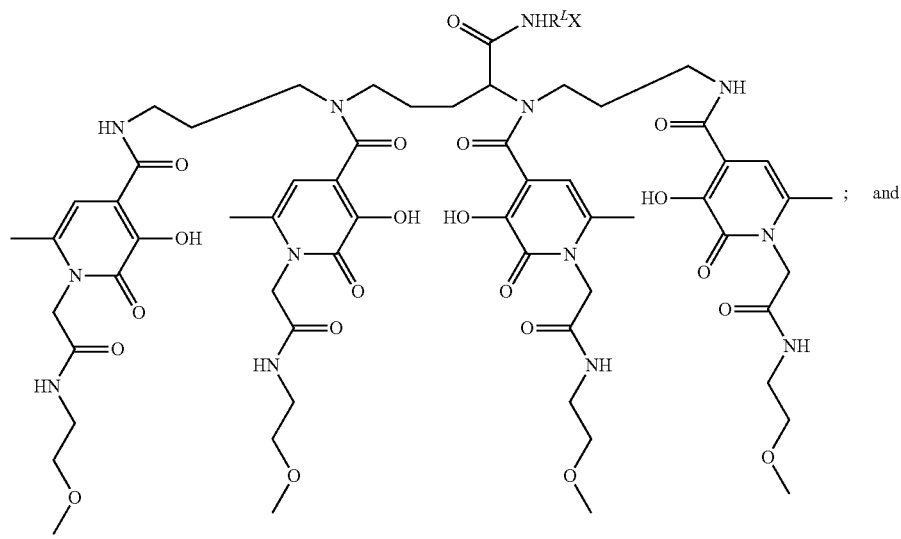
; and

-continued

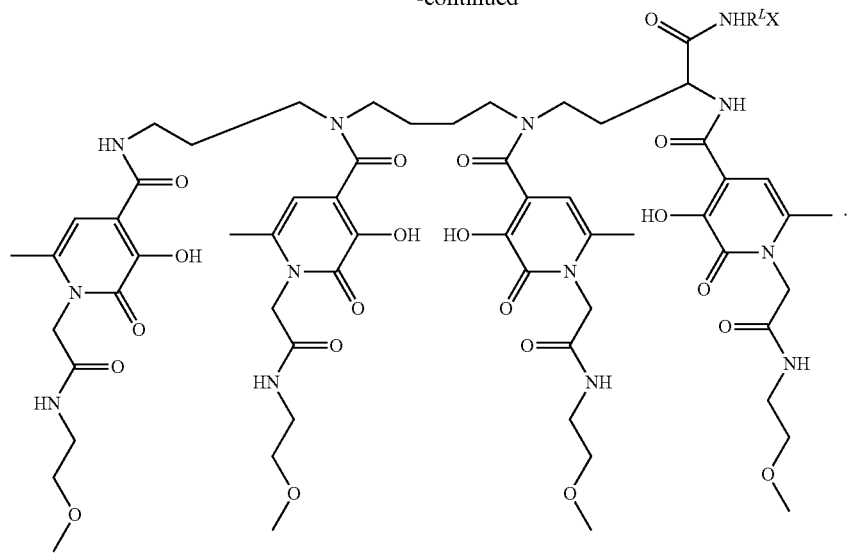

wherein $R^L$ is selected from substituted or unsubstituted alkyl, and substituted or unsubstituted heteroalkyl; and X is a reactive functional group or a targeting moiety.

21. The compound according to claim 20, wherein —$R^L$—X has a structure selected from:

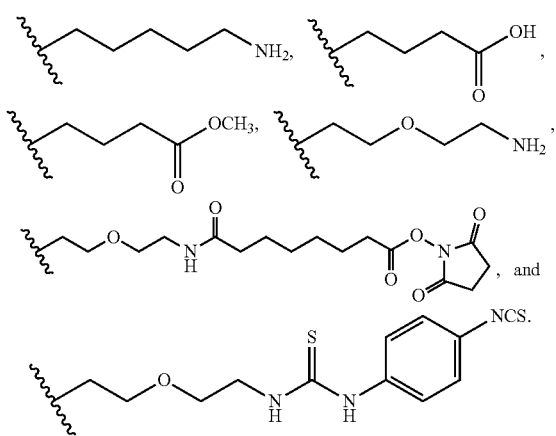

22. A complex comprising a compound according to claim 1 and a metal ion.

23. The complex according to claim 22, wherein the metal is selected from a lanthanide, an actinide, yttrium (Y), and zirconium (Zr).

24. The complex according to claim 22, wherein the metal is selected from post-transition metals, metalloids, indium (In), gallium (Ga) and bismuth (Bi).

25. The complex according to claim 22, wherein said complex is luminescent.

26. The complex according to claim 23, wherein said lanthanide is luminescent.

27. The complex according to claim 23, wherein said lanthanide is selected from terbium (Tb), europium (Eu), dysprosium (Dy), and samarium (Sm).

28. The complex according to claim 23, wherein said lanthanide is gadolinium (Gd).

29. The complex according to claim 23, wherein said actinide is thorium (Th).

30. The complex according to claim 22, wherein the metal is a radionuclide.

31. The complex according to claim 30, wherein said metal is selected from $^{177}$Lu, $^{166}$Ho, $^{153}$Sm, $^{90}$Y, $^{86}$Y, $^{166}$Dy, $^{165}$Dy, $^{169}$Er, $^{175}$Yb, $^{225}$Ac, $^{149}$Tb, $^{153}$Gd, and $^{230}$U.

32. The complex according to claim 30, wherein said metal ion is $^{227}$Th(IV), $^{89}$Zr(IV), $^{177}$Lu(III), or $^{225}$Ac(III).

* * * * *